US008334301B2

(12) United States Patent  
Nishida et al.

(10) Patent No.: US 8,334,301 B2
(45) Date of Patent: Dec. 18, 2012

(54) 5-MEMBERED HETEROCYCLIC COMPOUND

(75) Inventors: Haruyuki Nishida, Osaka (JP); Yasuyoshi Arikawa, Osaka (JP); Keizo Hirase, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 27 days.

(21) Appl. No.: 12/680,184

(22) PCT Filed: Sep. 24, 2008

(86) PCT No.: PCT/JP2008/067208
§ 371 (c)(1),
(2), (4) Date: Mar. 26, 2010

(87) PCT Pub. No.: WO2009/041447
PCT Pub. Date: Apr. 2, 2009

(65) Prior Publication Data
US 2010/0210696 A1  Aug. 19, 2010

(30) Foreign Application Priority Data

Sep. 28, 2007 (JP) .................. 2007/256275
Aug. 27, 2008 (JP) .................. 2008/218852

(51) Int. Cl.
*A61K 31/415* (2006.01)
*C07D 233/00* (2006.01)

(52) U.S. Cl. ...... 514/303; 514/403; 546/119; 548/356.1
(58) Field of Classification Search .................. 514/303, 514/403; 546/119; 548/356.1
See application file for complete search history.

(56) References Cited

U.S. PATENT DOCUMENTS

| 4,020,082 | A | 4/1977 | Marchetti |
| 6,989,391 | B2 * | 1/2006 | Pinto et al. ..................... 514/303 |
| 6,995,172 | B2 * | 2/2006 | Pinto et al. ..................... 514/303 |
| 7,005,435 | B2 * | 2/2006 | Pinto et al. ..................... 514/303 |
| 2004/0132788 | A1 | 7/2004 | Chabrier De Lassauniere et al. |
| 2008/0009543 | A1 | 1/2008 | Ducoux et al. |
| 2008/0269303 | A1 | 10/2008 | Barth et al. |
| 2009/0118335 | A1 | 5/2009 | Hasuoka et al. |

FOREIGN PATENT DOCUMENTS

| DE | 2108437 | 11/1971 |
| DE | 2503436 | 8/1975 |
| EP | 1803709 A1 | 7/2007 |
| EP | 2005957 A1 | 12/2008 |
| FR | 2 881 744 A1 | 8/2006 |
| GB | 1490771 | 11/1977 |
| WO | WO-2004/103968 A1 | 12/2004 |
| WO | WO-2005/063736 A1 | 7/2005 |
| WO | WO-2005/087229 A1 | 9/2005 |
| WO | WO-2006/036024 A1 | 4/2006 |
| WO | WO-2007/026916 A1 | 3/2007 |
| WO | WO-2007/068815 A2 | 6/2007 |
| WO | WO-2007114338 A1 | 10/2007 |
| WO | WO-2008/017932 A2 | 2/2008 |
| WO | WO-2009/041705 A2 | 4/2009 |

OTHER PUBLICATIONS

International Search Report, PCT/ISA/210, dated Oct. 28, 2008.
Bioorganic & Medicinal Chemistry, 2004, vol. 12, No. 21, pp. 5515-5524.
Journal of Medicinal Chemistry, 2002, vol. 45, No. 21, pp. 4655-4668.
Chemical & Pharmaceutical Bulletin, 1998, vol. 46, No. 2, pp. 279-286.
Journal of Medicinal Chemistry, 1994, vol. 37, No. 8, pp. 1189-1199.
Bioorganic & Medicinal Chemistry Letters, 2004, vol. 14, No. 21, pp. 5263-5267.
Supplementary European Search Report for related application EP08833168, dated May 11, 2011.
English Translation of Written Opinion dated May 4, 2010 for corresponding PCT Application No. PCT/JP2008/067208.
XP007920705;"$C_{21}H_{28}N_2O$", Patent Chemistry, Apr. 1, 2010.
XP007920706, "1-(4-fluorobenzyl)-3-<4-(4-methyoxyphenyl)piperazin-1-yl-methyl>-5-phenyl-1H-1,2,4-triazole", Patent Chemistry, Apr. 1, 2010.
XP007920707, "5-benzyl-4-phenyl-2-piperidin-1-ylmethyl-2,4-dihydro-[1,2,4]triazole-3-thione", Patent Chemistry, Apr. 1, 2010.

* cited by examiner

*Primary Examiner* — Susannah Chung
(74) *Attorney, Agent, or Firm* — Edwards Wildman Palmer LLP; David G. Conlin; Weiying Yang

(57) ABSTRACT

Provided is a compound having a superior acid secretion suppressive action, which shows an antiulcer activity and the like.
A compound represented by the formula (I) or a salt thereof:

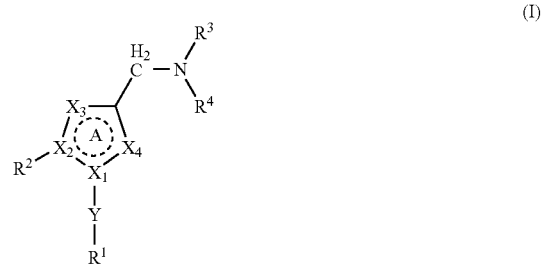

wherein ring A is a saturated or unsaturated 5-membered heterocycle containing, as a ring-constituting atom besides carbon atoms, at least one heteroatom selected from a nitrogen atom, an oxygen atom and a sulfur atom, the ring-constituting atoms $X_1$ and $X_2$ are the same or different and each is C or N, the ring-constituting atoms $X_3$ and $X_4$ are the same or different and each is C, N, O or S (provided that a pyrrole ring wherein $X_1$ is N is excluded from ring A), and when the ring-constituting atom $X_3$ or $X_4$ is C or N, each ring-constituting atom optionally has substituent(s) selected from an optionally substituted alkyl, an acyl, an optionally substituted hydroxy, an optionally substituted mercapto, an optionally substituted amino, a halogen, a cyano and a nitro;
$R^1$ and $R^2$ are each a cyclic group optionally having substituent(s); $R^3$ and $R^4$ are each H or alkyl, or $R^3$ and $R^4$ form, together with the adjacent N, an nitrogen-containing heterocycle; and Y is a spacer.

9 Claims, No Drawings

5-MEMBERED HETEROCYCLIC COMPOUND

TECHNICAL FIELD

The present invention relates to 5-membered heterocyclic compounds having an acid secretion suppressive activity.

BACKGROUND OF THE INVENTION

Proton pump inhibitors represented by omeprazole, which suppress secretion of gastric acid for the treatment of peptic ulcer, reflux esophagitis and the like, have been widely used in clinical situations. However, the existing proton pump inhibitors are associated with problems in terms of effect and side effects. To be specific, since the existing proton pump inhibitors are unstable under acidic conditions, they are often formulated as enteric preparations, in which case several hours are required before onset of the effect, and about 5 days to exhibit maximum efficacy by consecutive administration. In addition, since the existing proton pump inhibitors show variation of treatment effects due to metabolic enzyme polymorphism and drug interaction with medicaments such as diazepam and the like, an improvement has been desired.

As pyrrole compounds having a proton pump inhibitory action, patent reference 1 describes a compound represented by the formula:

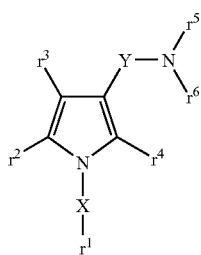

wherein X and Y are the same or different and each is a bond or a spacer having 1 to 20 atoms in the main chain, $r^1$ is an optionally substituted hydrocarbon group or an optionally substituted heterocyclic group, $r^2$, $r^3$ and $r^4$ are the same or different and each is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group, an optionally substituted pyrimidinyl group, an acyl group, a halogen atom, a cyano group or a nitro group, and $r^5$ and $r^6$ are the same or different and each is a hydrogen atom or an optionally substituted hydrocarbon group.

As pyrrole compounds having a proton pump inhibitory action, patent reference 2 describes a compound represented by the formula:

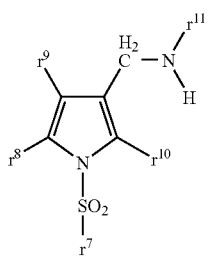

wherein $r^7$ is an monocyclic nitrogen-containing heterocyclic group optionally condensed with a benzene ring or heterocycle, which optionally has substituent(s), $r^8$ is an optionally substituted $C_{6-14}$ aryl group, an optionally substituted thienyl group or an optionally substituted pyridyl group, $r^9$ and $r^{10}$ are the same or different and each is a hydrogen atom, or one of $r^9$ and $r^{10}$ is a hydrogen atom, and the other is an optionally substituted lower alkyl group, an acyl group, a halogen atom, a cyano group or a nitro group, and $r^{11}$ is an alkyl group.

As a therapeutic drug for neoplastic diseases or autoimmune diseases, patent reference 3 describes a compound represented by the formula:

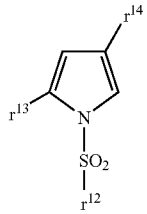

wherein $r^{12}$ is aryl, aralkyl, heteroaryl and the like, $r^{13}$ is aryl, heteroaryl and the like, and $r^{14}$ is aryl, heteroaryl, optionally substituted aminomethyl and the like.

As compounds having a proton pump inhibitory action, patent reference 4 describes a compound represented by the formula:

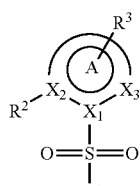

wherein ring A is a saturated or unsaturated 5- or 6- membered ring group optionally containing, as a ring-constituting atom besides carbon atoms, 1 to 4 heteroatoms selected from a nitrogen atom, an oxygen atom and a sulfur atom, and the ring-constituting atoms $X_1$ and $X_2$ are the same or different and each is a carbon atom or a nitrogen atom, $R^1$ is an optionally substituted aryl group or an optionally substituted heteroaryl group, $R^2$ is an optionally substituted alkyl group, an optionally substituted aryl group or an optionally substituted heteroaryl group, and $R^3$ is a substituent on the ring-constituting atom other than $X_1$, $X_2$ and $X_3$, which optionally has substituent(s) selected from a lower alkyl group, a halogen atom, a cyano group and oxo.

In addition, as a compound having a carbonic anhydrase inhibitory action, patent document 5 describes a compound represented by the formula

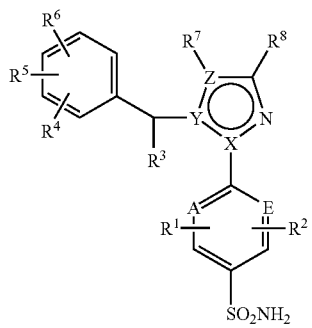

wherein A and E are the same or different and each is a carbon atom or a nitrogen atom, when ring-constituting atom X is a carbon atom, Y is a nitrogen atom and Z is a carbon atom, when ring-constituting atom X is a nitrogen atom, Y is a carbon atom and Z is a carbon atom or a nitrogen atom, $R^1$ and $R^2$ are the same or different and each is a hydrogen atom, a halogen atom, a $C_{1-6}$ alkyl group and the like, $R^3$ is a hydrogen atom, a halogen atom, a $C_{1-6}$ alkyl group, $(CH_2)_t CN$ (t is 0 to 6) and the like, $R^4$, $R^5$ and $R^6$ are the same or different and each is a hydrogen atom, a halogen atom, a $C_{2-12}$ alkenyl group and the like, $R^7$ and $R^8$ are the same or different and each is a hydrogen atom, a halogen atom, $(CH_2)_t(C_3\text{-}C_{12})$ cycloalkyl (t is 0 to 6) and the like, or $R^7$ and $R^8$ optionally form a 6-membered heterocycle.

patent document 1: WO 2006/036024
patent document 2: WO 2007/026916
patent document 3: WO 2004/103968
patent document 4: WO 2007/114338
patent document 5: WO 2008/017932

DISCLOSURE OF THE INVENTION

Problems to be Solved by the Invention

A medicament that effectively suppresses gastric acid secretion as known proton pump inhibitors, which is improved in instability under acidic conditions, variability of effects due to metabolic enzyme polymorphism and drug interaction, which are problems of known proton pump inhibitors, is expected to show more superior treatment effect on peptic ulcer, reflux esophagitis and the like. As the situation stands, however, a proton pump inhibitor capable of sufficiently satisfying these requirements has not been found. It is therefore an object of the present invention to provide a compound having a superior acid secretion suppressive effect (particularly, proton pump inhibitory effect), which has been improved in these problems.

Means of Solving the Problems

The present inventors have conducted various studies and found that a compound represented by the formula (I):

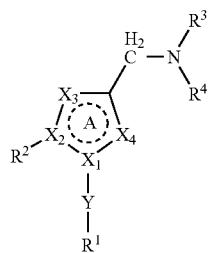

(I)

wherein
ring A is a saturated or unsaturated 5-membered heterocycle containing, as a ring-constituting atom besides carbon atoms, at least one heteroatom selected from a nitrogen atom, an oxygen atom and a sulfur atom, the ring-constituting atoms $X_1$ and $X_2$ are the same or different and each is a carbon atom or a nitrogen atom, the ring-constituting atoms $X_3$ and $X_4$ are the same or different and each is a carbon atom, a nitrogen atom, an oxygen atom or a sulfur atom (provided that a pyrrole ring wherein $X_1$ is a nitrogen atom is excluded from ring A), and when the ring-constituting atoms $X_3$ or $X_4$ is a carbon atom or a nitrogen atom, each ring-constituting atom optionally has substituent(s) selected from an optionally substituted alkyl group, an acyl group, an optionally substituted hydroxy group, an optionally substituted mercapto group, an optionally substituted amino group, a halogen atom, a cyano group and a nitro group;

$R^1$ and $R^2$ are the same or different and each is a cyclic group optionally having substituent(s) (provided that $R^2$ is not a cyclic group having an aminosulfonyl group as a substituent);

$R^3$ and $R^4$ are the same or different and each is a hydrogen atom or an alkyl group, or $R^3$ and $R^4$ optionally form, together with the adjacent nitrogen atom, an optionally substituted nitrogen-containing heterocycle;

Y is a spacer selected from
(1) a bond,
(2) a divalent $C_{1-6}$ hydrocarbon group optionally having substituent(s),
(3) $-O-(R^5)_m-(R^6)_n-$ wherein $R^5$ is a divalent $C_{1-6}$ hydrocarbon group optionally having substituent(s), $R^6$ is an oxygen atom, $-S(O)_w-$ wherein w is 0, 1 or 2), or

wherein $R^7$ is a hydrogen atom, an optionally substituted hydrocarbon group, an optionally substituted $C_{1-6}$ alkyl-carbonyl or an optionally substituted $C_{1-6}$ alkylsulfonyl, m is 0 or 1, n is 0 or 1, (4)

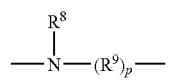

wherein $R^8$ is a hydrogen atom, an optionally substituted hydrocarbon group, an optionally substituted $C_{1-6}$ alkyl-carbonyl or an optionally substituted $C_{1-6}$ alkylsulfonyl, $R^9$ is a divalent $C_{1-6}$ hydrocarbon group optionally having substituent(s),
p is 0 or 1,
(5) $-S(O)_q-$ wherein q is 0 or 1, and
(6) $-S(O)_r-R^{10}-$ wherein $R^{10}$ is a divalent $C_{1-6}$ hydrocarbon group optionally having substituent(s), an oxygen atom or

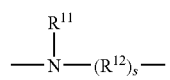

wherein $R^{11}$ is a hydrogen atom, an optionally substituted hydrocarbon group, an optionally substituted $C_{1-6}$ alkyl-carbonyl or an optionally substituted $C_{1-6}$ alkylsulfonyl, $R^{12}$ is a divalent $C_{1-6}$ hydrocarbon group optionally having substituent(s) or $-SO_2-$, s is 0 or 1, r is 0, 1 or 2, or a salt thereof [hereinafter to be sometimes abbreviated as compound (I)] unexpectedly has a very strong proton pump inhibitory effect, and is fully satisfactory as a medicament, which resulted in the completion of the present invention.

Accordingly, the present invention relates to [1] a compound represented by the formula (I):

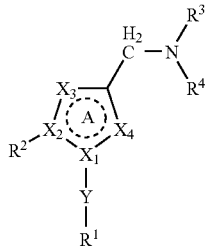
(I)

wherein ring A is a saturated or unsaturated 5-membered heterocycle containing, as a ring-constituting atom besides carbon atoms, at least one heteroatom selected from a nitrogen atom, an oxygen atom and a sulfur atom, the ring-constituting atoms $X_1$ and $X_2$ are the same or different and each is a carbon atom or a nitrogen atom, the ring-constituting atoms $X_3$ and $X_4$ are the same or different and each is a carbon atom, a nitrogen atom, an oxygen atom or a sulfur atom (provided that a pyrrole ring wherein $X_1$ is a nitrogen atom is excluded from ring A), and when the ring-constituting atom $X_3$ or $X_4$ is a carbon atom or a nitrogen atom, each ring-constituting atom optionally has substituent(s) selected from an optionally substituted alkyl group, an acyl group, an optionally substituted hydroxy group, an optionally substituted mercapto group, an optionally substituted amino group, a halogen atom, a cyano group and a nitro group;

$R^1$ and $R^2$ are the same or different and each is a cyclic group optionally having substituent(s);

$R^3$ and $R^4$ are the same or different and each is a hydrogen atom or an alkyl group, or $R^3$ and $R^4$ optionally form, together with the adjacent nitrogen atom, an optionally substituted nitrogen-containing heterocycle;

Y is a spacer selected from (1) a bond, (2) a divalent $C_{1-6}$ hydrocarbon group optionally having substituent(s), (3) —O—$(R^5)_m$—$(R^6)_n$— wherein $R^5$ is a divalent $C_{1-6}$ hydrocarbon group optionally having substituent(s), $R^6$ is an oxygen atom, —S(O)$_w$— wherein w is 0, 1 or 2, or

wherein $R^7$ is a hydrogen atom, an optionally substituted hydrocarbon group, an optionally substituted $C_{1-6}$ alkyl-carbonyl or an optionally substituted $C_{1-6}$ alkylsulfonyl, m is 0 or 1, n is 0 or 1, (4)

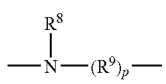

wherein $R^8$ is a hydrogen atom, an optionally substituted hydrocarbon group, an optionally substituted $C_{1-6}$ alkyl-carbonyl or an optionally substituted $C_{1-6}$ alkylsulfonyl, $R^9$ is a divalent $C_{1-6}$ hydrocarbon group optionally having substituent(s), p is 0 or 1, (5) —S(O)$_q$— wherein q is 0 or 1, and (6) —S(O)$_r$—$R^{10}$— wherein $R^{10}$ is a divalent $C_{1-6}$ hydrocarbon group optionally having substituent(s), an oxygen atom or

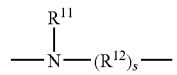

wherein $R^{11}$ is a hydrogen atom, an optionally substituted hydrocarbon group, an optionally substituted $C_{1-6}$ alkyl-carbonyl or an optionally substituted $C_{1-6}$ alkylsulfonyl, $R^{12}$ is a divalent $C_{1-6}$ hydrocarbon group optionally having substituent(s) or —SO$_2$—, s is 0 or 1, r is 0, 1 or 2, or a salt thereof, excluding one wherein a cyclic group for $R^2$ has an aminosulfonyl group as a substituent, N-methyl-1-[1-phenyl-2-(phenylthio)-1H-imidazol-4-yl]methanamine and 1-[4-phenyl-5-(phenylthio)-1,3-thiazol-2-yl]methanamine,

[2] a compound represented by the formula (I)

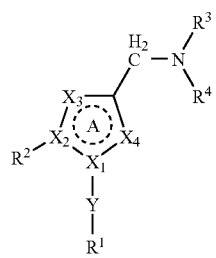
(I)

wherein ring A is a saturated or unsaturated 5-membered heterocycle containing, as a ring-constituting atom besides carbon atoms, at least one heteroatom selected from a nitrogen atom, an oxygen atom and a sulfur atom, the ring-constituting atoms $X_1$ and $X_2$ are the same or different and each is a carbon atom or a nitrogen atom, the ring-constituting atoms $X_3$ and $X_4$ are the same or different and each is a carbon atom, a nitrogen atom, an oxygen atom or a sulfur atom (provided that a pyrrole ring wherein $X_1$ is a nitrogen atom is excluded from ring A), and when the ring-constituting atom $X_3$ or $X_4$ is a carbon atom or a nitrogen atom, each ring-constituting atom optionally has substituent(s) selected from an optionally substituted alkyl group, an acyl group, an optionally substituted hydroxy group, an optionally substituted mercapto group, an optionally substituted amino group, a halogen atom, a cyano group and a nitro group;

$R^1$ and $R^2$ are the same or different and each is a cyclic group optionally having substituent(s);

$R^3$ and $R^4$ are the same or different and each is a hydrogen atom or an alkyl group;

Y is a spacer selected from (1) a bond, (2) a divalent $C_{1-6}$ hydrocarbon group optionally having substituent(s), (3) —O—$(R^5)_m$—$(R^6)_n$— wherein $R^5$ is a divalent $C_{1-6}$ hydrocarbon group optionally having substituent(s), $R^6$ is an oxygen atom, a sulfur atom or

wherein $R^7$ is a hydrogen atom, an optionally substituted hydrocarbon group, an optionally substituted $C_{1-6}$ alkyl-carbonyl or an optionally substituted $C_{1-6}$ alkylsulfonyl, m is 0 or 1, n is 0 or 1, (4)

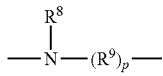

wherein $R^8$ is a hydrogen atom, an optionally substituted hydrocarbon group, an optionally substituted $C_{1-6}$ alkyl-carbonyl or an optionally substituted $C_{1-6}$ alkylsulfonyl, $R^9$ is a divalent $C_{1-6}$ hydrocarbon group optionally having substituent(s), p is 0 or 1, (5) —S(O)$_q$— wherein q is 0 or 1, and (6) —S(O)$_r$—R$^{10}$— wherein $R^{10}$ is a divalent $C_{1-6}$ hydrocarbon group optionally having substituent(s), an oxygen atom or

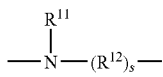

wherein $R^{11}$ is a hydrogen atom, an optionally substituted hydrocarbon group, an optionally substituted $C_{1-6}$ alkyl-carbonyl or an optionally substituted $C_{1-6}$ alkylsulfonyl, $R^{12}$ is a divalent $C_{1-6}$ hydrocarbon group optionally having substituent(s) or —SO$_2$—, s is 0 or 1, r is 0, 1 or 2, excluding one wherein a cyclic group for $R^2$ has an aminosulfonyl group as a substituent, N-methyl-1-[1-phenyl-2-(phenylthio)-1H-imidazol-4-yl]methanamine and 1-[4-phenyl-5-(phenylthio)-1,3-thiazol-2-yl]methanamine, or a salt thereof,

[3] the compound of the above-mentioned [1], wherein $R^3$ and $R^4$ are each a hydrogen atom or an alkyl group, or a salt thereof,

[4] the compound of the above-mentioned [1] or [2], wherein the partial structure of the formula (I)

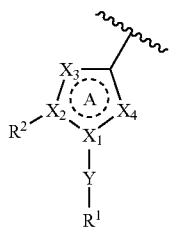

is

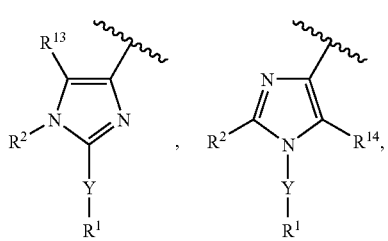

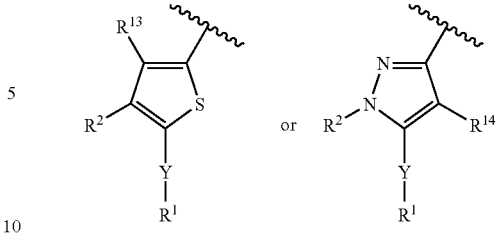

wherein $R^{13}$ and $R^{14}$ are the same or different and each is a hydrogen atom, an optionally substituted alkyl group, an acyl group, an optionally substituted hydroxy group, an optionally substituted mercapto group, an optionally substituted amino group, a halogen atom, a cyano group or a nitro group, and other symbols are as defined in the above-mentioned [1], or a salt thereof,

[5] the compound of the above-mentioned [1] or [2], wherein the substituent which a carbon atom optionally has is a halogen atom when $X_3$ or $X_4$ is a carbon atom, or a salt thereof,

[6] the compound of the above-mentioned [1] or [2], wherein Y is a spacer selected from (1) a bond, (2) a methylene group optionally having substituent(s), (3) —O—, (4) —S(O)$_q$— wherein q is 0 or 1, and (5) —S(O)$_r$—R$^{10}$— wherein $R^{10}$ is a methylene group optionally having substituent(s), r is 0, 1 or 2, or a salt thereof,

[7] the compound of the above-mentioned [1] or [2], wherein $R^2$ is a group represented by

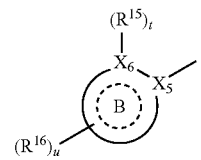

wherein ring B is a cyclic group having $X_5$ and $X_6$ as ring-constituting atoms, $X_5$ is a carbon atom or a nitrogen atom, $X_6$ is a carbon atom, a nitrogen atom, an oxygen atom or a sulfur atom;

$R^{15}$ is a substituent that $X_6$ optionally has when $X_6$ is a carbon atom or a nitrogen atom;

$R^{16}$ is an optionally substituted alkyl group, an acyl group, an optionally substituted hydroxy group, an optionally substituted mercapto group, an optionally substituted amino group, a halogen atom, a cyano group or a nitro group;

t is 0 or 1; and u is an integer of 0 to 3, or a salt thereof,

[8] 1-[1-(4-fluorobenzyl)-2-phenyl-1H-imidazol-4-yl]-N-methylmethanamine or a salt thereof,

[9] 1-[5-chloro-1-(4-fluorobenzyl)-2-phenyl-1H-imidazol-4-yl]-N-methylmethanamine or a salt thereof,

[10] 1-{4-(2-fluorophenyl)-5-[(3-methoxyphenyl)thio]-2-thienyl}-N-methylmethanamine or a salt thereof,

[11] 1-{4-(2-fluorophenyl)-5-[(3-methoxyphenyl)sulfinyl]-2-thienyl}-N-methylmethanamine or a salt thereof,

[12] 1-{4-(2-fluoropyridin-3-yl)-5-[(1,3-thiazol-2-yl)thio]thiophen-2-yl}-N-methylmethanamine or a salt thereof,

[13] 1-{4-(2-fluoropyridin-3-yl)-5-[(2-methylfuran-3-yl)thio]thiophen-2-yl}-N-methylmethanamine or a salt thereof,

[14] 1-{1-(2-chlorophenyl)-5-[(6-chloropyridin-3-yl)thio]-1H-pyrazol-3-yl}-N-methylmethanamine or a salt thereof,
[15] a prodrug of the compound of the above-mentioned [1] or [2] or a salt thereof,
[16] a medicament comprising a compound represented by the formula (I)

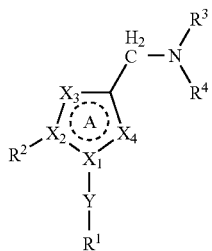
(I)

wherein
ring A is a saturated or unsaturated 5-membered heterocycle containing, as a ring-constituting atom besides carbon atoms, at least one heteroatom selected from a nitrogen atom, an oxygen atom and a sulfur atom, the ring-constituting atoms $X_1$ and $X_2$ are the same or different and each is a carbon atom or a nitrogen atom, the ring-constituting atoms $X_3$ and $X_4$ are the same or different and each is a carbon atom, a nitrogen atom, an oxygen atom or a sulfur atom (provided that a pyrrole ring wherein $X_1$ is a nitrogen atom is excluded from ring A), and when the ring-constituting atom $X_3$ or $X_4$ is a carbon atom or a nitrogen atom, each ring-constituting atom optionally has substituent(s) selected from an optionally substituted alkyl group, an acyl group, an optionally substituted hydroxy group, an optionally substituted mercapto group, an optionally substituted amino group, a halogen atom, a cyano group and a nitro group;
$R^1$ and $R^2$ are the same or different and each is a cyclic group optionally having substituent(s);
$R^3$ and $R^4$ are the same or different and each is a hydrogen atom or an alkyl group, or $R^3$ and $R^4$ optionally form, together with the adjacent nitrogen atom, an optionally substituted nitrogen-containing heterocycle;
Y is a spacer selected from,
(1) a bond,
(2) a divalent $C_{1-6}$ hydrocarbon group optionally having substituent(s),
(3) —O—$(R^5)_m$—$(R^6)_n$— wherein $R^5$ is a divalent $C_{1-6}$ hydrocarbon group optionally having substituent(s), $R^6$ is an oxygen atom, —S(O)$_w$- wherein w is 0, 1 or 2, or

wherein $R^7$ is a hydrogen atom, an optionally substituted hydrocarbon group, an optionally substituted $C_{1-6}$ alkyl-carbonyl or an optionally substituted $C_{1-6}$ alkylsulfonyl, m is 0 or 1, n is 0 or 1,
(4)

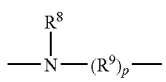

wherein $R^8$ is a hydrogen atom, an optionally substituted hydrocarbon group, an optionally substituted $C_{1-6}$ alkyl-carbonyl or an optionally substituted $C_{1-6}$ alkylsulfonyl, $R^9$ is a divalent $C_{1-6}$ hydrocarbon group optionally having substituent(s),
p is 0 or 1,
(5) —S(O)$_q$— wherein q is 0 or 1, and
(6) —S(O)$_r$—$R^{10}$— wherein $R^{10}$ is a divalent $C_{1-6}$ hydrocarbon group optionally having substituent(s), an oxygen atom or

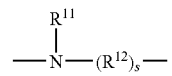

wherein $R^{11}$ is a hydrogen atom, an optionally substituted hydrocarbon group, an optionally substituted $C_{1-6}$ alkyl-carbonyl or an optionally substituted $C_{1-6}$ alkylsulfonyl, $R^{12}$ is a divalent $C_{1-6}$ hydrocarbon group optionally having substituent(s) or —SO$_2$—, s is 0 or 1, and r is 0, 1 or 2 or a salt thereof or a prodrug thereof,
[17] the medicament of the above-mentioned [16], which is an acid secretion inhibitor,
[18] the medicament of the above-mentioned [16], which is a potassium-competitive acid blocker,
[19] the medicament of the above-mentioned [16], which is an agent for the treatment or prophylaxis of peptic ulcer, Zollinger-Ellison syndrome, gastritis, reflux esophagitis, Symptomatic Gastroesophageal Reflux Disease (Symptomatic GERD), Barrett's esophagus, Functional Dyspepsia, gastric cancer, stomach MALT lymphoma, ulcer caused by non-steroidal anti-inflammatory agent, or hyperacidity or ulcer due to postoperative stress; or a suppressant of upper gastrointestinal hemorrhage due to peptic ulcer, acute stress ulcer, hemorrhagic gastritis or invasive stress,
[20] a method for the treatment or prophylaxis of peptic ulcer, Zollinger-Ellison syndrome, gastritis, reflux esophagitis, Symptomatic Gastroesophageal Reflux Disease (Symptomatic GERD), Barrett's esophagus, Functional Dyspepsia, gastric cancer, stomach MALT lymphoma, ulcer caused by non-steroidal anti-inflammatory agent or hyperacidity or ulcer due to postoperative stress; or a method for suppressing upper gastrointestinal hemorrhage due to peptic ulcer, acute stress ulcer, hemorrhagic gastritis or invasive stress in a mammal, comprising administering an effective amount of a compound represented by the formula (I)

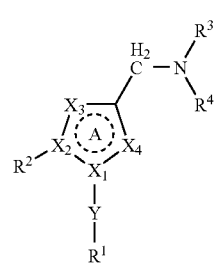
(I)

wherein
ring A is a saturated or unsaturated 5-membered heterocycle containing, as a ring-constituting atom besides carbon atoms, at least one heteroatom selected from a nitrogen atom, an oxygen atom and a sulfur atom, the ring-constituting atoms $X_1$ and $X_2$ are the same or different and each is a carbon atom or a nitrogen atom, the ring-constituting atoms $X_3$ and $X_4$ are the same or different and each is a carbon atom, a nitrogen atom, an oxygen atom or a sulfur atom (provided that a pyrrole ring wherein $X_1$ is a nitrogen atom is excluded from ring A), and when the ring-constituting atom $X_3$ or $X_4$ is a carbon atom or a nitrogen atom, each ring-constituting atom optionally has substituent(s) selected from an optionally substituted alkyl group, an acyl group, an optionally substituted hydroxy group, an optionally substituted mercapto group, an optionally substituted amino group, a halogen atom, a cyano group and a nitro group;

$R^1$ and $R^2$ are the same or different and each is a cyclic group optionally having substituent(s);

$R^3$ and $R^4$ are the same or different and each is a hydrogen atom or an alkyl group, or $R^3$ and $R^4$ optionally form, together with the adjacent nitrogen atom, an optionally substituted nitrogen-containing heterocycle;

Y is a spacer selected from, (1) a bond, (2) a divalent $C_{1-6}$ hydrocarbon group optionally having substituent(s), (3) —O—$(R^5)_m$—$(R^6)_n$— wherein $R^5$ is a divalent $C_{1-6}$ hydrocarbon group optionally having substituent(s), $R^6$ is an oxygen atom, —S(O)$_w$— wherein w is 0, 1 or 2, or

wherein $R^7$ is a hydrogen atom, an optionally substituted hydrocarbon group, an optionally substituted $C_{1-6}$ alkyl-carbonyl or an optionally substituted $C_{1-6}$ alkylsulfonyl, m is 0 or 1, n is 0 or 1, (4)

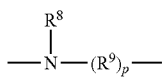

wherein $R^8$ is a hydrogen atom, an optionally substituted hydrocarbon group, an optionally substituted $C_{1-6}$ alkyl-carbonyl or an optionally substituted $C_{1-6}$ alkylsulfonyl, $R^9$ is a divalent $C_{1-6}$ hydrocarbon group optionally having substituent(s), p is 0 or 1, (5) —S(O)$_q$- wherein q is 0 or 1, and (6) —S(O)$_r$—$R^{10}$— wherein $R^{10}$ is a divalent $C_{1-6}$ hydrocarbon group optionally having substituent(s), an oxygen atom or

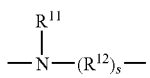

wherein $R^{11}$ is a hydrogen atom, an optionally substituted hydrocarbon group, an optionally substituted $C_{1-6}$ alkyl-carbonyl or an optionally substituted $C_{1-6}$ alkylsulfonyl, $R^{12}$ is a divalent $C_{1-6}$ hydrocarbon group optionally having substituent(s) or —SO$_2$—, s is 0 or 1, r is 0, 1 or 2 or a salt thereof or a prodrug thereof to the mammal, and

[21] use of a compound represented by the formula (I)

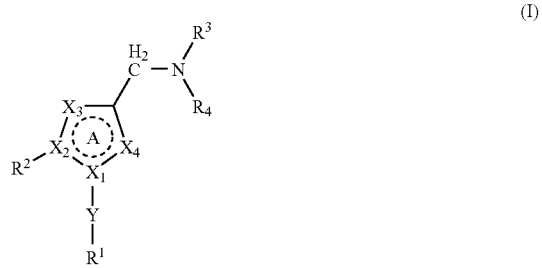

wherein
ring A is a saturated or unsaturated 5-membered heterocycle containing, as a ring-constituting atom besides carbon atoms, at least one heteroatom selected from a nitrogen atom, an oxygen atom and a sulfur atom, the ring-constituting atoms $X_1$ and $X_2$ are the same or different and each is a carbon atom or a nitrogen atom, the ring-constituting atoms $X_3$ and $X_4$ are the same or different and each is a carbon atom, a nitrogen atom, an oxygen atom or a sulfur atom (provided that a pyrrole ring wherein $X_1$ is a nitrogen atom is excluded from ring A), and when the ring-constituting atom $X_3$ or $X_4$ is a carbon atom or a nitrogen atom, each ring-constituting atom optionally has substituent(s) selected from an optionally substituted alkyl group, an acyl group, an optionally substituted hydroxy group, an optionally substituted mercapto group, an optionally substituted amino group, a halogen atom, a cyano group and a nitro group;

$R^1$ and $R^2$ are the same or different and each is a cyclic group optionally having substituent(s);

$R^3$ and $R^4$ are the same or different and each is a hydrogen atom or an alkyl group, or $R^3$ and $R^4$ optionally form, together with the adjacent nitrogen atom, an optionally substituted nitrogen-containing heterocycle;

Y is a spacer selected from, (1) a bond, (2) a divalent $C_{1-6}$ hydrocarbon group optionally having substituent(s), (3) —O—$(R^5)_m$—$(R^6)_n$— wherein $R^5$ is a divalent $C_{1-6}$ hydrocarbon group optionally having substituent(s), $R^6$ is an oxygen atom, —S(O)$_w$— wherein w is 0, 1 or 2, or

wherein $R^7$ is a hydrogen atom, an optionally substituted hydrocarbon group, an optionally substituted $C_{1-6}$ alkyl-carbonyl or an optionally substituted $C_{1-6}$ alkylsulfonyl, m is 0 or 1, n is 0 or 1, (4)

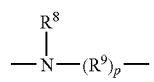

wherein R⁸ is a hydrogen atom, an optionally substituted hydrocarbon group, an optionally substituted $C_{1-6}$ alkyl-carbonyl or an optionally substituted $C_{1-6}$ alkylsulfonyl, R⁹ is a divalent $C_{1-6}$ hydrocarbon group optionally having substituent(s),
p is 0 or 1,
(5) —S(O)$_q$— wherein q is 0 or 1, and
(6) —S(O)$_r$—R¹⁰— wherein R¹⁰ is a divalent $C_{1-6}$ hydrocarbon group optionally having substituent(s), an oxygen atom or

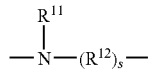

wherein R¹¹ is a hydrogen atom, an optionally substituted hydrocarbon group, an optionally substituted $C_{1-6}$ alkyl-carbonyl or an optionally substituted $C_{1-6}$ alkylsulfonyl, R¹² is a divalent $C_{1-6}$ hydrocarbon group optionally having substituent(s) or —SO₂—, s is 0 or 1, r is 0, 1 or 2 or a salt thereof or a prodrug thereof, for the production of an agent for the treatment or prophylaxis of peptic ulcer, Zollinger-Ellison syndrome, gastritis, reflux esophagitis, Symptomatic Gastroesophageal Reflux Disease (Symptomatic GERD), Barrett's esophagus, Functional Dyspepsia, gastric cancer, stomach MALT lymphoma, ulcer caused by non-steroidal anti-inflammatory agent or hyperacidity or ulcer due to postoperative stress; or a suppressant of upper gastrointestinal hemorrhage due to peptic ulcer, acute stress ulcer, hemorrhagic gastritis or invasive stress.

Effect of the Invention

Compound (I) of the present invention shows a superior proton pump inhibitory effect. Conventional proton pump inhibitors such as omeprazole, lansoprazole and the like are converted to active forms in an acidic environment of stomach parietal cells and form a covalent bond with a cysteine residue of H'/K'-ATPase, and irreversibly inhibit the enzyme activity. In contrast, compound (I) inhibits proton pump (H'/K'-ATPase) activity in a reversible and K' competitive inhibitory manner, and consequently suppresses acid secretion. Therefore, it is sometimes called a potassium-competitive acid blocker (P-CAB), or an acid pump antagonist (APA). Compound (I) rapidly exhibits the action and shows the maximum efficacy from the initial administration. Furthermore, it characteristically shows less influence of metabolic polymorphism (variation between patients) and long duration of action. Accordingly, the present invention can provide a clinically useful agent for the prophylaxis or treatment of peptic ulcer (e.g., gastric ulcer, duodenal ulcer, anastomotic ulcer, ulcer caused by non-steroidal anti-inflammatory agent, ulcer due to postoperative stress etc.), Zollinger-Ellison syndrome, gastritis, erosive esophagitis, reflux esophagitis, symptomatic gastroesophageal reflux disease (Symptomatic GERD), Barrett's esophagus, functional dyspepsia, gastric cancer, stomach MALT lymphoma or hyperacidity; or a suppressant of upper gastrointestinal hemorrhage due to peptic ulcer, acute stress ulcer, hemorrhagic gastritis or invasive stress; and the like. Since compound (I) shows low toxicity and is superior in water-solubility, in vivo kinetics and efficacy expression, it is useful as a pharmaceutical composition. Since compound (I) is stable even under acidic conditions, it can be administered orally as a conventional tablet and the like without formulating into an enteric-coated preparation. This has an advantageous consequence that the preparation (tablet and the like) can be made smaller, and can be easily swallowed by patients having difficulty in swallowing, particularly the elderly and children. In addition, since it is free of a sustained release effect afforded by enteric-coated preparations, onset of inhibitory action on gastric acid secretion is rapid, and symptoms such as pain and the like can be alleviated rapidly.

DETAILED DESCRIPTION OF THE INVENTION

In the formula (I), ring A is a saturated or unsaturated 5-membered heterocycle containing, as a ring-constituting atom besides carbon atoms, at least one heteroatom selected from a nitrogen atom, an oxygen atom and a sulfur atom. Specific examples of ring A include a thiophene ring, a furan ring, a pyrrole ring, an imidazole ring, a pyrazole ring, an isothiazole ring, a thiazole ring, an isoxazole ring, an oxazole ring, an oxazoline ring (e.g., an 2-oxazoline ring, an 3-oxazoline ring, an 4-oxazoline ring), an oxazolidine ring, a thiazoline ring, a thiazolidine ring, a pyrrolidine ring, a pyrroline ring, an imidazolidine ring, an imidazoline ring, a pyrazolidine ring, a pyrazoline ring, a furazan ring, an oxadiazole ring (e.g., an 1,2,3-oxadiazole ring, an 1,2,4-oxadiazole ring, an 1,3,4-oxadiazole ring), an oxadiazoline ring (e.g., 1,2,3-oxadiazoline ring, 1,2,4-oxadiazoline ring, 1,3,4-oxadiazoline ring), oxadiazolidine ring (e.g., 1,2,3-oxadiazolidine ring, 1,2,4-oxadiazolidine ring, 1,3,4-oxadiazolidine ring), a thiadiazole ring (e.g., a 1,2,3-thiadiazole ring, a 1,2,4-thiadiazole ring, a 1,3,4-thiadiazole ring), a thiadiazoline ring, a thiadiazolidine ring (e.g., a 1,3,4-thiadiazolidine ring), a triazole ring (e.g., a 1,2,3-triazole ring, a 1,2,4-triazole ring), triazolidine ring (e.g., 1,2,3-triazolidine ring, 1,2,4-triazolidine ring), triazoline ring (e.g., 1,2,3-triazoline ring, 1,2,4-triazoline ring), a tetrazole ring, a tetrahydrofuran ring and the like.

Here, the ring-constituting atom (X₁) of ring A to which a group represented by —Y—R¹ is bonded, and the ring-constituting atom (X₂) of ring A to which R² is bonded are the same or different and each is a carbon atom or a nitrogen atom.

The ring-constituting atom X₃ and X₄ of ring A are the same or different and each is a carbon atom, a nitrogen atom, an oxygen atom or a sulfur atom.

When the ring-constituting atom X₃ or X₄ is a carbon atom or a nitrogen atom, each ring-constituting atom optionally has a substituent selected from an optionally substituted alkyl group, an acyl group, an optionally substituted hydroxy group, an optionally substituted mercapto group, an optionally substituted amino group, a halogen atom, a cyano group and a nitro group. Here, when a group on the ring-constituting atom X₃ is represented by R¹³, and a group on the ring-constituting atom X₄ is represented by R¹⁴, compound (I) can be represented as a compound represented by

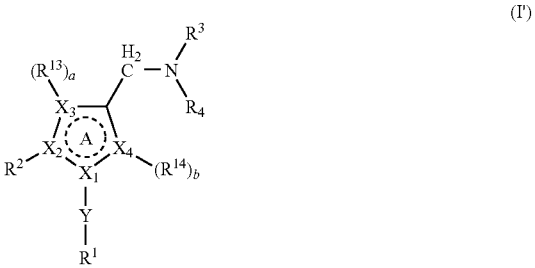

wherein R¹³ and R¹⁴ are the same or different and each is a hydrogen atom, an optionally substituted alkyl group, an acyl group, an optionally substituted hydroxy group, an optionally substituted mercapto group, an optionally substituted amino group, a halogen atom, a cyano group or a nitro group, a is 0 to 2, b is 0 to 2, and other symbols are as defined above, and when two $R^{13}$ or $R^{14}$ are present, they may be the same or different,
or a salt thereof (hereinafter sometimes to be referred to as compound (I')).

Regarding ring A, a pyrrole ring wherein $X_1$ is a nitrogen atom is excluded from ring A.

That is, compound (I) or compound (I') does not encompass a compound represented by the formula:

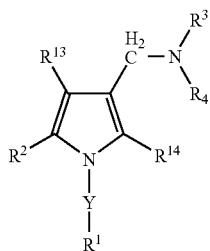

wherein each symbol is as defined above.

Examples of the alkyl group of the "optionally substituted alkyl group" for $R^{13}$ or $R^{14}$ or the alkyl group of the "optionally substituted alkyl group" which each ring-constituting atom $X_3$ or $X_4$ may have when it is a carbon atom or a nitrogen atom include a $C_{1-6}$ alkyl group such as methyl, ethyl, n-propyl, isopropyl, n-butyl, isobutyl, sec-butyl, tert-butyl, n-pentyl, sec-pentyl, isopentyl, neopentyl, n-hexyl, isohexyl and the like.

Examples of the substituent of the alkyl group include (1) a halogen atom (e.g., a fluorine atom, a chlorine atom, a bromine atom, an iodine atom), (2) nitro, (3) cyano, (4) hydroxy, (5) $C_{1-6}$ alkoxy optionally having 1 to 3 halogen atoms s (e.g., a fluorine atom, a chlorine atom, a bromine atom, an iodine atom) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 3 halogen atoms s (e.g., a fluorine atom, a chlorine atom, a bromine atom, an iodine atom) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl, etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino optionally containing, besides carbon atoms and one nitrogen atom, 1 or 2 kinds of 1 to 4 heteroatoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atoms, 1 or 2 kinds of 1 to 4 heteroatoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.).

The number of the substituents is 1 to 3.

Examples of the "acyl group" for $R^{13}$ or $R^{14}$ or the "acyl group" which each ring-constituting atom $X_3$ or $X_4$ may have when it is a carbon atom or a nitrogen atom include an acyl group having a carbon number of 1 to 20 induced from organic carboxylic acid. For example, a $C_{1-7}$ alkanoyl group (e.g., formyl; $C_{1-6}$ alkyl-carbonyl such as acetyl, propionyl, butyryl, isobutyryl, pentanoyl, hexanoyl, heptanoyl etc. and the like), a $C_{6-14}$ aryl-carbonyl group (e.g., benzoyl, naphthalenecarbonyl etc.), a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl etc.), a $C_{6-14}$ aryloxy-carbonyl group (e.g., phenoxycarbonyl etc.), a $C_{7-19}$ aralkyl-carbonyl group (e.g., phenyl-$C_{1-4}$ alkyl-carbonyl such as benzylcarbonyl, phenethylcarbonyl, phenylpropylcarbonyl etc.; benzhydrylcarbonyl; naphthyl-$C_{1-4}$ alkyl-carbonyl such as naphthylethylcarbonyl etc. and the like), a $C_{7-19}$ aralkyloxy-carbonyl group (e.g., phenyl-$C_{1-4}$ alkyloxy-carbonyl such as benzyloxycarbonyl etc. and the like), a 5- or 6-membered heterocyclyl-carbonyl group or a condensed heterocyclyl-carbonyl group thereof (e.g., pyrrolylcarbonyl such as 2- or 3-pyrrolylcarbonyl etc.; pyrazolylcarbonyl such as 3-, 4- or 5-pyrazolylcarbonyl etc.; imidazolylcarbonyl such as 2-, 4- or 5-imidazolylcarbonyl etc.; triazolylcarbonyl such as 1,2,3-triazol-4-ylcarbonyl, 1,2,4-triazol-3-ylcarbonyl etc.; tetrazolylcarbonyl such as 1H- or 2H-tetrazol-5-ylcarbonyl etc.; furylcarbonyl such as 2- or 3-furylcarbonyl etc.; thienylcarbonyl such as 2- or 3-thienylcarbonyl etc.; oxazolylcarbonyl such as 2-, 4- or 5-oxazolylcarbonyl etc.; isoxazolylcarbonyl such as 3-, 4- or 5-isoxazolylcarbonyl etc.; oxadiazolylcarbonyl such as 1,2,3-oxadiazol-4- or 5-ylcarbonyl, 1,2,4-oxadiazol-3- or 5-ylcarbonyl, 1,2,5-oxadiazol-3- or 4-ylcarbonyl, 1,3,4-oxadiazol-2-ylcarbonyl etc.; thiazolylcarbonyl such as 2-, 4- or 5-thiazolylcarbonyl etc.; isothiazolylcarbonyl such as 3-, 4- or 5-isothiazolylcarbonyl etc.; thiadiazolylcarbonyl such as 1,2,3-thiadiazol-4- or 5-ylcarbonyl, 1,2,4-thiadiazol-3- or 5-ylcarbonyl, 1,2,5-thiadiazol-3- or 4-ylcarbonyl, 1,3,4-thiadiazol-2-ylcarbonyl etc.; pyrrolidinylcarbonyl such as 2- or 3-pyrrolidinylcarbonyl etc.; pyridylcarbonyl such as 2-, 3- or 4-pyridylcarbonyl etc.; pyridylcarbonyl which a nitrogen atom is oxidized such as 2-, 3- or 4-pyridyl-N-oxidocarbonyl etc.; pyridazinylcarbonyl such as 3- or 4-pyridazinylcarbonyl etc.; pyridazinylcarbonyl wherein one or both nitrogen atoms are oxidized such as 3-, 4-, 5- or 6-pyridazinyl-N-oxidocarbonyl and the like; pyrimidinylcarbonyl such as 2-, 4- or 5-pyrimidinylcarbonyl etc.; pyrimidinylcarbonyl wherein one or both nitrogen atoms are oxidized such as 2-, 4-, 5- or 6-pyrimidinyl-N-oxidocarbonyl and the like; pyrazinylcarbonyl; piperidylcarbonyl such as 2-, 3- or 4-piperidylcarbonyl etc.; piperazinylcarbonyl; indolylcarbonyl such as 3H-indol-2- or 3-ylcarbonyl etc.; pyranylcarbonyl such as 2-, 3- or 4-pyranylcarbonyl etc.; thiopyranylcarbonyl such as 2-, 3- or 4-thiopyranylcarbonyl etc.; quinolylcarbonyl such as 3-, 4-, 5-, 6-, 7- or 8-quinolylcarbonyl etc.; isoquinolylcarbonyl; pyrido[2,3-d]pyrimidinylcarbonyl (e.g., pyrido[2,3-d]pyrimidin-2-ylcarbonyl); naphthyridinylcarbonyl (e.g., 1,5-naphthyridin-2- or 3-ylcarbonyl) such as 1,5-, 1,6-, 1,7-, 1,8-, 2,6- or 2,7-naphthyridinylcarbonyl etc.; thieno[2,3-d]pyridylcarbonyl (e.g., thieno[2,3-d]pyridin-3-ylcarbonyl); pyrazinoquinolylcarbonyl (e.g., pyrazino[2,3-b]quinolin-2-ylcarbonyl); a 5- or 6-membered heterocyclyl-carbonyl group containing 1 to 4 hetero atoms such as nitrogen atom (optionally oxidized), oxygen atom, sulfur atom (mono- or di-oxidized) and the like, for example, chromenylcarbonyl (e.g., 2H-chromen-2- or 3-ylcarbonyl etc.) and the like), a 5- or 6-membered heterocyclyl-acetyl group (for example, a 5- or 6-membered heterocyclyl-acetyl group containing 1 to 4 hetero atoms selected from nitrogen atom (optionally oxidized), oxygen atom, sulfur atom (optionally mono- or di-oxidized) and the like (e.g., 2-pyrrolylacetyl, 3-imidazolylacetyl, 5-isooxazolylacetyl and the like)) and the like can be used.

As for the substituent of the acyl group, for example, when the above-mentioned acyl group is a $C_{1-7}$ alkanoyl group or a $C_{1-6}$ alkoxy-carbonyl group, it may be substituted by 1 to 3 substituents selected from an alkylthio group (e.g., $C_{1-4}$ alkylthio such as methylthio, ethylthio, n-propylthio, isopropylthio etc. and the like), a halogen atom (e.g., a fluorine atom, a chlorine atom, a bromine atom, an iodine atom), an alkoxy group (e.g., $C_{1-6}$ alkoxy such as methoxy, ethoxy, n-propoxy, tert-butoxy, n-hexyloxy etc. and the like), a nitro group, an alkoxy-carbonyl group (e.g., $C_{1-6}$ alkoxy-carbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl etc. and the like), an alkylamino group (e.g., mono- or di-$C_{1-6}$ alkylamino such as methylamino, ethylamino, n-propylamino, n-butylamino, tert-butylamino, n-pentylamino, n-hexylamino, dimethylamino, diethylamino, methylethylamino, di-(n-propyl) amino, di-(n-butyl)amino and the like etc.), an alkoxyimino group (e.g., $C_{1-6}$ alkoxyimino such as methoxyimino, ethoxyimino, n-propoxyimino, tert-butoxyimino, n-hexyloxyimino etc. and the like) and hydroxyimino.

In addition, when the above-mentioned acyl group is a $C_{6-14}$ aryl-carbonyl group, a $C_{6-14}$ aryloxy-carbonyl group, a $C_{7-19}$ aralkyl-carbonyl group, a $C_{7-19}$ aralkyloxy-carbonyl group, a 5- or 6-membered heterocyclyl-carbonyl group or a condensed heterocyclyl-carbonyl group thereof or a 5- or 6-membered heterocyclyl-acetyl group, it may be substituted by 1 to 5 (preferably 1 to 3) substituents selected from an alkyl group (e.g., $C_{1-6}$ alkyl such as methyl, ethyl, n-propyl, isopropyl, n-butyl, isobutyl, sec-butyl, tert-butyl, n-pentyl, sec-pentyl, isopentyl, neopentyl, n-hexyl, isohexyl etc. and the like), a cycloalkyl group (e.g., $C_{3-6}$ cycloalkyl such as cyclopropyl, cyclobutyl, cyclopentyl, cyclohexyl etc. and the like), an alkenyl group (e.g., $C_{2-6}$ alkenyl such as allyl, isopropenyl, isobutenyl, 1-methylallyl, 2-pentenyl, 2-hexenyl etc. and the like), an alkynyl group (e.g., $C_{2-6}$ alkynyl such as propargyl, 2-butynyl, 3-butynyl, 3-pentynyl, 3-hexynyl etc. and the like), an alkoxy group (e.g., $C_{1-6}$ alkoxy such as methoxy, ethoxy, n-propoxy, tert-butoxy, n-hexyloxy etc. and the like), an acyl group [e.g., $C_{1-7}$ alkanoyl such as formyl, acetyl, propionyl, butyryl, isobutyryl, pentanoyl, hexanoyl, heptanoyl etc.; $C_{6-14}$ aryl-carbonyl such as benzoyl, naphthalenecarbonyl etc.; $C_{1-6}$ alkoxy-carbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl etc.; $C_{6-14}$ aryloxy-carbonyl such as phenoxycarbonyl etc.; $C_{2-19}$ aralkyl-carbonyl such as phenyl-$C_{1-4}$ alkyl-carbonyl (e.g., benzylcarbonyl, phenethylcarbonyl, phenylpropylcarbonyl etc.) and the like; $C_{7-19}$ aralkyloxy-carbonyl such as phenyl-$C_{1-4}$ alkyloxy-carbonyl (e.g., benzyloxycarbonyl etc.) etc. and the like], nitro, amino, hydroxy, cyano, sulfamoyl, mercapto, a halogen atom (e.g., a fluorine atom, a chlorine atom, a bromine atom, an iodine atom) and an alkylthio group (e.g., $C_{1-4}$ alkylthio such as methylthio, ethylthio, n-propylthio, isobutylthio etc. and the like).

Examples of the "optionally substituted hydroxy group" for $R^{13}$ or $R^{14}$ or the "optionally substituted hydroxy group" that each ring-constituting atom $X_3$ or $X_4$ may have when it is a carbon atom or a nitrogen atom include a group represented by —$OR^{17}$ wherein $R^{17}$ is a hydrogen atom, an optionally substituted hydrocarbon group, an optionally substituted heterocyclic group or an acyl group.

Examples of the "hydrocarbon group" of the "optionally substituted hydrocarbon group" for $R^{17}$ include a chain or cyclic hydrocarbon group (e.g., alkyl, alkenyl, alkynyl, cycloalkyl, aryl, aralkyl etc.). Among these, a chain or cyclic hydrocarbon group having a carbon number of 1 to 16 and the like are preferable.

Examples of the above-mentioned "alkyl" include $C_{1-6}$ alkyl (e.g., methyl, ethyl, propyl, isopropyl, butyl, isobutyl, sec-butyl, tert-butyl, pentyl, hexyl etc.) and the like.

Examples of the above-mentioned "alkenyl" include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl etc.) and the like.

Examples of the above-mentioned "alkynyl" include $C_{2-6}$ alkynyl (e.g., ethynyl, propargyl, 1-butynyl, 2-butynyl, 3-butynyl, 1-hexynyl etc.) and the like.

Examples of the above-mentioned "cycloalkyl" include $C_{3-7}$ cycloalkyl (e.g., cyclopropyl, cyclobutyl, cyclopentyl, cyclohexyl, cycloheptyl etc.) and the like.

Examples of the above-mentioned "aryl" include $C_{6-14}$ aryl (e.g., phenyl, 1-naphthyl, 2-naphthyl, 2-biphenylyl, 3-biphenylyl, 4-biphenylyl, 2-anthryl etc.) and the like.

Examples of the above-mentioned "aralkyl" include $C_{7-16}$ aralkyl (e.g., phenyl-$C_{1-6}$ alkyl such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl and the like, naphthyl-$C_{1-6}$ alkyl, diphenyl-$C_{1-4}$ alkyl etc.) and the like.

When the above-mentioned "hydrocarbon group" is alkyl, alkenyl or alkynyl, it may be substituted by 1 to 3 substituents selected from (1) a halogen atom (e.g., a fluorine atom, a chlorine atom, a bromine atom, an iodine atom), (2) nitro, (3) cyano, (4) hydroxy, (5) $C_{1-6}$ alkoxy optionally having 1 to 3 halogen atoms (e.g., a fluorine atom, a chlorine atom, a bromine atom, an iodine atom) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 3 halogen atoms (e.g., a fluorine atom, a chlorine atom, a bromine atom, an iodine atom) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) 5- to 7-membered saturated cyclic amino optionally containing, besides carbon atoms and a nitrogen atom, 1 or 2 kinds of 1 to 4 heteroatoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atoms, 1 or 2 kinds of 1 to 4 heteroatoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) oxo and the like.

In addition, when the above-mentioned "hydrocarbon group" is cycloalkyl, aryl or aralkyl, it may be substituted by 1 to 5 (preferably 1 to 3) substituents selected from (1) a halogen atom (e.g., a fluorine atom, a chlorine atom, a bromine atom, an iodine atom), (2) nitro, (3) cyano, (4) hydroxy, (5) $C_{1-6}$ alkoxy optionally having 1 to 3 halogen atoms (e.g., a fluorine atom, a chlorine atom, a bromine atom, an iodine atom) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 3 halogen atoms (e.g., a fluorine atom, a chlorine atom, a bromine atom, an iodine atom) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl optionally having 1 to 3 halogen atoms (e.g., a fluorine atom, a chlorine atom, a bromine atom, an iodine atom) (e.g., methylsulfonyl, ethylsulfonyl, trifluoromethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) 5- to 7-membered saturated cyclic amino optionally containing, besides carbon atoms and a nitrogen atom, 1 or 2 kinds of 1 to 4 heteroatoms selected from a nitrogen atom, a sulfur atom and an oxygen atom (e.g., pyrrolidin-l-yl, piperidino, piperazin-1-yl, morpholino, thiomorpholino, hexahydroazepin-1-yl etc.), (47) a 5- to 10-membered aromatic heterocyclic group containing, besides carbon atoms, 1 or 2 kinds of 1 to 4 heteroatoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) $C_{1-6}$ alkyl (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.) optionally having 1 to 3 halogen atoms (e.g., a fluorine atom, a chlorine atom, a bromine atom, an iodine atom) or a hydroxy group, (51) $C_{2-6}$ alkenyl (e.g., allyl, isopropenyl, isobutenyl, 1-methylallyl, 2-pentenyl, 2-hexenyl etc.) optionally having 1 to 3 halogen atoms (e.g., a fluorine atom, a chlorine atom, a bromine atom, an iodine atom), (52) $C_{2-6}$ alkynyl (e.g., propargyl, 2-butynyl, 3-butynyl, 3-pentynyl, 3-hexynyl etc.), (53) mono-$C_{3-7}$ cycloalkyl-carbamoyl (e.g., cyclopropylcarbamoyl, cyclobutylcarbamoyl etc.), (54) a 5- or 10-membered heterocyclyl-carbonyl containing, besides carbon atoms, 1 or 2 kinds of 1 to 4 heteroatoms selected from a nitrogen atom, a sulfur atom and an oxygen atom (e.g., 4-morpholinocarbonyl etc.), and the like.

Examples of the "heterocyclic group" of the "heterocyclic group optionally having substituent(s)" for $R^{17}$ include a 3- to 8-membered heterocyclic group (preferably a 5- or 6-membered heterocyclic group) containing, 1 to 4 heteroatoms selected from a nitrogen atom (optionally oxidized), an oxygen atom, a sulfur atom (optionally mono- or di-oxidized) and the like; and a group wherein a 3- or 8-membered heterocyclic group (preferably a 5- or 6-membered heterocyclic group) containing, 1 to 4 heteroatoms selected from a nitrogen atom (optionally oxidized), an oxygen atom, a sulfur atom (optionally mono- or di-oxidized) and the like is condensed with a benzene ring or a 3- to 8-membered heterocyclic group (preferably a 5- or 6-membered heterocyclic group) containing, 1 to 4 heteroatoms selected from a nitrogen atom (optionally oxidized), an oxygen atom, a sulfur atom (optionally mono- or di-oxidized) and the like, preferably a group wherein the 5- or 6-membered heterocyclic group is condensed with a 5- or 6-membered ring optionally containing, 1 to 4 heteroatoms selected from a nitrogen atom (optionally oxidized), an oxygen atom, a sulfur atom (optionally mono- or di-oxidized) and the like.

Specific examples thereof include aziridinyl (e.g., 1- or 2-aziridinyl), azirinyl (e.g., 1- or 2-azirinyl), azetyl (e.g., 2-, 3- or 4-azetyl), azetidinyl (e.g., 1-, 2- or 3-azetidinyl), perhydroazepinyl (e.g., 1-, 2-, 3- or 4-perhydroazepinyl), perhydroazocinyl (e.g., 1-, 2-, 3-, 4- or 5-perhydroazocinyl), pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5-imidazolyl), triazolyl (e.g., 1,2,3-triazol-1-, 4- or -5-yl, 1,2,4-triazol-1-, 3-, 4- or 5-yl), tetrazolyl (e.g., tetrazol-1-, 2- or 5-yl), furyl (e.g., 2- or 3-furyl), thienyl (e.g., 2- or 3-thienyl), thienyl wherein the sulfur atom is oxidized (e.g., 2- or 3-thienyl-1,1-dioxide), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), triazolyl (e.g., 2-, 4- or 5-thiazolyl), isothiazolyl (e.g., 3-, 4- or 5-isothiazolyl), thiadiazolyl (e.g., 1,2,3-thiadiazol-4- or 5-yl, 1,2,4-thiadiazol-3- or 5-yl, 1,2,5-thiadiazol-3-yl, 1,3,4-thiadiazol-2-yl), pyrrolidinyl (e.g., 1-, 2- or 3-pyrrolidinyl), pyridyl (e.g., 2-, 3- or 4-pyridyl), pyridyl wherein the nitrogen atom is oxidized (e.g., 2-, 3- or 4-pyridyl-N-oxide), pyridazinyl (e.g., 3- or 4-pyridazinyl), pyridazinyl wherein one or both of the nitrogen atoms are oxidized (e.g., 3-, 4-, 5- or 6-pyridazinyl-N-oxide), pyrimidinyl (e.g., 2-, 4- or 5-pyrimidinyl), pyrimidinyl wherein one or both of the nitrogen atoms are oxidized (e.g., 2-,4-,5- or 6-pyrimidinyl-N-oxide), pyrazinyl, piperidyl (e.g., 1-, 2-, 3- or 4-piperidyl), piperazinyl (e.g., 1- or 2-piperazinyl), indolyl (e.g., 3H-indole-2-, 3-, 4-, 5-, 6- or 7-yl), pyranyl (e.g., 2-, 3- or 4-pyranyl), thiopyranyl (e.g., 2-, 3- or 4-thiopyranyl), thiopyranyl wherein the sulfur atom is oxidized (e.g., 2-, 3- or 4-thiopyranyl-1,1-dioxide), morpholinyl (e.g., 2-, 3- or 4-morpholinyl), thiomorpholinyl, quinolyl (e.g., 2-, 3- or 4-quinolyl), isoquinolyl, pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), chromenyl (e.g., 2H-chromen-2- or 3-yl), 2-benzo[b]thienyl, 3-benzo[b]thienyl, 2-benzo[b]furanyl, 3-benzo[b]furanyl and the like.

Examples of the "substituent" of the "heterocyclic group" include those similar to the substituents that the "hydrocarbon group" of the above-mentioned "optionally substituted hydrocarbon group" for $R^{17}$ optionally has when the hydrocarbon group is cycloalkyl, aryl or aralkyl. The number of the substituents is 1 to 5, preferably 1 to 3.

Examples of the "acyl group" for $R^{17}$ include groups similar to the above-mentioned "acyl group" for $R^{13}$ or $R^{14}$ or the "acyl group" that each ring-constituting atom $X_3$ or $X_4$ may have when it is a carbon atom or a nitrogen atom.

Examples of the "optionally substituted mercapto group" for $R^{13}$ or $R^{14}$ or the "optionally substituted mercapto group" that each ring-constituting atom $X_3$ or $X_4$ may have when it is a carbon atom or a nitrogen atom include a group represented by —$SR^{18}$ wherein $R^{18}$ is a hydrogen atom, an optionally substituted hydrocarbon group, an optionally substituted heterocyclic group or an acyl group.

Examples of the "optionally substituted hydrocarbon group" for $R^{18}$ include groups similar to the above-mentioned "optionally substituted hydrocarbon group" for $R^{17}$.

Examples of the "optionally substituted heterocyclic group" for $R^{18}$ include groups similar to the above-mentioned "optionally substituted heterocyclic group" for $R^{17}$.

Examples of the "acyl group" for $R^{18}$ include groups similar to the above-mentioned "acyl group" for $R^{13}$ or $R^{14}$ or the "acyl group" that each ring-constituting atom $X_3$ or $X_4$ may have when it is a carbon atom or a nitrogen atom.

Examples of the "optionally substituted amino group" for $R^{13}$ or $R^{14}$ or the "optionally substituted amino group" that each ring-constituting atom $X_3$ or $X_4$ may have when it is a carbon atom or a nitrogen atom include a group represented by $-NR^{19}R^{20}$ wherein $R^{19}$ and $R^{20}$ are the same or different and each is a hydrogen atom, an optionally substituted hydrocarbon group, an optionally substituted heterocyclic group or an acyl group.

Examples of the "optionally substituted hydrocarbon group" for $R^{19}$ or $R^{2o}$ include groups similar to the above-mentioned "optionally substituted hydrocarbon group" for $R^{17}$.

Examples of the "optionally substituted heterocyclic group" for $R^{19}$ or $R^{2o}$ include groups similar to the above-mentioned "optionally substituted heterocyclic group" for $R^{17}$.

Examples of the "acyl group" for $R^{19}$ or $R^{2o}$ include groups similar to the above-mentioned "acyl group" for $R^{13}$ or $R^{14}$ or the "acyl group" that each ring-constituting atom $X_3$ or $X_4$ may have when it is a carbon atom or a nitrogen atom.

Examples of the "halogen atom" for $R^{13}$ or $R^{14}$ or the "halogen atom" that each ring-constituting atom $X_3$ or $X_4$ may have when it is a carbon atom or a nitrogen atom include a fluorine atom, a chlorine atom, a bromine atom and an iodine atom.

$R^1$ and $R^2$ are the same or different and each is a cyclic group optionally having substituent(s).

Examples of the "cyclic group" for $R^1$ or $R^2$ include an aryl group, an alicyclic hydrocarbon group and a heterocyclic group.

Examples of the above-mentioned "aryl group" include a $C_{6-14}$ aryl group such as phenyl, 1-naphthyl, 2-naphthyl, 2-biphenylyl, 3-biphenylyl, 4-biphenylyl, 2-anthryl and the like.

Examples of the above-mentioned "alicyclic hydrocarbon group" include a $C_{3-14}$ cycloalkyl group such as cyclopropyl, cyclobutyl, cyclopentyl, cyclohexyl, perhydronaphthyl, perhydroanthranyl, bicyclo[2,2,1]heptyl and the like (preferably, $C_{3-7}$ cycloalkyl group), a $C_{3-14}$ cycloalkenyl group such as cyclopropenyl, cyclobuten-1- or 3-yl, cyclopenten-1-, 3- or 4-yl, cyclohexen-1- or 3-yl and the like (preferably, $C_{3-7}$ cycloalkenyl group) and the like.

Examples of the above-mentioned "heterocyclic group" include a 4- to 7-membered nonaromatic heterocyclic group containing 1-3 heteroatoms such as a nitrogen atom, an oxygen atom, a sulfur atom and the like (e.g., oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, homomorpholinyl, homopiperazinyl and the like); a heteroaryl group (preferably, a 5- or 6-membered aromatic heterocyclic group or a fused ring group thereof) such as pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5-imidazolyl), triazolyl (e.g., 1,2,3-triazol-4-yl, 1,2,3-triazol-1-yl, 1,2,3-triazol-5-yl, 1,2,4-triazol-1-yl, 1,2,4-triazol-3-yl, 1,2,4-triazol-4-yl, 1,2,4-triazol-5-yl), tetrazolyl (e.g., tetrazol-1-, 2- or 5-yl), furyl (e.g., 2- or 3-furyl), thienyl (e.g., 2- or 3-thienyl), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), triazolyl (e.g., 2-, 4- or 5-thiazolyl), isothiazolyl (e.g., 3-, 4- or 5-isothiazolyl), thiadiazolyl (e.g., 1,2,3-thiadiazol-4- or 5-yl, 1,2,4-thiadiazol-3- or 5-yl, 1,2,5-thiadiazol-3-yl, 1,3,4-thiadiazol-2-yl), pyridyl (e.g., 1-, 2-, 3- or 4-pyridyl), pyridazinyl (e.g., 1-, 3- or 4-pyridazinyl), pyrimidinyl (e.g., 1-, 2-, 4- or 5-pyrimidinyl), pyrazinyl (e.g., 1- or 2-pyrazinyl), benzofuryl (e.g., 2- or 3-benzofuryl), benzothienyl (e.g., 2- or 3-benzothienyl), isoindolyl (e.g., 1- or 3-isoindolyl), benzimidazolyl (e.g., 2-benzimidazolyl), benzoxazolyl (e.g., 2-benzoxazolyl), benzoisooxazolyl (e.g., 3-benzoisooxazolyl), benzothiazolyl (e.g., 2-benzothiazolyl), benzoisothiazolyl (e.g., 3-benzoisothiazolyl), cinnolinyl (e.g., 3- or 4-cinnolinyl), quinazolinyl (e.g., 2- or 4-quinazolinyl), quinoxalinyl (e.g., 2- or 3-quinoxalinyl), phthalazinyl (e.g., 1- or 4-phthalazinyl), pteridinyl, indolyl (e.g., 3H-indol-2-, 3-, 4-, 5-, 6- or 7-yl), quinolyl (e.g., 3-, 4-, 5-, 6-, 7- or 8-quinolyl), isoquinolyl (e.g., 1-, 3- or 4-isoquinolyl), pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), imidazo[1,2-a]pyridyl, imidazo[2,1-b]thiazolyl, imidazo[1,2-a]pyrimidinyl, imidazo[1,2-b]pyridazinyl, imidazo[1,2-a]imidazolyl, imidazo[2,1-b](1.3.4)thiadiazolyl, pyrazolo[1,5-a]pyrimidinyl, pyrazolo[5,1-b]thiazolyl, pyrazolo[1,5-a]pyridyl and the like.

Examples of the substituent which the "cyclic group" for $R^1$ or $R^2$ may have include substituents similar to the substituents which the above-mentioned "hydrocarbon group" for $R^{17}$ may have when it is cycloalkyl, aryl or aralkyl.

The substituents can be present at substitutable positions. The number of substituents is 1 to 5, preferably 1 to 3.

As $R^2$, particularly a group represented by

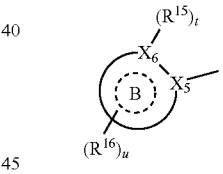

wherein ring B is a cyclic group having $X_5$ and $X_6$ as ring-constituting atoms, $X_5$ is a carbon atom or a nitrogen atom, $X_6$ is a carbon atom, a nitrogen atom, an oxygen atom or a sulfur atom;

$R^{15}$ is a substituent that $X_6$ may have when it is a carbon atom or a nitrogen atom;

$R^{16}$ is an optionally substituted alkyl group, an acyl group, an optionally substituted hydroxy group, an optionally substituted mercapto group, an optionally substituted amino group, a halogen atom, a cyano group or a nitro group;

t is 0 or 1; and u is an integer of 0 to 3 is preferable.

Examples of the "cyclic group" for ring B include groups similar to the "cyclic group" of the above-mentioned "cyclic group optionally having substituent(s)" for $R^1$ or $R^2$.

Examples of the "substituent" for $R^{15}$ include those similar to the substituents which the above-mentioned "cyclic group" for $R^1$ or $R^2$ may have.

One embodiment of $R^{15}$ is an electron withdrawing group or an electron donating group, and an electron withdrawing group is particularly preferable.

In one embodiment of the present invention, particularly, when $X_5$ is a carbon atom, and ring B is a basic cyclic group (e.g., a basic 5-membered heterocyclic group such as imidazolyl, pyrazolyl and the like; a basic 6-membered heterocyclic group such as pyridine, pyrazine, pyrimidine, pyridazine and the like, and the like), the "substituent" for $R^{15}$ is preferably an electron-withdrawing group.

On the other hand, when $X_5$ is a nitrogen atom, or when ring B is not a basic cyclic group, $R^{15}$ may be an electron-withdrawing group or not.

Examples of the electron-withdrawing group include a halogen atom (e.g., a fluorine atom, a chlorine atom, a bromine atom, an iodine atom), a cyano group, an acyl group, a halogenoalkyl group (e.g., a halogeno($C_{1-3}$)alkyl group such as fluoromethyl, chloromethyl, bromomethyl, iodomethyl, difluoromethyl, trifluoromethyl and the like, and the like) and the like.

Examples of the aforementioned "acyl group" include an acyl group derived from optionally substituted carboxylic acid, optionally substituted oxycarboxylic acid, optionally substituted sulfonic acid, optionally substituted sulfinic acid etc., and the like. Examples thereof include a group represented by the formula —$S(O)_v$—$R''$ wherein v is 1 or 2, $R^{21}$ is a hydroxy group, a hydrocarbon group optionally having substituent(s) or a heterocyclic group optionally having substituent(s); a group represented by the formula —$COOR^{22}$ wherein $R^{22}$ is a hydrogen atom, a hydrocarbon group optionally having substituent(s) or a heterocyclic group optionally having substituent(s); a group represented by the formula —$CONR^{23}R^{24}$ wherein $R^{23}$ and $R^{24}$ are the same or different and each is a hydrogen atom or a hydrocarbon group optionally having substituent(s) or a heterocyclic group optionally having substituent(s); a group represented by the formula —$SO_2NH$—$R^{25}$ wherein $R^{25}$ is a hydrogen atom, a hydrocarbon group optionally having substituent(s) or a heterocyclic group optionally having substituent(s); a group represented by the formula —CO—$R^{26}$ wherein $R^{26}$ is a hydrogen atom, a hydrocarbon group optionally having substituent(s) or a heterocyclic group optionally having substituent(s), and the like.

Examples of the "hydrocarbon group optionally having substituent(s)" for $R^{21}$, $R^{22}$, $R^{23}$, $R^{24}$, $R^{25}$ or $R^{26}$ include those similar to the above-mentioned "optionally substituted hydrocarbon group" for $R^{17}$.

Examples of the "heterocyclic group optionally having substituent (s)" for $R^{21}$, $R^{22}$, $R^{23}$, $R^{24}$, $R^{25}$ or $R^{26}$ include those similar to the above-mentioned "optionally substituted heterocyclic group" for $R^{17}$.

Of the above-mentioned groups, the electron withdrawing group is preferably a halogen atom, a cyano group, an acyl group or a trifluoromethyl group.

Examples of the electron donating group include a $C_{1-8}$ alkyl group (e.g., methyl, ethyl, propyl, isopropyl, butyl, isobutyl, sec-butyl, tert-butyl, pentyl, hexyl etc.), a $C_{1-8}$ alkylthio group (e.g., methylthio, ethylthio, propylthio, isopropylthio, butylthio, pentylthio, hexylthio etc.), a $C_{1-6}$ alkoxy group (e.g., methoxy, ethoxy, propoxy, isopropoxy, butoxy, pentyloxy, hexyloxy etc.), a group represented by the formula -$NR^{27}R^{28}$ wherein $R^{27}$ and $R^{28}$ are the same or different and each is a hydrogen atom or an alkyl group, and the like. Examples of the alkyl group for $R^{27}$ or $R^{28}$ include a $C_{1-6}$ alkyl group such as methyl, ethyl, propyl, isopropyl, butyl, isobutyl, sec-butyl, tert-butyl, pentyl, hexyl and the like, and a $C_{1-3}$ alkyl group is particularly preferable.

Of the above-mentioned groups, the electron donating group is preferably a $C_{1-3}$ alkyl group, a $C_{1-3}$ alkylthio group or a group represented by the formula —$NR^{27}R^{28}$ wherein each symbol is as defined above.

Of the aforementioned groups, the "substituent" for $R^{15}$ is preferably, for example, an electron withdrawing group or an electron donating group, each having 7 or less atoms and comparatively low molecular weight.

t is 0 or 1. When ring B is an aryl group or a heteroaryl group, t is preferably 1.

In the present specification, when t=1, it means that a substituent is present for $R^{15}$, and when t=0, it means that a substituent is absent for $R^{15}$ ($X_6$ is unsubstituted or $R^{15}$=H). When t=1, compound (I) may have one substituent for $R^{15}$, and when $X_6$ may have two substituents, compound (I) may have two substituents for $R^{15}$.

That is, in the present specification, the partial structure of compound (I) or (I'):

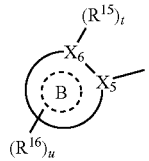

is

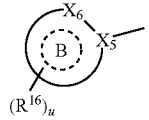
(1)

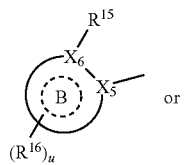
(2)

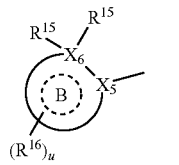
(3)

wherein two $R^{15}$ in the case of (3) may be the same or different, and preferably

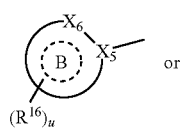
(1)

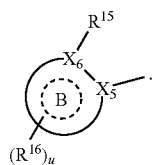
(2)

Preferable ring B is an aryl group or a heteroaryl group wherein $X_6$ is a carbon atom or a nitrogen atom, which has substituent $R^{15}$ on the ring-constituting atom $X_6$.

Examples of the "optionally substituted alkyl group", "acyl group", "optionally substituted hydroxy group", "optionally substituted mercapto group", "optionally substituted amino group" and "halogen atom" for $R^{16}$ include the above-mentioned "optionally substituted alkyl group", "acyl group", "optionally substituted hydroxy group", "optionally substituted mercapto group", "optionally substituted amino group" and "halogen atom" for $R^{13}$ or $R^{14}$ and those similar to the above-mentioned "optionally substituted alkyl group", "acyl group", "optionally substituted hydroxy group", "optionally substituted mercapto group", "optionally substituted amino group" and "halogen atom" that each ring-constituting atom $X_3$ or $X_4$ may have when it is a carbon atom or a nitrogen atom.

$R^{16}$ can be present at any substitutable position on ring B. The number of the substituents $R^{16}$ (i.e., u) is 0 to 3. When u is 2 or 3, respective $R^{16}$ may be the same or different. u is preferably 0 or 1, more preferably 0.

In present specification, u=0 means absence of a substituent for $R^{16}$ (unsubstituted or $R^{16}$=H).

In the formula (I) or (I'), $R^3$ and $R^4$ are the same or different and each is a hydrogen atom or an alkyl group, or $R^3$ and $R^4$ optionally form, together with the adjacent nitrogen atom, an optionally substituted nitrogen-containing heterocycle.

Examples of the "alkyl group" for $R^3$ or $R^4$ include a $C_{1-6}$ alkyl group such as methyl, ethyl, propyl, isopropyl, butyl, isobutyl, sec-butyl, tert-butyl, pentyl, hexyl and the like, preferably a $C_{1-3}$ alkyl group, particularly preferably methyl.

Examples of the "optionally substituted nitrogen-containing heterocycle" optionally formed by $R^3$ and $R^4$ together with the adjacent nitrogen atom include 3-hydroxyazetidine.

Preferably, $R^3$ and $R^4$ are the same or different and each is a hydrogen atom or an alkyl group.

The partial structure of the formula (I) or (I'):

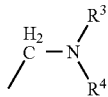

is preferably

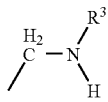

wherein $R^3$ is an alkyl group.

The partial structure is a group bonded to the carbon atom other than the ring-constituting atoms $X_1$-$X_4$ of ring A.

Y is a spacer selected from
(1) a bond (which means a single bond),
(2) a divalent $C_{1-6}$ hydrocarbon group optionally having substituent(s),
(3) —O—$(R^5)_m$—$(R^6)_n$— wherein $R^5$ is a divalent $C_{1-6}$ hydrocarbon group optionally having substituent(s), $R^6$ is an oxygen atom, —S(O)$_w$— wherein w is 0, 1 or 2, or

wherein $R^7$ is a hydrogen atom, an optionally substituted hydrocarbon group, an optionally substituted $C_{1-6}$ alkyl-carbonyl or an optionally substituted $C_{1-6}$ alkylsulfonyl, m is 0 or 1, n is 0 or 1, $R^6$ is preferably an oxygen atom, a sulfur atom or

wherein $R^7$ is as defined above,
(4)

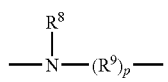

wherein $R^8$ is a hydrogen atom, an optionally substituted hydrocarbon group, an optionally substituted $C_{1-6}$ alkyl-carbonyl or an optionally substituted $C_{1-6}$ alkylsulfonyl, $R^9$ is a divalent $C_{1-6}$ hydrocarbon group optionally having substituent(s),
p is 0 or 1,
(5) —S(O)$_q$— wherein q is 0 or 1, and
(6) —S(O)$_r$—$R^{10}$— wherein $R^{10}$ is a divalent $C_{1-6}$ hydrocarbon group optionally having substituent(s), an oxygen atom or

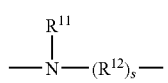

wherein $R^{11}$ is a hydrogen atom, an optionally substituted hydrocarbon group, an optionally substituted $C_{1-6}$ alkyl-carbonyl or an optionally substituted $C_{1-6}$ alkylsulfonyl, $R^{12}$ is a divalent $C_{1-6}$ hydrocarbon group optionally having substituent(s) or —SO$_2$—, s is 0 or 1, r is 0, 1 or 2.

Here, regarding the two bonds (hereinafter to be referred to as bonds (a) and (b)) possessed by —Y—, either of the bonds (a) and (b) may be bonded to $R^1$.

That is, in the present specification, the bonds (a) and (b) of Y in

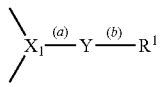

are interchangeable, and both

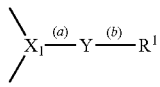

and

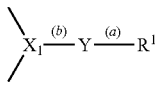

are encompassed.

Examples of the "divalent $C_{1-6}$ hydrocarbon group" of the "divalent $C_{1-6}$ hydrocarbon group optionally having substituent(s)" for Y include "divalent $C_{1-6}$ aliphatic hydrocarbon group". Examples of the "divalent $C_{1-6}$ aliphatic hydrocarbon group" include an alkylene group, an alkenylene group and an alkynylene group. For example, (i) $C_{1-6}$ alkylene (e.g., —$CH_2$—, —$(CH_2)_2$—, —$(CH_2)_3$—, —$(CH_2)_4$—, —$(CH_2)_5$—, —$(CH_2)_6$—, —$CH(CH_3)$—, —$(CH_3)_2$—, —$(CH(CH_3))_2$—, —$(CH_2)_2C(CH_3)_2$—, —$(CH_2)_3C(CH_3)_2$—, etc.);

(ii) $C_{2-6}$ alkenylene (e.g., —CH=CH—, —$CH_2$—CH=CH—, —CH=CH—$CH_2$—, —CH=CH—$CH_2$—$CH_2$—, —$C(CH_3)_2$—CH=CH—, —$CH_2$—CH=CH—$CH_2$—, —$CH_2$—$CH_2$—CH=CH—, —CH=CH—CH=CH—, —CH=CH—$CH_2$—$CH_2$—$CH_2$— etc.);

(iii) $C_{2-6}$ alkynylene (e.g., —C≡C—, —$CH_2$—C≡C—, —$CH_2$—C≡C—$CH_2$—$CH_2$— etc.) and the like can be mentioned.

Examples of the "substituent(s)" in the "divalent $C_{1-6}$ hydrocarbon group optionally having substituent(s)" include those similar to the substituents that the "hydrocarbon group" of the above-mentioned "optionally substituted hydrocarbon group" for $R^{17}$ optionally has when it is alkyl, alkenyl or alkynyl, and particularly, a halogen atom (e.g., a fluorine atom, a chlorine atom, a bromine atom, an iodine atom), hydroxy, $C_{1-6}$ alkoxy-carbonyl, oxo and the like are preferable. The number of the "substituent(s)" is, for example, 1 to 5, preferably 1 to 3.

Examples of the "divalent $C_{1-6}$ hydrocarbon group optionally having substituent(s)" for $R^5$, $R^9$, $R^{10}$ or $R^{12}$ include those similar to the above-mentioned "divalent $C_{1-6}$ hydrocarbon group optionally having substituent(s)" for Y.

Examples of the "optionally substituted hydrocarbon group" for $R^7$, $R^8$ or $R^{11}$ include those similar to the above-mentioned "optionally substituted hydrocarbon group" for $R^{17}$.

Examples of the "optionally substituted $C_{1-6}$ alkyl-carbonyl" for $R^7$, $R^8$ or $R^{11}$ include $C_{1-6}$ alkyl-carbonyl optionally having 1 to 5, preferably 1 to 3 halogen atoms (e.g., a fluorine atom, a chlorine atom, a bromine atom, an iodine atom) at substitutable positions and the like. Examples of the "optionally substituted $C_{1-6}$ alkyl-carbonyl" include acetyl, monochloroacetyl, trifluoroacetyl, trichloroacetyl, propanoyl, butanoyl, pentanoyl, hexanoyl and the like.

Examples of the "optionally substituted $C_{1-6}$ alkylsulfonyl" for $R^7$, $R^8$ or $R^{11}$ include $C_{1-6}$ alkylsulfonyl optionally having 1 to 5, preferably 1 to 3 halogen atoms (e.g., a fluorine atom, a chlorine atom, a bromine atom, an iodine atom) at substitutable positions and the like. Examples of the "optionally substituted $C_{1-6}$ alkylsulfonyl" include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, sec-butylsulfonyl, tert-butylsulfonyl, pentylsulfonyl, hexylsulfonyl and the like.

Preferable examples of Y include as follows.

(1) a bond, (2) a $C_{1-6}$ alkylene group optionally substituted by 1 to 3 substituents selected from a halogen atom, hydroxy, oxo and $C_{1-6}$ alkoxy-carbonyl (e.g., methoxycarbonyl) (preferably, a $C_{1-6}$ alkylene group optionally substituted by 1 to 3 substituents selected from halogen atom, hydroxy and oxo):

for example,
—$CH_2$—,
—CH(OH)—,
—C(=O)—,
—$(CH_2)_2$—,
—$(CH_2)_3$—,
—CH(OH)—$(CH_2)_2$—,
—$(CH_2)_4$—,
—$(CH_2)_5$—,
—$(CH_2)_6$—,
—$CH(CH_3)$—,
—$CH(CH_2OH)$—,
—$CH(COOCH_3)$—,
—$C(CH_3)_2$—,
—$CH(CF_3)$—,
—$(CH(CH_3))_2$—,
—$(CF_2)_2$—,
—C(=O)—$CH_2$—,
—$(CH_2)_2C(CH_3)_2$—,
—$(CH_2)_3C(CH_3)_2$— and the like;

(3) (i) —O—;

(ii) —O—$R^{5'}$— wherein $R^{5'}$ is a $C_{1-6}$ alkylene group optionally substituted by 1 to 3 substituents selected from a halogen atom, hydroxy and oxo):
for example,
—O—$CH_2$—,
—O—C(=O)—,
—O—CH(OH)—,
—O—$CF_2$—,
—O—$(CH_2)_2$—,
—O—$CH(CH_3)$—,
—O—$CH(CF_3)$—,
—O—$C(CH_3)_2$— and the like;

(iii) —O—$R^{5'}$—O— wherein $R^{5'}$ is as defined above:
for example,
—O—$CH_2$—O—,
—O—C(=O)—O—,
—O—CH(OH)—O—,
—O—$CF_2$—O—,
—O—$(CH_2)_2$—O—,
—O—$CH(CH_3)$—O—,
—O—$CH(CF_3)$—O—,
—O—$C(CH_3)_2$—O— and the like;

(iv) —O—$R^{5'}$—S— wherein $R^{5'}$ is as defined above:
for example,
—O—$CH_2$—S—,
—O—C(=O)—S—,
—O—CH(OH)—S—,
—O—$CF_2$—S—, —O—$(CH_2)_2$—S—,
—O—$CH(CH_3)$—S—,
—O—$CH(CF_3)$—S—,
—O—$C(CH_3)_2$—S— and the like;

(v) —O—$R^{5'}$—$NR^{7'}$— wherein $R^{5'}$ is as defined above, and $R^{7'}$ is (a) a hydrogen atom, (b) $C_{1-6}$ alkyl optionally substituted by 1 to 3 halogen atoms or hydroxy, (c) $C_{1-6}$ alkyl-carbonyl or (d) $C_{1-6}$ alkylsulfonyl:
for example,
—O—$CH_2$—NH—,
—O—CH(OH)—NH—,
—O—$CF_2$—NH—,
—O—C(=O)—NH—,
—O—$(CH_2)_2$—NH—,
—O—$CH(CH_3)$—NH—,
—O—$CH(CF_3)$—NH—, —O—C(CH$_3$)$_2$—NH—,
—O—CH$_2$—N(CH$_3$)—,
—O—CF$_2$—N(CH$_3$)—,
—O—C(=O)—N(CH$_3$)—,
—O—CH$_2$—N(CF$_3$)—,
—O—CH$_2$—N(COCH$_3$)—,
—O—CH$_2$—N(SO$_2$CH$_3$)— and the like;
(vi) —O—NR$^{7'}$— wherein R$^{7'}$ is as defined above:
for example,
—O—NH—,
—O—N(CH$_3$)—,
—O—N(CF$_3$)—,
—O—N(OH)—,
—O—N(COCH$_3$)—,
—O—N(SO$_2$CH$_3$)— and the like,
(4) (i) —N(R$^{8'}$)— wherein R$^{8'}$ is (a) a hydrogen atom, (b) C$_{1-6}$ alkyl optionally substituted by 1 to 3 halogen atoms or hydroxy, (c) C$_{1-6}$ alkyl-carbonyl or (d) C$_{1-6}$ alkylsulfonyl;
for example,
—NH—,
—N(CH$_3$)—,
—N(CF$_3$)—,
—N(CH$_2$OH)—,
—N(COCH$_3$)—,
—N(SO$_2$CH$_3$)— and the like;
(ii) —N(R$^{8'}$)—R$^{9'}$— wherein R$^{8'}$ is as defined above, and R$^{9'}$ is a C$_{1-6}$ alkylene group optionally substituted by 1 to 3 substituents selected from a halogen atom, hydroxy and oxo;
for example,
—NH—CH$_2$—,
—NH—CF$_2$—,
—NH—CH(OH)—,
—NH—CH(CH$_3$)—,
—NH—C(CH$_3$)$_2$—,
—NH—C(=O)—,
—N(CH$_3$)—CH$_2$—,
—N(CH$_3$)—CF$_2$—,
—N(CH$_3$)—CH(OH)—,
—N(CH$_3$)—C(=O)—,
—N(CF$_3$)—CH$_2$—,
—N(CH$_2$OH)—CH$_2$—,
—N(COCH$_3$)—CH$_2$—,
—N(SO$_2$CH$_3$)—CH$_2$— and the like;
(5) —S—;
—SO—;
(6) (i) —S—R$^{10'}$— wherein R$^{10'}$ is a C$_{1-6}$ alkylene group optionally substituted by 1 to 3 substituents selected from a halogen atom, hydroxy and oxo;
for example,
—S—CH$_2$—,
—S—C(=O)—,
—S—CH(OH)—,
—S—CF$_2$—,
—S—(CH$_2$)$_2$—,
—S—CH(CH$_3$)—,
—S—CH(CF$_3$)—,
—S—C(CH$_3$)$_2$— and the like;
(ii) —S—N(R$^{11'}$)— wherein R$^{11'}$ is (a) a hydrogen atom, (b) C$_{1-6}$ alkyl optionally substituted by 1 to 3 halogen atoms or hydroxy, (c) C$_{1-6}$ alkyl-carbonyl or (d) C$_{1-6}$ alkylsulfonyl;
for example,
—S—NH—,
—S—N(CH$_3$)—,
—S—N(CF$_3$)—,
—S—N(CH$_2$OH)—,
—S—N(COCH$_3$)—,
—S—N(SO$_2$CH$_3$)— and the like;

(iii) —S—N(R$^{11'}$)—R$^{12'}$- wherein R$^{11'}$ is as defined above, and R$^{12'}$ is a C$_{1-6}$ alkylene group optionally substituted by 1 to 3 substituents selected from a halogen atom, hydroxy and oxo;
for example,
—S—NH—CH$_2$—,
—S—NH—CF$_2$—,
—S—NH—CH(OH)—,
—S—NH—CH(CH$_3$)—,
—S—NH—C(CH$_3$)$_2$—,
—S—NH—C(=O)—,
—S—N(CH$_3$)—CH$_2$—,
—S—N(CH$_3$)—CF$_2$—,
—S—N(CH$_3$)—CH(OH)—,
—S—N(CF$_3$)—CH$_2$—,
—S—N(CH$_3$)—C(=O)—,
—S—N(CH$_2$OH)—CH$_2$—,
—S—N(CH$_2$OH)—CF$_2$—,
—S—N(CH$_2$OH)—C(=O)—,
—S—N(COCH$_3$)—CH$_2$—,
—S—N(SO$_2$CH$_3$)—CH$_2$— and the like;
(iv) —SO—R$^{10'}$ wherein R$^{10'}$ is as defined above;
for example,
—SO—CH$_2$—,
—SO—C(=O)—,
—SO—CH(OH)—,
—SO—CF$_2$—,
—SO—(CH$_2$)$_2$—,
—SO—CH(CH$_3$)—,
—SO—CH(CF$_3$)—,
—SO—C(CH$_3$)$_2$— and the like;
(v) —SO—N(R$^{11'}$)— wherein R$^{11'}$ is as defined above;
for example,
—SO—NH—,
—SO—N(CH$_3$)—,
—SO—N(CF$_3$)—,
—SO—N(CH$_2$OH)—,
—SO—N(COCH$_3$)—,
—SO—N(SO$_2$CH$_3$)— and the like;
(vi) —SO—N(R$^{11'}$)—R$^{12'}$— wherein R$^{11'}$ and R$^{12'}$ are each as defined above;
for example,
—SO—NH—CH$_2$—,
—SO—NH—CF$_2$—,
—SO—NH—CH(OH)—,
—SO—NH—CH(CH$_3$)—,
—SO—NH—C(CH$_3$)$_2$—,
—SO—NH—C(=O)—,
—SO—N(CH$_3$)—CH$_2$—,
—SO—N(CH$_3$)—CF$_2$—,
—SO—N(CH$_3$)—CH(OH)—,
—SO—N(CF$_3$)—CH$_2$—,
—SO—N(CH$_3$)—C(=O)—,
—SO—N(CH$_2$OH)—CH$_2$—,
—SO—N(CH$_2$OH)—CF$_2$—,
—SO—N(CH$_2$OH)—C(=O)—,
—SO—N(COCH$_3$)—CH$_2$—,
—SO—N(SO$_2$CH$_3$)—CH$_2$— and the like;
(vii) —SO$_2$—R$^{10'}$— wherein R$^{10'}$ is as defined above;
for example,
—SO$_2$—CH$_2$—,
—SO$_2$—C(=O)—,
—SO$_2$—CH(OH)—,
—SO$_2$—CF$_2$—,
—SO$_2$—(CH$_2$)$_2$—,
—SO$_2$—CH(CH$_3$)—, —SO$_2$—C(CH$_3$)$_2$—,
—SO$_2$—CH(CF$_3$)— and the like;
(viii) —SO$_2$—N(R$^{11'}$)— wherein R$^{11'}$ is as defined above;
for example,
—SO$_2$—NH—,
—SO$_2$—N(CH$_3$)—, —SO$_2$—N(CF$_3$)—,
—SO$_2$—N(CH$_2$OH)—,
—SO$_2$—N(COCH$_3$)—,
—SO$_2$—N(SO$_2$CH$_3$)— and the like;
(ix) —SO$_2$—N(R$^{11'}$)—R$^{12'}$— wherein R$^{11'}$ and R$^{12'}$ are each as defined above;
for example,
—SO$_2$—NH—CH$_2$—,
—SO$_2$—NH—CF$_2$—,
—SO$_2$—NH—CH(OH)—,
—SO$_2$—NH—CH(CH$_3$)—,
—SO$_2$—NH—C(CH$_3$)$_2$—,
—SO$_2$—NH—C(=O)—,
—SO$_2$—N(CH$_3$)—CH$_2$—,
—SO$_2$—N(CH$_3$)—CF$_2$—
—SO$_2$—N(CH$_3$)—CH(OH)—,
—SO$_2$—N(CF$_3$)—CH$_2$—,
—SO$_2$—N(CH$_3$)—C(=O)—,
—SO$_2$—N(CH$_2$OH)—CH$_2$—,
—SO$_2$—N(CH$_2$OH)—CF$_2$—,
—SO$_2$—N(CH$_2$OH)—C(=O)—,
—SO$_2$—N(COCH$_3$)—CH$_2$—,
—SO$_2$—N(SO$_2$CH$_3$)—CH$_2$— and the like;
(x) —SO$_2$—O—;
(xi) —SO$_2$—N(R$^{11'}$)—SO$_2$— wherein R$^{11'}$ is as defined above;
for example,
—SO$_2$—NH—SO$_2$—,
—SO$_2$—N(CH$_3$)—SO$_2$—,
—SO$_2$—N(CF$_3$)—SO$_2$—,
—SO$_2$—N(CH$_2$OH)—SO$_2$—,
—SO$_2$—N(COCH$_3$)—SO$_2$—,
—SO$_2$—N(SO$_2$CH$_3$)—SO$_2$— and the like.

Of these, preferable embodiment of Y is
(1) a bond;
(2) a C$_{1-6}$ alkylene group optionally substituted by 1 to 3 substituents selected from a halogen atom, hydroxy, oxo and C$_{1-6}$ alkoxy-carbonyl (as C$_{1-6}$ alkylene, of these, a methylene group is preferable);
(3) —O—;
(4) —N(R$^{8'}$)— wherein R$^{8'}$ is (a) a hydrogen atom, (b) C$_{1-6}$ alkyl optionally substituted by 1 to 3 halogen atoms or hydroxy, (c) C$_{1-6}$ alkyl-carbonyl or (d) C$_{1-6}$ alkylsulfonyl; —N(R$^{8'}$)R$^{9'}$— wherein R$^{8'}$ is as defined above, and R$^{9'}$ is a C$_{1-6}$ alkylene group optionally substituted by 1 to 3 substituents selected from a halogen atom, hydroxy and oxo;
(5) —S—;
—SO—; or
(6) —SO$_2$—R$^{10'}$— wherein R$^{10'}$ is a C$_{1-6}$ alkylene group optionally substituted by 1 to 3 substituents selected from a halogen atom, hydroxy and oxo;
—SO$_2$—N(R$^{11'}$)— wherein R$^{11'}$ is (a) a hydrogen atom, (b) C$_{1-6}$ alkyl optionally substituted by 1 to 3 halogen atoms or hydroxy, (c) C$_{1-6}$ alkyl-carbonyl or (d) C$_{1-6}$ alkylsulfonyl.

More preferable embodiment of Y is
(1) a bond;
(2) a C$_{1-6}$ alkylene group optionally substituted by 1 to 3 substituents selected from a halogen atom, hydroxy and oxo;
(3) —O—;
(4) —N(R$^{8'}$)— wherein R$^{8'}$ is (a) a hydrogen atom, (b) C$_{1-6}$ alkyl optionally substituted by 1 to 3 halogen atoms or hydroxy, (c) C$_{1-6}$ alkyl-carbonyl or (d) C$_{1-6}$ alkylsulfonyl;
(5) —S—;
—SO—; or
(6) —SO$_2$—R$^{10'}$— wherein R$^{10'}$ is a C$_{1-6}$ alkylene group optionally substituted by 1 to 3 substituents selected from a halogen atom, hydroxy and oxo;
—SO$_2$—N(R$^{11'}$)— wherein R$^{11'}$ is (a) a hydrogen atom, (b) C$_{1-6}$ alkyl optionally substituted by 1 to 3 halogen atoms or hydroxy, (c) C$_{1-6}$ alkyl-carbonyl or (d) C$_{1-6}$ alkylsulfonyl.

Y is particularly preferably a bond, —CH$_2$—, —CH(CH$_3$)—, —C(CH$_3$)$_2$—, —CH(OH)—, —CH(CO$_2$CH$_3$)—, —CH(CH$_2$OH)—, —CO—, —O—, —NH—, —N(CH$_3$)—, —NH—CO—, —N(COCH$_3$)—, —S—, —S—CH$_2$—, —SO—, —SO$_2$—CH$_2$—, —SO$_2$—C(CH$_3$)$_2$—, —SO$_2$—NH— or —SO$_2$—N(CH$_3$)—.

Y is more particularly preferably a bond, —CH$_2$—, —CH(CH$_3$)—, —C(CH$_3$)$_2$—, —O—, —NH—, —N(CH$_3$)—, —S—, —SO—, —SO$_2$—CH$_2$—, —SO$_2$—C(CH$_3$)$_2$—, SO$_2$—NH— or —SO$_2$—N(CH$_3$)—.

In other embodiment, Y is preferably
(1) a bond;
(2) a C$_{1-6}$ alkylene group optionally substituted by 1 to 3 substituents selected from hydroxy, C$_{1-6}$ alkoxy-carbonyl and oxo;
(3) —O—;
(4) —N(R$^{8'}$)— wherein R$^{8'}$ is (a) a hydrogen atom, (b) C$_{1-6}$ alkyl or (c) C$_{1-6}$ alkyl-carbonyl;
—N(R$^{8'}$)—R$^{9'}$ wherein R$^{8'}$ is as defined above, and R$^{9'}$ is a C$_{1-6}$ alkylene group optionally substituted by oxo;
(5) —S—;
—SO—; or
(6) —S—R$^{10'}$— wherein R$^{10'}$ is a C$_{1-6}$ alkylene group;
—SO$_2$—R$^{10'}$— wherein R$^{10'}$ is as defined above;
—SO$_2$—N(R$^{11'}$)— wherein R$^{11'}$ is (a) a hydrogen atom or (b) C$_{1-6}$ alkyl.

Of these, Y is preferably a bond, —CH$_2$—, —CH(OH)—, —CH(CH$_2$OH)—, —CH(CO$_2$CH$_3$)—, —CO—, —O—, —NH—, —N(CH$_3$)—, —NH—CO—, —N(COCH$_3$)—, —S—, —S—CH$_2$—, —SO—, —SO$_2$—CH$_2$— or —SO$_2$—N(CH$_3$)—.

Preferable embodiment of each group other than Y in compound (I) or (I') are shown in the following.

Ring A is preferably a thiophene ring, a furan ring, a pyrrole ring, an imidazole ring, a pyrazole ring, an isothiazole ring, a thiazole ring, an isoxazole ring, an oxazole ring, an oxazoline ring, an oxazolidine ring, a thiazoline ring, a thiazolidine ring, a pyrrolidine ring, a pyrroline ring, an imidazolidine ring, an imidazoline ring, a pyrazolidine ring, a pyrazoline ring, a furazan ring, a tetrahydrofuran ring or the like, more preferably a thiophene ring, an imidazole ring, a pyrazole ring or a thiazole ring.

R$^1$ is preferably a C$_{6-14}$ aryl group, a 4- to 7-membered nonaromatic heterocyclic group, or a 5- or 6-membered aromatic heterocyclic group or a fused ring group thereof (e.g., fused ring group wherein a 5- or 6-membered aromatic heterocyclic group is condensed with a benzene ring or a 5- or 6-membered aromatic heterocycle) (e.g., a C$_{6-14}$ aryl group such as phenyl, 1- or 2-naphthyl and the like; a 4- to 7-membered nonaromatic heterocyclic group such as 1-, 2- or 3-pyrrolidinyl, 1-, 2-, 3- or 4-piperidyl and the like; a 5- or 6-membered aromatic heterocyclic group such as 2- or 3-thienyl, 2- or 3-furyl, 1-, 2- or 3-pyrrolyl, 2-, 4- or 5-oxazolyl, 2-, 4- or 5-thiazolyl, 1-, 2-, 4- or 5-imidazolyl, 3-, 4- or 5-isoxazolyl, 3-, 4- or 5-isothiazolyl, 1-, 3-, 4- or 5-pyrazolyl, 1-, 2-, 3- or 4-pyridyl, 1-, 2-, 4- or 5-pyrimidinyl, 1-, 3- or 4-pyridazinyl, 1- or 2-pyrazinyl and the like; a fused ring group such as 2- or 3-benzofuryl, 2- or 3-benzothienyl, 1- or 3-isoindolyl, 2-benzimidazolyl, 2-benzoxazolyl, 3-benzoisooxazolyl, 2-benzothiazolyl, 3-benzoisothiazolyl, 2-, 3- or 4-quinolyl, 1-, 3- or 4-isoquinolyl, 3- or 4-cinnolinyl, 2- or 4-quinazolinyl, 2- or 3-quinoxalinyl, 1- or 4-phthalazinyl, naphthyridinyl, pteridinyl etc. and the like), each of which is optionally substituted by 1 to 3 substituents selected from (i) a halogen atom (e.g., a fluorine atom, a chlorine atom, a bromine atom, an iodine atom), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen atoms (e.g., a fluorine atom, a chlorine atom, a bromine atom, an iodine atom), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen atoms (e.g., a fluorine atom, a chlorine atom, a bromine atom, an iodine atom), (vi) amino optionally mono- or di-substituted by $C_{1-6}$ alkyl (e.g., methyl, ethyl, propyl, isopropyl, butyl, isobutyl, sec-butyl, tert-butyl, pentyl, hexyl etc.), (vii) oxo, (viii) carbamoyl, (ix) mono-$C_{1-6}$ alkyl-carbamoyl (e.g., methylcarbamoyl, ethylcarbamoyl etc.), (x) di-$C_{1-6}$ alkyl-carbamoyl (e.g., dimethylcarbamoyl, diethylcarbamoyl, ethylmethylcarbamoyl etc.), (xi) $C_{1-6}$ alkylsulfonyl (e.g., methylsulfonyl, ethylsulfonyl etc.) and (xii) $C_{1-6}$ alkyl-carbonylamino (e.g., acetylamino etc.).

Of these, $R^1$ is preferably a phenyl group, a pyrrolidinyl group (e.g., 1-, 2- or 3-pyrrolidinyl), a piperidyl group (e.g., 1-, 2-, 3- or 4-piperidyl), a pyridyl group (e.g., 1-, 2-, 3- or 4-pyridyl), a pyrazolyl group (e.g., 1-, 3-, 4- or 5-pyrazolyl), a furyl group (e.g., 2- or 3-furyl group), a thienyl group (e.g., 2- or 3-thienyl), a thiazolyl group (e.g., 2-, 4- or 5-thiazolyl) or a pyrimidinyl group (e.g., 1-, 2-, 4- or 5-pyrimidinyl) [of these, a phenyl group, a pyrrolidinyl group, a piperidyl group, a pyridyl group, a pyrazolyl group, a furyl group or a thienyl group], each of which is optionally substituted by 1 to 3 substituents selected from (i) a halogen atom (e.g., a fluorine atom, a chlorine atom, a bromine atom, an iodine atom), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen atoms (e.g., a fluorine atom, a chlorine atom, a bromine atom, an iodine atom), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen atoms (e.g., a fluorine atom, a chlorine atom, a bromine atom, an iodine atom), (vi) amino optionally mono- or di-substituted by $C_{1-6}$ alkyl (e.g., methyl, ethyl, propyl, isopropyl, butyl, isobutyl, sec-butyl, tert-butyl, pentyl, hexyl etc.), (vii) oxo, (viii) carbamoyl, (ix) mono-$C_{1-6}$ alkyl-carbamoyl (e.g., methylcarbamoyl, ethylcarbamoyl etc.), (x) di-$C_{1-6}$ alkyl-carbamoyl (e.g., dimethylcarbamoyl, diethylcarbamoyl, ethylmethylcarbamoyl etc.), (xi) $C_{1-6}$ alkylsulfonyl (e.g., methylsulfonyl, ethylsulfonyl etc.) and (xii) $C_{1-6}$ alkyl-carbonylamino (e.g., acetylamino etc.), particularly preferably a phenyl group, a pyridyl group, a furyl group, a thiazolyl group or a pyrimidinyl group [of these, a phenyl group or a pyridyl group], each of which is optionally substituted by 1 to 3 substituents selected from (i) a halogen atom (e.g., a fluorine atom, a chlorine atom, a bromine atom, an iodine atom), (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen atoms (e.g., a fluorine atom, a chlorine atom, a bromine atom, an iodine atom) and (iii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen atoms (e.g., a fluorine atom, a chlorine atom, a bromine atom, an iodine atom).

In another embodiment, $R^1$ is preferably a $C_{6-14}$ aryl group or a 5- or 6-membered aromatic heterocyclic group, each of which is optionally substituted by 1 to 3 substituents selected from (i) a halogen atom, (ii) $C_{1-6}$ alkyl and (iii) $C_{1-6}$ alkoxys.

Of these, $R^1$ is preferably phenyl, 2- or 3-furyl, 2-, 3-, 4- or 5-thiazolyl, 1-, 2-, 3- or 4-pyridyl, or 1-, 2-, 4- or 5-pyrimidinyl, each of which is optionally substituted by 1 to 3 substituents selected from (i) a halogen atom (particularly a fluorine atom, a chlorine atom, a bromine atom), (ii) $C_{1-6}$ alkyl (particularly methyl) and (iii) $C_{1-6}$ alkoxy (particularly methoxy).

$R^2$ is preferably (1) a $C_{6-14}$ aryl group (e.g., phenyl group etc.), (2) a $C_{3-7}$ cycloalkyl group (e.g., cyclopentyl group, cyclohexyl group etc.), (3) a 5- or 6-membered aromatic heterocyclic group or a fused ring group thereof (e.g., a fused ring group wherein a 5- or 6-membered aromatic heterocyclic group is condensed with a benzene ring or a 5- or 6-membered aromatic heterocycle) (e.g., a 5 or 6-membered aromatic heterocyclic group such as 2- or 3-thienyl, 2- or 3-furyl, 1-, 2- or 3-pyrrolyl, 2-, 4- or 5-oxazolyl, 2-, 4- or 5-thiazolyl, 1-, 2-, 4- or 5-imidazolyl, 3-, 4- or 5-isoxazolyl, 3-, 4- or 5-isothiazolyl, 1-, 3-, 4- or 5-pyrazolyl, 1-, 2-, 3- or 4-pyridyl, 1-, 2-, 4- or 5-pyrimidinyl, 1-, 3- or 4-pyridazinyl, 1- or 2-pyrazinyl and the like; a fused ring group such as 2- or 3-benzofuryl, 2- or 3-benzothienyl, 1- or 3-isoindolyl, 2-benzimidazolyl, 2-benzoxazolyl, 3-benzoisooxazolyl, 2-benzothiazolyl, 3-benzoisothiazolyl, 2-, 3- or 4-quinolyl, 1-, 3- or 4-isoquinolyl, 3- or 4-cinnolinyl, 2- or 4-quinazolinyl, 2- or 3-quinoxalinyl, 1- or 4-phthalazinyl, naphthyridinyl, pteridinyl etc. and the like) or (4) a 4- to 7-membered nonaromatic heterocyclic group (e.g., 1-, 2- or 3-pyrrolidinyl group, 1-, 2-, 3- or 4-piperidyl group etc.), each of which is optionally substituted by 1 to 3 substituents selected from (i) a halogen atom (e.g., a fluorine atom, a chlorine atom, a bromine atom, an iodine atom), (ii) cyano, (iii) $C_{1-6}$ alkyl (e.g., methyl, ethyl, propyl, isopropyl etc.) optionally substituted by 1 to 5 (preferably 1 to 3) halogen atoms (e.g., a fluorine atom, a chlorine atom, a bromine atom, an iodine atom), (iv) $C_{1-6}$ alkoxy (e.g., methoxy, ethoxy, propoxy, isopropoxy etc.), (v) amino optionally mono- or di-substituted by $C_{1-6}$ alkyl (e.g., methyl, ethyl, propyl, isopropyl, butyl, isobutyl, sec-butyl, tert-butyl, pentyl, hexyl etc.), (vi) carbamoyl, (vii) mono-$C_{1-6}$ alkyl-carbamoyl (e.g., methylcarbamoyl, ethylcarbamoyl etc.), (viii) di-$C_{1-6}$ alkyl-carbamoyl (e.g., dimethylcarbamoyl, diethylcarbamoyl, ethylmethylcarbamoyl etc.), (ix) $C_{1-6}$ alkylsulfonyl (e.g., methylsulfonyl, ethylsulfonyl etc.), (x) $C_{1-6}$ alkyl-carbonylamino (e.g., acetylamino etc.) and (xi) $C_{1-6}$ alkyl-carbonyl (e.g., acetyl etc.).

Of these, $R^2$ is preferably a $C_{6-14}$ aryl group (e.g., phenyl group) or a 5- or 6-membered aromatic heterocyclic group (e.g., 2- or 3-thienyl, 2- or 3-furyl, 1-, 2- or 3-pyrrolyl, 2-, 4- or 5-oxazolyl, 2-, 4- or 5-thiazolyl, 1-, 2-, 4- or 5-imidazolyl, 3-, 4- or 5-isoxazolyl, 3-, 4- or 5-isothiazolyl, 1-, 3-, 4- or 5-pyrazolyl, 1-, 2-, 3- or 4-pyridyl, 1-, 2-, 4- or 5-pyrimidinyl, 1-, 3- or 4-pyridazinyl, 1- or 2-pyrazinyl etc.), each of which is optionally substituted by 1 to 3 substituents selected from (i) a halogen atom (e.g., a fluorine atom, a chlorine atom, a bromine atom, an iodine atom), (ii) cyano, (iii) $C_{1-6}$ alkyl (e.g., methyl, ethyl, propyl, isopropyl etc.) optionally substituted by 1 to 5 (preferably 1 to 3) halogen atoms (e.g., a fluorine atom, a chlorine atom, a bromine atom, an iodine atom), (iv) $C_{1-6}$ alkoxy (e.g., methoxy, ethoxy, propoxy, isopropoxy etc.), (v) amino optionally mono- or di-substituted by $C_{1-6}$ alkyl (e.g., methyl, ethyl, propyl, isopropyl, butyl, isobutyl, sec-butyl, tert-butyl, pentyl, hexyl etc.), (vi) carbamoyl, (vii) mono-$C_{1-6}$ alkyl-carbamoyl (e.g., methylcarbamoyl, ethylcarbamoyl etc.), (viii) di-$C_{1-6}$ alkyl-carbamoyl (e.g., dimethylcarbamoyl, diethylcarbamoyl, ethylmethylcarbamoyl etc.), (ix) $C_{1-6}$ alkylsulfonyl (e.g., methylsulfonyl, ethylsulfonyl etc.), (x) $C_{1-6}$ alkyl-carbonylamino (e.g., acetylamino etc.) and (xi) $C_{1-6}$ alkyl-carbonyl (e.g., acetyl etc.).

$R^2$ is particularly preferably phenyl or 1-, 2-, 3- or 4-pyridyl, each of which is optionally substituted by 1 to 3 substituents selected from (i) a halogen atom (e.g., a fluorine atom, a chlorine atom, a bromine atom, an iodine atom), (ii) cyano, (iii) $C_{1-6}$ alkyl (e.g., methyl, ethyl, propyl, isopropyl etc.) optionally substituted by 1 to 5 (preferably 1 to 3) halogen atoms (e.g., a fluorine atom, a chlorine atom, a bromine atom, an iodine atom), (iv) $C_{1-6}$ alkoxy (e.g., methoxy, ethoxy, propoxy, isopropoxy etc.), (v) amino optionally mono- or di-substituted by $C_{1-6}$ alkyl (e.g., methyl, ethyl, propyl, isopropyl, butyl, isobutyl, sec-butyl, tert-butyl, pentyl, hexyl etc.), (vi) carbamoyl, (vii) mono-$C_{1-6}$ alkyl-carbamoyl (e.g., methylcarbamoyl, ethylcarbamoyl etc.), (viii) di-$C_{1-6}$ alkyl-carbamoyl (e.g., dimethylcarbamoyl, diethylcarbamoyl, ethylmethylcarbamoyl etc.), (ix) $C_{1-6}$ alkylsulfonyl (e.g., methylsulfonyl, ethylsulfonyl etc.), (x) $C_{1-6}$ alkyl-carbonylamino (e.g., acetylamino etc.) and (xi) $C_{1-6}$ alkyl-carbonyl (e.g., acetyl etc.).

Preferable embodiment of $R^2$ is

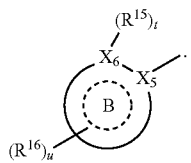

$R^{15}$ is preferably a group selected from (i) a halogen atom (e.g., a fluorine atom, a chlorine atom, a bromine atom, an iodine atom), (ii) cyano, (iii) $C_{1-6}$ alkyl (e.g., methyl, ethyl, propyl, isopropyl etc.) optionally substituted by 1 to 5 (preferably 1 to 3) halogen atoms (e.g., a fluorine atom, a chlorine atom, a bromine atom, an iodine atom), (iv) $C_{1-6}$ alkoxy (e.g., methoxy, ethoxy, propoxy, isopropoxy etc.), (v) amino optionally mono- or di-substituted by $C_{1-6}$ alkyl (e.g., methyl, ethyl, propyl, isopropyl, butyl, isobutyl, sec-butyl, tert-butyl, pentyl, hexyl etc.), (vi) carbamoyl, (vii) mono-$C_{1-6}$ alkyl-carbamoyl (e.g., methylcarbamoyl, ethylcarbamoyl etc.), (viii) di-$C_{1-6}$ alkyl-carbamoyl (e.g., dimethylcarbamoyl, diethylcarbamoyl, ethylmethylcarbamoyl etc.), (ix) $C_{1-6}$ alkylsulfonyl (e.g., methylsulfonyl, ethylsulfonyl etc.), (x) $C_{1-6}$ alkyl-carbonylamino (e.g., acetylamino etc.) and (xi) $C_{1-6}$ alkyl-carbonyl (e.g., acetyl etc.).

Of these, $R^{15}$ is preferably a group selected from (i) a halogen atom, (ii) cyano and (iii) $C_{1-6}$ alkyl optionally substituted by 1 to 5 (preferably 1 to 3) halogen atoms.

$R^{16}$ is preferably a group selected from (i) a halogen atom (e.g., a fluorine atom, a chlorine atom, a bromine atom, an iodine atom), (ii) cyano, (iii) $C_{1-6}$ alkyl (e.g., methyl, ethyl, propyl, isopropyl etc.) optionally substituted by 1 to 5 (preferably 1 to 3) halogen atoms (e.g., a fluorine atom, a chlorine atom, a bromine atom, an iodine atom), (iv) $C_{1-6}$ alkoxy (e.g., methoxy, ethoxy, propoxy, isopropoxy etc.), (v) amino optionally mono- or di-substituted by $C_{1-6}$ alkyl (e.g., methyl, ethyl, propyl, isopropyl, butyl, isobutyl, sec-butyl, tert-butyl, pentyl, hexyl etc.), (vi) carbamoyl, (vii) mono-$C_{1-6}$ alkyl-carbamoyl (e.g., methylcarbamoyl, ethylcarbamoyl etc.), (viii) di-$C_{1-6}$ alkyl-carbamoyl (e.g., dimethylcarbamoyl, diethylcarbamoyl, ethylmethylcarbamoyl etc.), (ix) $C_{1-6}$ alkylsulfonyl (e.g., methylsulfonyl, ethylsulfonyl etc.), (x) $C_{1-6}$ alkyl-carbonylamino (e.g., acetylamino etc.) and (xi) $C_{1-6}$ alkyl-carbonyl (e.g., acetyl etc.).

$R^3$ is particularly preferably a group selected from (i) a halogen atom, (ii) cyano, (iii) $C_{1-6}$ alkyl optionally substituted by 1 to 5 (preferably 1 to 3) halogen atoms and (iv) $C_{1-6}$ alkoxy.

The partial structure of compound (I) or (I'):

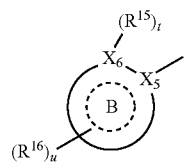

is preferably

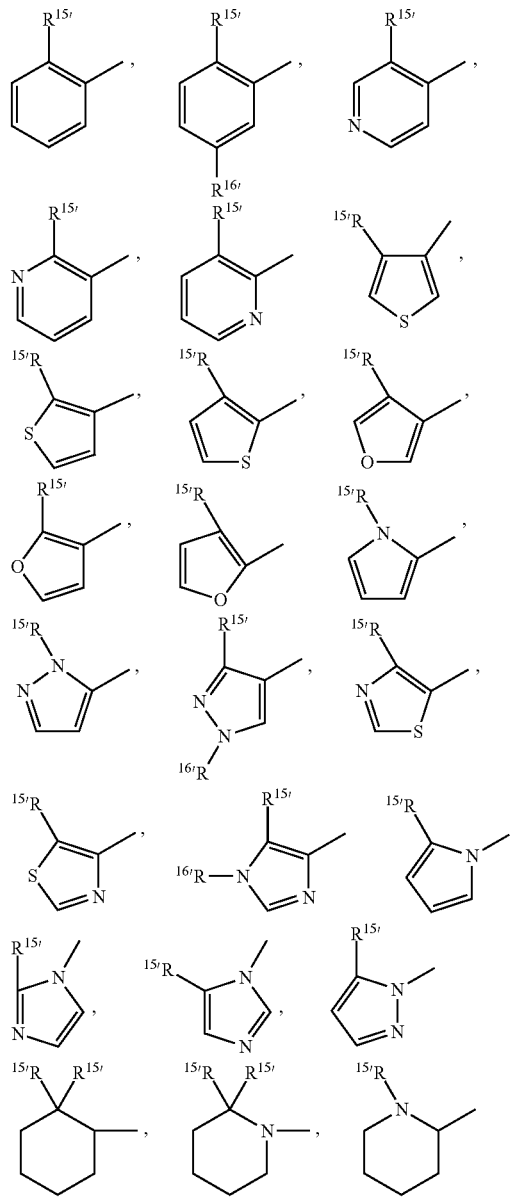

-continued

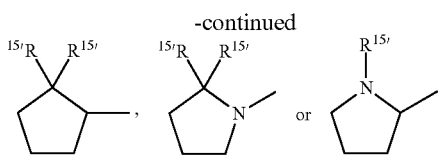

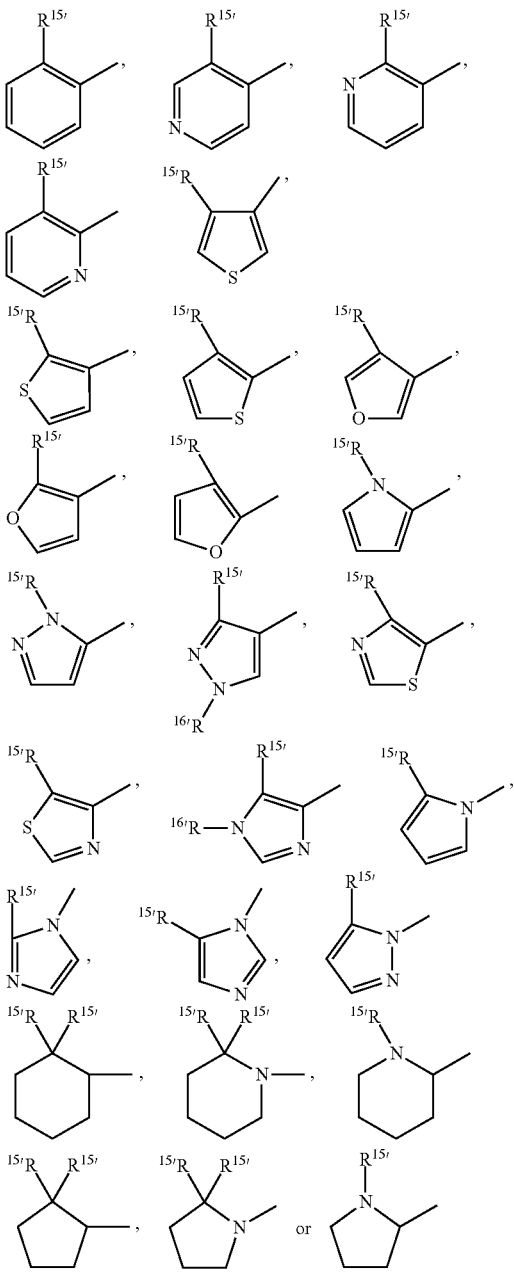

wherein R s a hydrogen atom or $R^{15}$, $R^{16}$, is a hydrogen atom or $R^{16}$. Here, $R^{15}$ and $R^{16}$ are as defined above.

The partial structure is more preferably wherein each symbol is as defined above.

In another embodiment, as $R^2$, a $C_{6-14}$ aryl group or a 5- or 6-membered aromatic heterocyclic group each optionally substituted by 1 to 3 halogen atoms is preferable.

Particularly, phenyl and 1-, 2-, 3- or 4-pyridyl each optionally substituted by 1 to 3 halogen atoms (particularly, a fluorine atom, a chlorine atom) are preferable.

$R^3$ and $R^4$ are preferably each independently a hydrogen atom or $C_{1-6}$ alkyl, particularly preferably a hydrogen atom or methyl.

A preferable embodiment of the partial structure in compound (I):

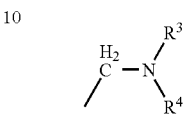

is an aminomethyl group (—$CH_2$—$NH_2$), a methylaminomethyl group (—$CH_2$—$NH(CH_3)$), a dimethylaminomethyl group (—$CH_2$—$N(CH_3)_2$) or a nitrogen-containing heterocyclyl-methyl group optionally substituted by hydroxy (e.g., 3-hydroxy-1-azetidinylmethyl), and an aminomethyl group and a methylaminomethyl group are particularly preferable.

Alternatively, $R^3$ and $R^4$ may form, together with the adjacent nitrogen atom, optionally substituted nitrogen-containing heterocycle.

As the "optionally substituted nitrogen-containing heterocycle" formed by $R^3$ and $R^4$ together with the adjacent nitrogen atom, 3-hydroxyazetidine is preferable.

In compound (I'), preferable $R^{13}$ and $R^{14}$ are each a hydrogen atom, a halogen atom, a $C_{1-3}$ alkyl group or a cyano group. Among these, a hydrogen atom and a halogen atom (particularly, a chlorine atom) are preferable. In addition, in compound (I'), a and b are each preferably 0 or 1.

Preferable embodiments of the aforementioned Y and each substituent can be optionally combined.

As specific examples of compound (I), preferable embodiments are shown as the following compounds (Ia-1)-(Ia-42).

(Ia-1)
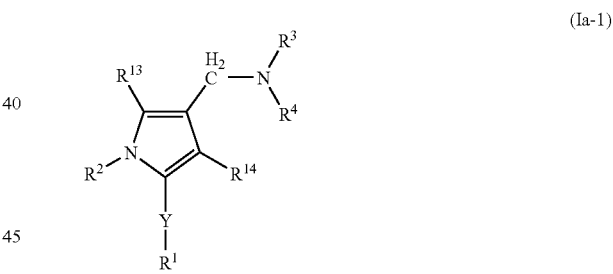

(Ia-2)
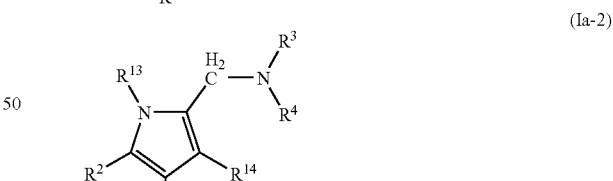

(Ia-3)
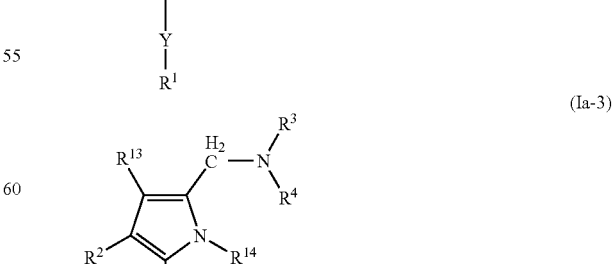

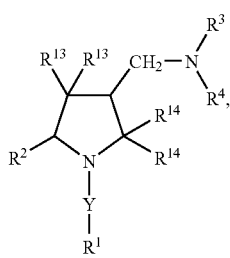 (Ia-4)
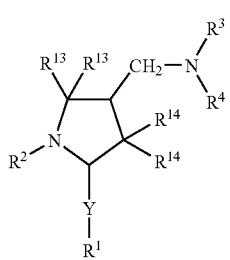 (Ia-5)
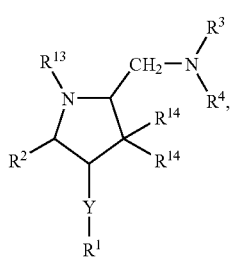 (Ia-6)
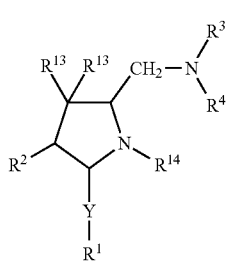 (Ia-7)
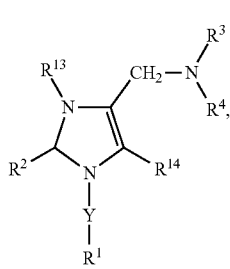 (Ia-8)
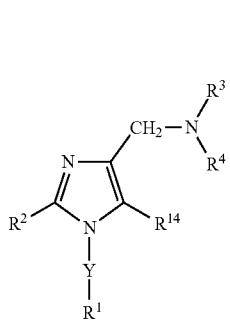 (Ia-9)
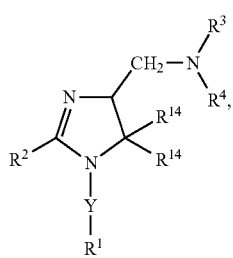 (Ia-10)
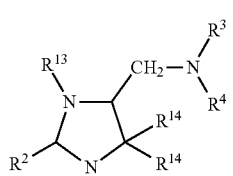 (Ia-11)
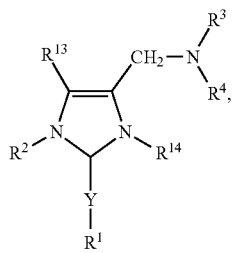 (Ia-12)
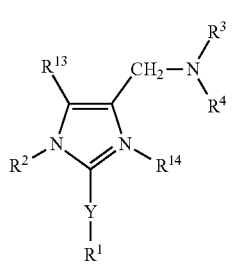 (Ia-13)
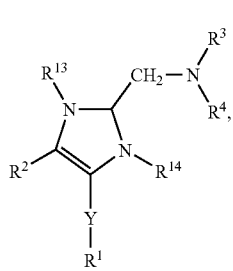 (Ia-14)
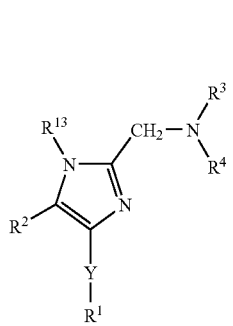 (Ia-15)

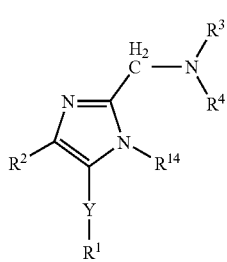 (Ia-16)
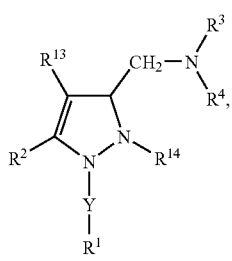 (Ia-17)
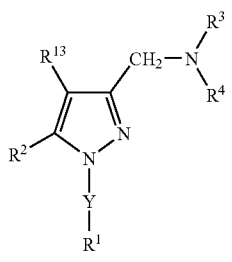 (Ia-18)
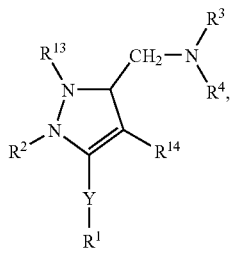 (Ia-19)
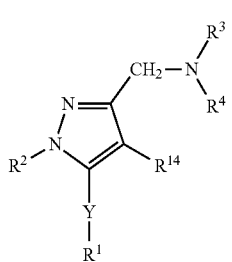 (Ia-20)
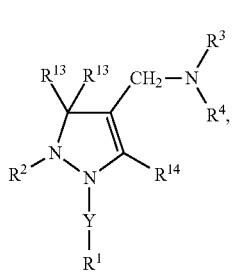 (Ia-21)
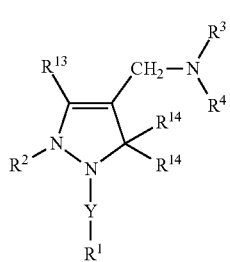 (Ia-22)
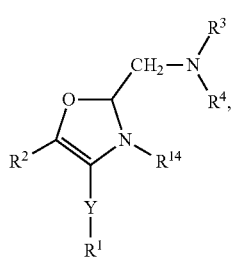 (Ia-23)
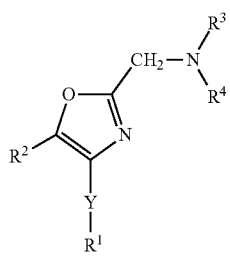 (Ia-24)
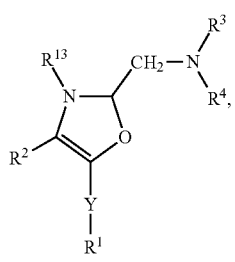 (Ia-25)
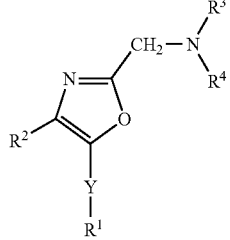 (Ia-26)
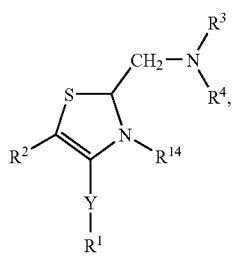 (Ia-27)

(Ia-28) 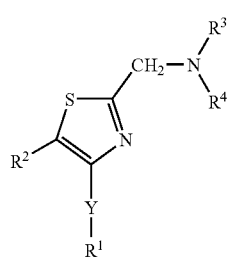
(Ia-29) 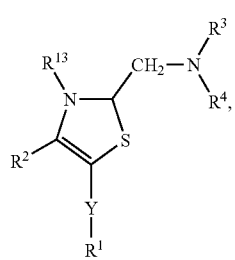
(Ia-30) 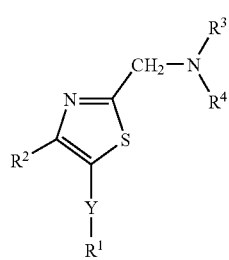
(Ia-31) 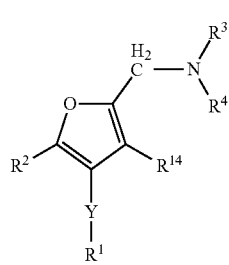
(Ia-32) 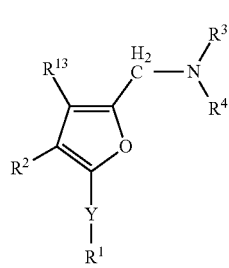
(Ia-33) 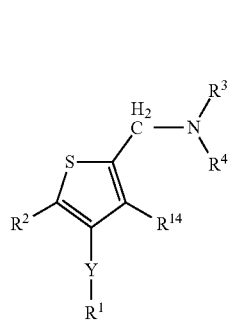
(Ia-34) 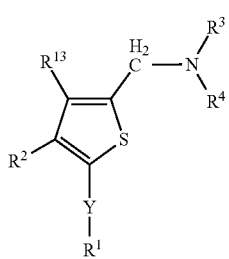
(Ia-35) 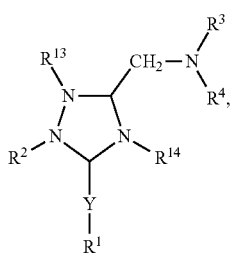
(Ia-36) 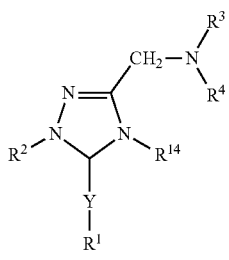
(Ia-37) 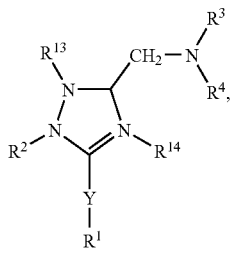
(Ia-38) 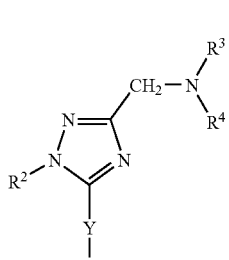
(Ia-39) 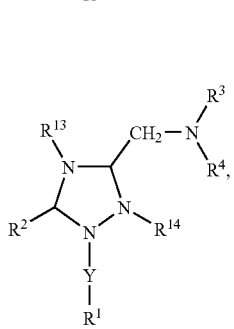

-continued

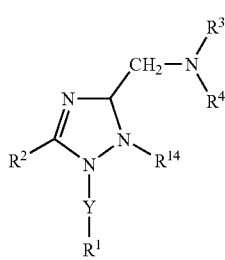
(Ia-40)

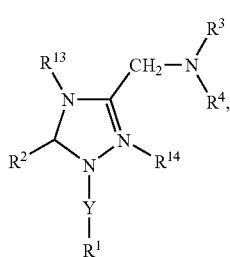
(Ia-41)

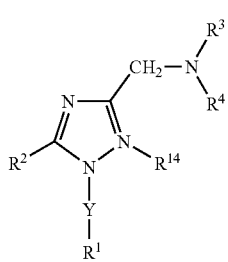
(Ia-42)

wherein each symbol in the formulas of the above-mentioned compounds (Ia-1) to (Ia-42) is as defined above.

Compound (I) wherein the partial structure in the formula (I)

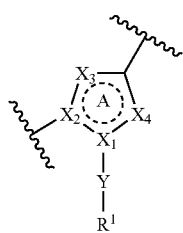

is

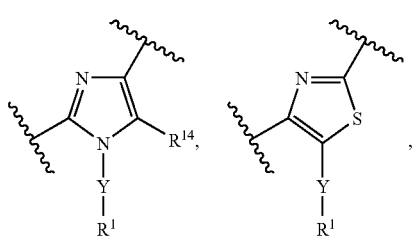

-continued

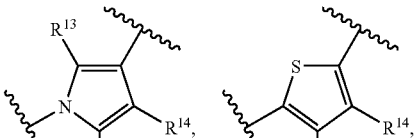

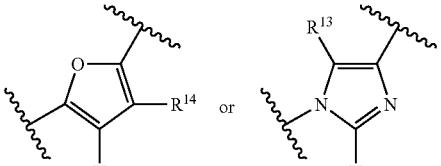

wherein each symbol is as defined above, is preferable.

Among the above-mentioned compounds, compounds (Ia-1), (Ia-9), (Ia-13), (Ia-20), (Ia-30), (Ia-31), (Ia-33) and (Ia-34) are preferable. Particularly, a compound of the formula (I) wherein the partial structure

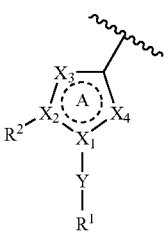

is

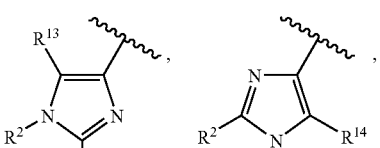

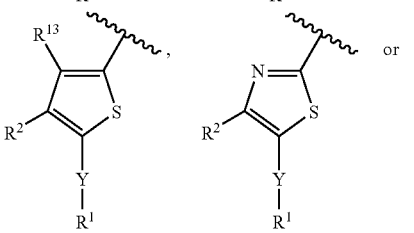

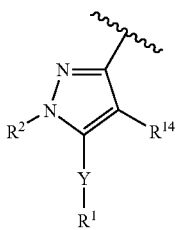

wherein each symbol is as defined above, (i.e., compounds (Ia-9), (Ia-13), (Ia-20), (Ia-30) and (Ia-34)) is preferable, and

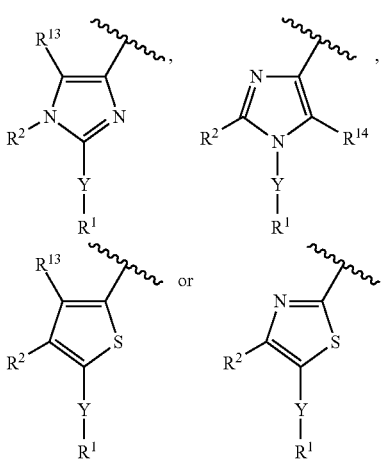

wherein each symbol is as defined above, (i.e., compounds (Ia-9), (Ia-13), (Ia-30) and (Ia-34)) is particularly preferable.

More preferable embodiments of compounds (Ia-1), (Ia-9), (Ia-13), (Ia-20), (Ia-30), (Ia-31), (Ia-33) and (Ia-34) are shown in the following.

(1) Compound (Ia-1)

A compound represented by

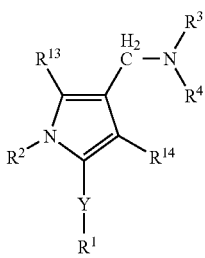

(Ia-1)

wherein $R^1$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from (i) a halogen atom, (ii) hydroxy, (iii) cyano, (iv) $C_{1-6}$ alkyl optionally substituted by 1-5 (preferably 1-3) halogen atoms, (v) $C_{1-6}$ alkoxy optionally substituted by 1-5 (preferably 1-3) halogen atoms, (vi) amino optionally mono- or di-substituted by $C_{1-6}$ alkyl, (vii) oxo, (viii) carbamoyl, (ix) mono-$C_{1-6}$alkyl-carbamoyl, (x) di-$C_{1-6}$alkyl-carbamoyl, (xi) $C_{1-6}$ alkylsulfonyl and (xii) $C_{1-6}$ alkyl-carbonylamino;

$R^2$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from a halogen atom, a cyano group, a trifluoromethyl group, a methyl group, an ethyl group and a methoxy group;

$R^3$ and $R^4$ are the same or different and each is a hydrogen atom or a methyl group;

$R^{13}$ and $R^{14}$ are the same or different and each is a hydrogen atom, a halogen atom, a methyl group or a cyano group; and Y is —$CH_2$—, —$CH(CH_3)$—, —$C(CH_3)_2$—, —O—, —NH—, —$N(CH_3)$—, —S—, —SO—, —$SO_2$—$CH_2$—, —$SO_2$—$C(CH_3)_2$—, —$SO_2$—NH— or —$SO_2$—N($CH_3$)—, or a salt thereof.

(2) Compound (Ia-9)

A compound represented by

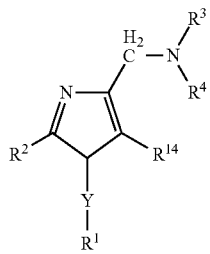

(Ia-9)

wherein $R^1$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl), a piperidyl group (e.g., 1-, 2-, 3- or 4-piperidyl) or a pyrimidinyl group (e.g., 1-, 2-, 4- or 5-pyrimidinyl), each of which is optionally substituted by 1 to 3 substituents selected from (i) a halogen atom, (ii) hydroxy, (iii) cyano, (iv) $C_{1-6}$ alkyl optionally substituted by 1-5 (preferably 1-3) halogen atoms, (v) $C_{1-6}$ alkoxy optionally substituted by 1-5 (preferably 1-3) halogen atoms, (vi) amino optionally mono- or di-substituted by $C_{1-6}$ alkyl, (vii) oxo, (viii) carbamoyl, (ix) mono-$C_{1-6}$alkyl-carbamoyl, (x) di-$C_{1-6}$alkyl-carbamoyl, (xi) $C_{1-6}$ alkylsulfonyl and (xii) $C_{1-6}$ alkyl-carbonylamino;

$R^2$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from a halogen atom, a cyano group, a trifluoromethyl group, a methyl group, an ethyl group and a methoxy group;

$R^3$ and $R^4$ are the same or different and each is a hydrogen atom or a methyl group;

$R^{14}$ is a hydrogen atom, a halogen atom, a methyl group or a cyano group;

Y is a bond, —$CH_2$—, —$CH(CH_3)$—, —$C(CH_3)_2$—, —CH($CH_2OH$)—, —$CH(CO_2CH_3)$—, —O—, —NH—, —N($CH_3$)—, —S—, —S—$CH_2$—, —SO—, —$SO_2$—$CH_2$—, —$SO_2$—$C(CH_3)_2$—, —$SO_2$—NH— or —$SO_2$—N($CH_3$)—, or a salt thereof.

(2') A particularly preferable embodiment of compound (Ia-9) is, for example, a compound represented by

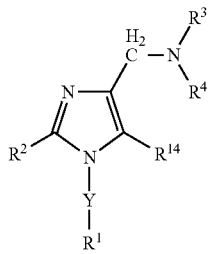

(Ia-9)

wherein $R^1$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from (i) a halogen atom, (ii) hydroxy, (iii) cyano, (iv) $C_{1-6}$ alkyl optionally substituted by 1-5 (preferably 1-3) halogen atoms, (v) $C_{1-6}$ alkoxy optionally substituted by 1-5 (preferably 1-3) halogen atoms, (vi) amino optionally mono- or di-substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino;

$R^2$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3-or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from a halogen atom, a cyano group, a trifluoromethyl group, a methyl group, an ethyl group and a methoxy group;

$R^3$ and $R^4$ are the same or different and each is a hydrogen atom or a methyl group;

$R^{14}$ is a hydrogen atom, a halogen atom, a methyl group or a cyano group; and Y is —$CH_2$—, —$CH(CH_3)$—, —$C(CH_3)_2$—, —O—, —NH—, —N($CH_3$)—, —S—, —SO—, —$SO_2$—$CH_2$—, —$SO_2$—$C(CH_3)_2$—, —$SO_2$—NH— or —$SO_2$—N($CH_3$)—, or a salt thereof.

(3) Compound (Ia-13)

A compound represented by

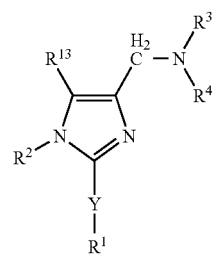

(Ia-13)

wherein $R^1$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from (i) a halogen atom, (ii) hydroxy, (iii) cyano, (iv) $C_{1-6}$ alkyl optionally substituted by 1-5 (preferably 1-3) halogen atoms, (v) $C_{1-6}$ alkoxy optionally substituted by 1-5 (preferably 1-3) halogen atoms, (vi) amino optionally mono- or di-substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino;

$R^2$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from a halogen atom, a cyano group, a trifluoromethyl group, a methyl group, an ethyl group and a methoxy group;

$R^3$ and $R^4$ are the same or different and each is a hydrogen atom or a methyl group;

$R^{13}$ is a hydrogen atom, a halogen atom, a methyl group or a cyano group; and Y is —$CH_2$—, —$CH(CH_3)$—, —$C(CH_3)_2$—, —O—, —NH—, —N($CH_3$)—, —S—, —SO—, —$SO_2$—$CH_2$—, —$SO_2$—$C(CH_3)_2$—, —$SO_2$—NH— or —$SO_2$—N($CH_3$)—, or a salt thereof.

(4) Compound (Ia-20)

A compound represented by

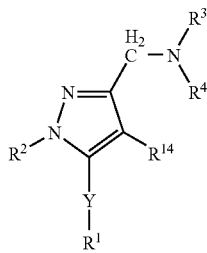

(Ia-20)

wherein $R^1$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from (i) a halogen atom, (ii) hydroxy, (iii) cyano, (iv) $C_{1-6}$ alkyl optionally substituted by 1-5 (preferably 1-3) halogen atoms, (v) $C_{1-6}$ alkoxy optionally substituted by 1-5 (preferably 1-3) halogen atoms, (vi) amino optionally mono- or di-substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino;

$R^2$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from a halogen atom, a cyano group, a trifluoromethyl group, a methyl group, an ethyl group and a methoxy group;

$R^3$ and $R^4$ are the same or different and each is a hydrogen atom or a methyl group;

$R^{14}$ is a hydrogen atom, a halogen atom, a methyl group or a cyano group; and Y is —$CH_2$—, —$CH(CH_3)$—, —$C(CH_3)_2$—, —O—, —NH—, —$N(CH_3)$—, —N(CO (CH_3))—, —S—, —SO—, —$SO_2$—$CH_2$—, —$SO_2$—$C(CH_3)_2$—, —$SO_2$—NH— or —$SO_2$—$N(CH_3)$—, or a salt thereof.

(4') A more preferable embodiment of compound (Ia-20) is, for example, a compound represented by

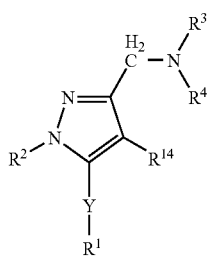

(Ia-20)

wherein $R^1$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from (i) a halogen atom, (ii) hydroxy, (iii) cyano, (iv) $C_{1-6}$ alkyl optionally substituted by 1-5 (preferably 1-3) halogen atoms, (v) $C_{1-6}$ alkoxy optionally substituted by 1-5 (preferably 1-3) halogen atoms, (vi) amino optionally mono- or di-substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino;

$R^2$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from a halogen atom, a cyano group, a trifluoromethyl group, a methyl group, an ethyl group and a methoxy group;

$R^3$ and $R^4$ are the same or different and each is a hydrogen atom or a methyl group;

$R^{14}$ is a hydrogen atom, a halogen atom, a methyl group or a cyano group; and Y is —$CH_2$—, —$CH(CH_3)$—, —$C(CH_3)_2$—, —O—, —NH—, —$N(CH_3)$—, —S—, —SO—, —$SO_2$—$CH_2$—, —$SO_2$—$C(CH_3)_2$—, —$SO_2$—NH— or —$SO_2$—N(CH_3)—, or a salt thereof.

(5) Compound (Ia-30)

A compound represented by

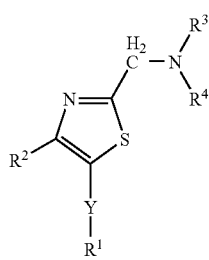

(Ia-30)

wherein $R^1$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from (i) a halogen atom, (ii) hydroxy, (iii) cyano, (iv) $C_{1-6}$ alkyl optionally substituted by 1-5 (preferably 1-3) halogen atoms, (v) $C_{1-6}$ alkoxy optionally substituted by 1-5 (preferably 1-3) halogen atoms, (vi) amino optionally mono- or di-substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino;

$R^2$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from a halogen atom, a cyano group, a trifluoromethyl group, a methyl group, an ethyl group and a methoxy group;

$R^3$ and $R^4$ are the same or different and each is a hydrogen atom or a methyl group; and Y is —$CH_2$—, —$CH(CH_3)$—, —$C(CH_3)_2$—, —O—, —NH—, —$N(CH_3)$—, —S—, —SO—, —$SO_2$—$CH_2$—, —$SO_2$—$C(CH_3)_2$—, —$SO_2$—NH— or —$SO_2$—N($CH_3$)—, or a salt thereof.

(6) Compound (Ia-31)

A compound represented by

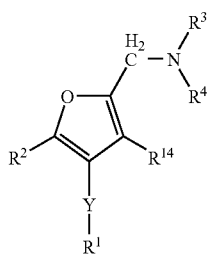

(Ia-31)

wherein $R^1$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from (i) a halogen atom, (ii) hydroxy, (iii) cyano, (iv) $C_{1-6}$ alkyl optionally substituted by 1-5 (preferably 1-3) halogen atoms, (v) $C_{1-6}$ alkoxy optionally substituted by 1-5 (preferably 1-3) halogen atoms, (vi) amino optionally mono- or di-substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino;

$R^2$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from a halogen atom, a cyano group, a trifluoromethyl group, a methyl group, an ethyl group and a methoxy group;

$R^3$ and $R^4$ are the same or different and each is a hydrogen atom or a methyl group;

$R^{14}$ is a hydrogen atom, a halogen atom, a methyl group or a cyano group; and Y is —$CH_2$—, —$CH(CH_3)$—, —$C(CH_3)_2$—, —O—, —NH—, —$N(CH_3)$—, —S—, —SO—, —$SO_2$—$CH_2$—, —$SO_2$—$C(CH_3)_2$—, —$SO_2$—NH— or —$SO_2$—N($CH_3$)—, or a salt thereof.

(7) Compound (Ia-33)

A compound represented by

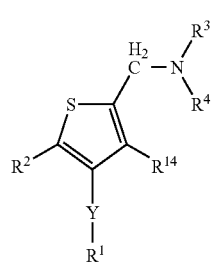

(Ia-33)

wherein $R^1$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from (i) a halogen atom, (ii) hydroxy, (iii) cyano, (iv) $C_{1-6}$ alkyl optionally substituted by 1-5 (preferably 1-3) halogen atoms, (v) $C_{1-6}$ alkoxy optionally substituted by 1-5 (preferably 1-3) halogen atoms, (vi) amino optionally mono- or di-substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino;

$R^2$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from a halogen atom, a cyano group, a trifluoromethyl group, a methyl group, an ethyl group and a methoxy group;

$R^3$ and $R^4$ are the same or different and each is a hydrogen atom or a methyl group;

$R^{14}$ is a hydrogen atom, a halogen atom, a methyl group or a cyano group; and Y is —$CH_2$—, —$CH(CH_3)$—, —$C(CH_3)_2$—, —O—, —NH—, —$N(CH_3)$—, —S—, —SO—, —$SO_2$—$CH_2$—, —$SO_2$—$C(CH_3)_2$—, —$SO_2$—NH— or —$SO_2$—N($CH_3$)—, or a salt thereof.

(8) Compound (Ia-34)

A compound represented by

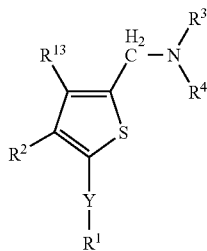

(Ia-34)

wherein $R^1$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from (i) a halogen atom, (ii) hydroxy, (iii) cyano, (iv) $C_{1-6}$ alkyl optionally substituted by 1-5 (preferably 1-3) halogen atoms, (v) $C_{1-6}$ alkoxy optionally substituted by 1-5 (preferably 1-3) halogen atoms, (vi) amino optionally mono- or di-substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino;

$R^2$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from a halogen atom, a cyano group, a trifluoromethyl group, a methyl group, an ethyl group and a methoxy group;

$R^3$ and $R^4$ are the same or different and each is a hydrogen atom or a methyl group, or $R^3$ and $R^4$ may form, together with the adjacent nitrogen atom, nitrogen-containing heterocycle optionally substituted by hydroxy (e.g., 3-hydroxy-1-azetidinyl);

$R^{13}$ is a hydrogen atom, a halogen atom, a methyl group or a cyano group; and Y is —$CH_2$—, —$CH(CH_3)$—, —$C(CH_3)_2$—, —CO—, —CH(OH)—, —O—, —NH—, —$N(CH_3)$—, —S—, —SO—, —$SO_2$—$CH_2$—, —$SO_2$—$C(CH_3)_2$—, —$SO_2$— NH— or —$SO_2$13 $N(CH_3)$—, or a salt thereof.

(8') A particularly preferable embodiment of compound (Ia-34) is, for example, a compound represented by

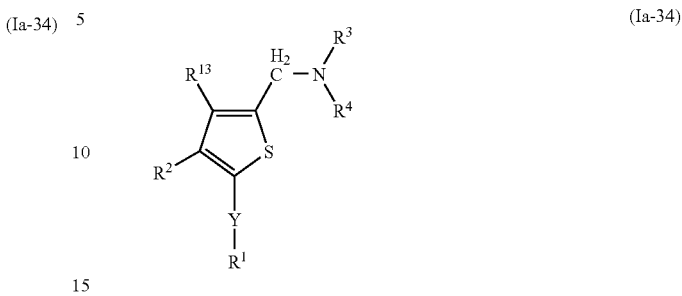

(Ia-34)

wherein $R^1$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from (i) a halogen atom, (ii) hydroxy, (iii) cyano, (iv) $C_{1-6}$ alkyl optionally substituted by 1-5 (preferably 1-3) halogen atoms, (v) $C_{1-6}$ alkoxy optionally substituted by 1-5 (preferably 1-3) halogen atoms, (vi) amino optionally mono- or di-substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino;

$R^2$ is a phenyl group, a cyclopentyl group, a cyclohexyl group, a pyrrolyl group (e.g., 1-, 2- or 3-pyrrolyl), a pyrazolyl group (e.g., 1-, 3-, 4- or 5-pyrazolyl), a thiazolyl group (e.g., 2-, 4- or 5-thiazolyl), an imidazolyl group (e.g., 1-, 2-, 4- or 5-imidazolyl), an oxazolyl group (e.g., 2-, 4- or 5-oxazolyl), a thienyl group (e.g., 2- or 3-thienyl), a furyl group (e.g., 2- or 3-furyl), a pyridyl group (e.g., 1-, 2-, 3- or 4-pyridyl), a pyrrolidinyl group (e.g., 1-, 2- or 3-pyrrolidinyl) or a piperidyl group (e.g., 1-, 2-, 3- or 4-piperidyl), each of which is optionally substituted by 1 to 3 substituents selected from a halogen atom, a cyano group, a trifluoromethyl group, a methyl group, an ethyl group and a methoxy group;

$R^3$ and $R^4$ are each a hydrogen atom or a methyl group;

$R^{13}$ is a hydrogen atom, a halogen atom, a methyl group or a cyano group; and Y is —$CH_2$—, —$CH(CH_3)$—, —$C(CH_3)_2$—, —O—, —NH—, —$N(CH_3)$—, —S—, —SO—, —$SO_2$—$CH_2$—, —$SO_2$—$C(CH_3)_2$—, —$SO_2$—NH— or —$SO_2$—N($CH_3$)—, or a salt thereof.

Examples of the salt of compound (I) include metal salts, ammonium salts, salts with organic bases, salts with inorganic acids, salts with organic acids, salts with basic or acidic amino acids and the like. Preferable examples of metal salt include alkali metal salts such as sodium salt, potassium salt and the like; alkaline earth metal salts such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysin, ornithine and the like. Preferable examples of the salt with acidic amino acid include a salt with aspartic acid, glutamic acid and the like.

The compounds (II)-(XX) in the schemes may form salts, and as such salts, for example, those similar to the salts of compound (I) can be mentioned.

While the compounds obtained in respective steps can be used for the next reaction in the form of a reaction mixture or a crude product, they can also be easily isolated and purified from the reaction mixture by a known separation and purification means, such as recrystallization, distillation, chromatography and the like.

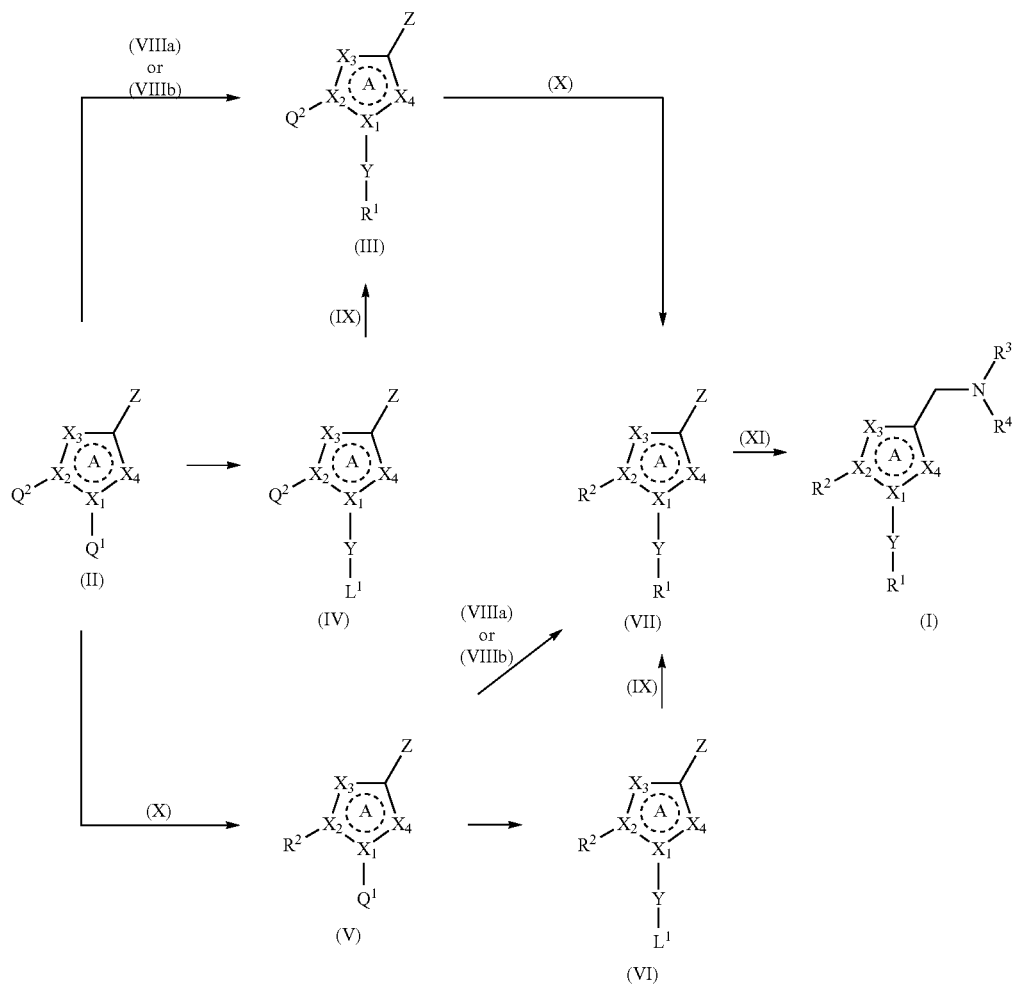

Of these, pharmaceutically acceptable salts are preferable. For example, when a compound contains an acidic functional group, inorganic salts such as alkali metal salt (e.g., sodium salt, potassium salt etc.), alkaline earth metal salt (e.g., calcium salt, magnesium salt, barium salt etc.) and the like, ammonium salts and the like; and when a compound contains a basic functional group, for example, salts with inorganic acid such as hydrochloric acid, hydrobromic acid, nitric acid, sulfuric acid, phosphoric acid and the like, or salts with organic acid such as acetic acid, phthalic acid, fumaric acid, oxalic acid, tartaric acid, maleic acid, citric acid, succinic acid, methanesulfonic acid, p-toluenesulfonic acid and the like.

The production methods of compound (I) of the present invention are explained.

wherein $Q^1$ and $Q^2$ are the same or different and each is a hydrogen atom, a leaving group such as a halogen atom (e.g., a fluorine atom, a chlorine atom, a bromine atom, an iodine atom), a trifluoromethanesulfonyloxy group, a p-toluenesulfonyloxy group and the like, or a functional group such as a hydroxy group, an amino group, a mercapto group and the like; Z is a hydrogen atom, a formyl group, a carboxyl group, an ester group, a cyano group or an alkylaminocarbonyl group and the like; $L^1$ is a hydrogen atom, hydroxy group, alkoxy group, a halogen atom (e.g., a fluorine atom, a chlorine atom, a bromine atom, an iodine atom) and the like; and other symbols are as defined above.

Compound (II) may be a commercially available product, or can be produced according to a method known per se, for example, the method described in Heterocycles, vol. 38, page 959 (1994), WO2004/7504 and the like, or a method analogous thereto.

Compound (III) can be produced by reacting compound (II) with a compound represented by the formula (VIIIa)

wherein $L^2$ is a hydrogen atom, or a leaving group such as a halogen atom (e.g., a fluorine atom, a chlorine atom, a bromine atom, an iodine atom), a metal such as sodium, potassium and the like, a dialkylamino group, a trifluoromethanesulfonyloxy group, a p-toluenesulfonyloxy group and the like, and other symbols are as defined above, or according to the method described in Synlett, vol. 15, page 2331 (2007), or a method analogous thereto.

This reaction is advantageously carried out using a solvent inert to the reaction. The solvent is not particularly limited as long as the reaction proceeds. Preferable examples thereof include hydrocarbons such as benzene, toluene and the like, ethers such as tetrahydrofuran and the like, amides such as N,N-dimethylformamide, N,N-dimethylacetamide and the like, aromatic amines such as pyridine, lutidine and the like, and the like, and a mixed solvent thereof and the like.

The reaction is advantageously carried out using a base. Examples of the base include inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, organic lithiums such as n-butyllithium, sec-butyllithium and the like, metal amides such as lithium diisopropylamide, potassium hexamethyl disilazide and the like. The amount of the base to be used is 0.8 to 10 mol, preferably 1 to 5 mol, per 1 mol of compound (II).

While the reaction time varies depending on the reagents and solvent to be used, it is generally about 1 min to about 48 hr, preferably about 10 min to about 24 hr.

The reaction temperature is generally about −78° C. to about 180° C., preferably about −78° C. to about 100° C.

Alternatively, compound (III) can be produced by reacting compound (II) with a compound represented by the formula (VIIIb)

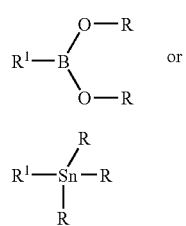

or

wherein $R^1$ and Y are as defined above, and R is an alkyl group or allyl group,
(compound VIIIb1-3 are sometimes correctively to be abbreviated as compound VIIIb), according to the method described in Synthetic Communications, vol. 11, page 513 (1981), Synthesis, vol.7, pages 564-565 (1986), or Journal of Organic Chemistry (J. Org. Chem.), vol. 68, page 2861 (2003), or a method analogous thereto.

Alternatively, compound (III) can be produced by subjecting the below-mentioned compound (IV) to a substitution reaction, a condensation reaction or a reductive amination reaction with a compound represented by the formula (IX)

or

wherein each symbol is as defined above.
(compound IX-1 and 2 are sometimes correctively to be abbreviated as compound IX).

In substitution reaction, the use of base is effective. Examples of the base include inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like. The amount of the base to be used is 0.8 to 10 mol, preferably 1 to 5 mol, per 1 mol of compound (IV).

This reaction is advantageously carried out using a solvent inert to the reaction. The solvent is not particularly limited as long as the reaction proceeds. Preferable examples thereof include hydrocarbons such as benzene, toluene and the like, ethers such as tetrahydrofuran, diethyl ether and the like, amides such as N,N-dimethylformamide, N,N-dimethylacetamide and the like, halogenated hydrocarbons such as dichloromethane and the like, and the like, and a mixed solvent thereof and the like.

While the reaction time varies depending on the reagents and solvent to be used, it is generally 1 min to 48 hr, preferably 10 min to 24 hr.

The reaction temperature is generally −20° C. to 180° C., preferably −20° C. to 100° C.

In condensation reaction, examples of the condensing agent to be used include 1-ethyl-3-(3-dimethylaminopropyl)carbodiimide hydrochloride, carbonyldiimidazole and the like. The amount of the condensing agent to be used is 1 to 10 mol, preferably 1 to 3 mol, per 1 mol of compound (IV). In addition, the use of base is effective for the reaction. Examples of the base include 1-hydroxybenzotriazole hydrate, N,N-dimethylaminopyridine and the like. The amount of the base to be used is 0.1 to 10 mol, preferably 0.1 to 5 mol, per 1 mol of compound (IV).

This reaction is advantageously carried out using a solvent inert to the reaction. The solvent is not particularly limited as long as the reaction proceeds. Preferable examples thereof include hydrocarbons such as benzene, toluene and the like, ethers such as tetrahydrofuran, diethyl ether and the like, amides such as N,N-dimethylformamide, N,N-dimethylacetamide and the like, halogenated hydrocarbons such as dichloromethane and the like, and the like, and a mixed solvent thereof and the like.

While the reaction time varies depending on the reagents and solvent to be used, it is generally 1 min to 48 hr, preferably 10 min to 24 hr.

The reaction temperature is generally −20° C. to 180° C., preferably −20° C. to 100° C.

In reductive amination reaction, compound (III) can be produced according to the method described in Shinjikken Kagaku Koza (Courses in Experimental Chemistry), vol. 14-III, pages 1380-1385 (Maruzen Press) or the like.

Compound (IV) can be produced by reacting compound (II) with an organic lithium such as n-butyllithium, sec-butyllithium and the like, or a metal amide such as lithium diisopropylamide, potassium hexamethyl disilazide and the like, and then reacting an electrophile such as N,N-dimethylformamide, carbon dioxide gas, sulfuryl chloride, ethyl cyanoformate and the like. The amount of the electrophile to be used is 1 to 100 mol, preferably 1 to 10 mol, per 1 mol of compound (II).

This reaction is advantageously carried out using a solvent inert to the reaction. The solvent is not particularly limited as long as the reaction proceeds. Preferable examples thereof include aromatic hydrocarbons such as benzene, toluene and the like, ethers such as tetrahydrofuran, diethyl ether and the like, halogenated hydrocarbons such as dichloromethane and the like, and the like, and a mixed solvent thereof and the like.

While the reaction time varies depending on the reagents and solvent to be used, it is generally 1 min to 48 hr, preferably 10 min to 16 hr.

The reaction temperature is generally −78° C. to 100° C., preferably −78° C. to 25° C.

Compound (V) can be produced according to a method known per se, for example, the method described in Bioorganic and Medicinal Chemistry Letters (Bioorg. Med. Chem. Lett.), vol. 16, page 731 (2006), Chemical and Pharmaceutical Bulletin (Chem. Pharm. Bull.), vol.31, page 1228 (1981), WO2004/98589 and the like, or a method analogous thereto.

Alternatively, Compound (V) can be produced by reacting compound (II) with a compound represented by the formula (X)

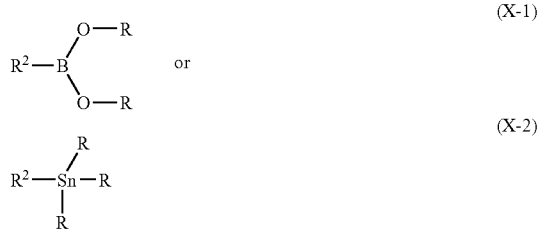

wherein each symbol is as defined above)
(compound X-1 and 2 are sometimes correctively to be abbreviated as compound X) according to the method described in Synthetic Communications, vol. 11, page 513 (1981), or Synthesis, vol. 7, pages 564-565 (1986), or a method analogous thereto.

Compound (VI) can be produced from compound (V) in the same manner as in the production method of compound (IV) from compound (II), or a method analogous thereto.

Compound (VII) can be produced from compound (III) in the same manner as in the production method of compound (V) from compound (II), from compound (V) in the same manner as in the production method of compound (III) from compound (II), or from compound (VI) in the same manner as in the production method of compound (III) from compound (IV), or a method analogous thereto.

When Z group of compound (VII) is a hydrogen atom, an ester group, a carboxyl group or a cyano group, compound (I) can be produced by converting the group to a formyl group, and then subjecting the obtained compound to a reductive amination reaction with a compound represented by the formula (XI)

wherein each symbol is as defined above,
according to the method described in Shinjikken Kagaku Koza (Courses in Experimental Chemistry), vol. 14-III, pages 1380-1385 (Maruzen Press) or the like.

When Z group is a hydrogen atom, the group can be converted to a formyl group according to the method described in Bioorg. Med. Chem., vol. 12, page 1221 (2004), Heterocycles, vol. 40, page 925 (1995) or the like.

When Z group is an ester group or a carboxyl group, the group can be converted to a hydroxy group by reducing compound (VII) with a reducing agent such as lithium aluminum hydride, diisobutylaluminum hydride, sodium borohydride, calcium borohydride, diborane and the like. The amount of the reducing agent to be used is 0.75 to 10 equivalents, preferably 1 to 5 equivalents, relative to compound (VII).

This reaction is advantageously carried out using a solvent inert to the reaction. The solvent is not particularly limited as long as the reaction proceeds. Preferable examples thereof include hydrocarbons such as benzene, toluene and the like, ethers such as tetrahydrofuran, diethyl ether and the like, and the like, and a mixed solvent thereof and the like.

While the reaction time varies depending on the reagents and solvent to be used, it is generally 10 min to 24 hr, preferably 30 min to 8 hr.

The reaction temperature is generally −78° C. to 100° C., preferably −78° C. to 25° C.

The converted hydroxy group can be converted to a formyl group by reacting compound (VII) with an oxidant such as chromic acid-pyridine complex, pyridinium chlorochromate, manganese dioxide, sulfur trioxide-pyridine complex, tetra-n-propylammonium perruthenate (tetra-n-propylammonium perruthenate) and the like. Preferable examples of the oxidant include manganese dioxide, sulfur trioxide-pyridine complex and tetra-n-propylammonium perruthenate. The oxidation reaction can be performed, for example, according to the method described in Synthesis, page 639 (1994).

When Z group is a cyano group, the group can be converted to a formyl group by reducing compound (VII) with diisobutylaluminum hydride or Raney-nickel. The reduction reaction can be carried out according to the method described in Shinjikken Kagaku Koza (Courses in Experimental Chemistry), vol. 14-II, pages 652-656 (Maruzen Press) or the like.

Alternatively, compound (I) can be produced by reducing compound (VII) wherein Z group is an alkylaminocarbonyl group with borane, lithium aluminum hydride or the like. The reduction reaction is carried out according to the method described in Shinjikken Kagaku Koza (Courses in Experimental Chemistry), vol. 20, pages 431-436 (Maruzen Press) and the like.

Compound (I) can also be produced according to the following method.

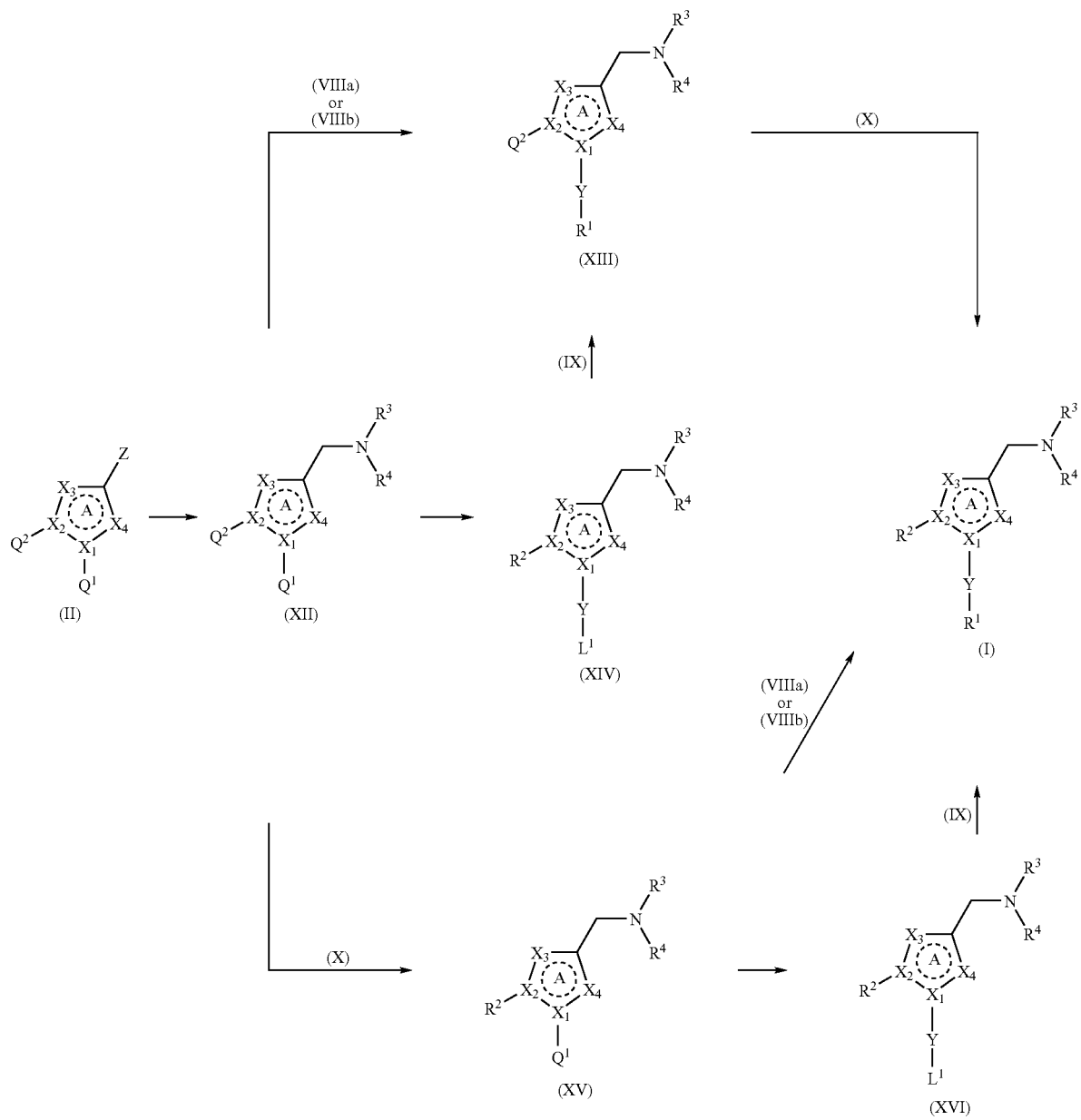

wherein each symbol is as defined above.

Compound (XII) can be produced from compound (II) in the same manner as in the production method of compound (I) from compound (VII), or a method analogous thereto.

Compound (XIII) can be produced from compound (XII) in the same manner as in the production method of compound (III) from compound (II), or a method analogous thereto. Alternatively, compound (XIII) can be produced from the below-mentioned compound (XIV) in the same manner as in the production method of compound (III) from compound (IV), or a method analogous thereto, or from compound (III) in the same manner as in the production method of compound (I) from compound (VII), or a method analogous thereto.

Compound (XIV) can be produced from compound (XII) in the same manner as in the production method of compound (IV) from compound (II), or a method analogous thereto. Alternatively, compound (XIV) can be produced from compound (IV) in the same manner as in the production method of compound (I) from compound (VII), or a method analogous thereto.

Compound (XV) can be produced from compound (XII) in the same manner as in the production method of compound (V) from compound (II), or a method analogous thereto. Alternatively, compound (XV) can be produced from compound (V) in the same manner as in the production method of compound (I) from compound (VII), or a method analogous thereto.

Compound (XVI) can be produced from compound (XV) in the same manner as in the production method of compound (IV) from compound (II), or a method analogous thereto. Alternatively, compound (XVI) can be produced from compound (VI) in the same manner as in the production method of compound (I) from compound (VII), or a method analogous thereto.

Compound (I) can be produced from compound (XIII) in the same manner as in the production method of compound (V) from compound (II), from compound (XV) in the same manner as in the production method of compound (III) from compound (II), or from compound (XVI) in the same manner as in the production method of compound (III) from compound (IV), or a method analogous thereto.

Compound (I) can also be produced according to the following method.

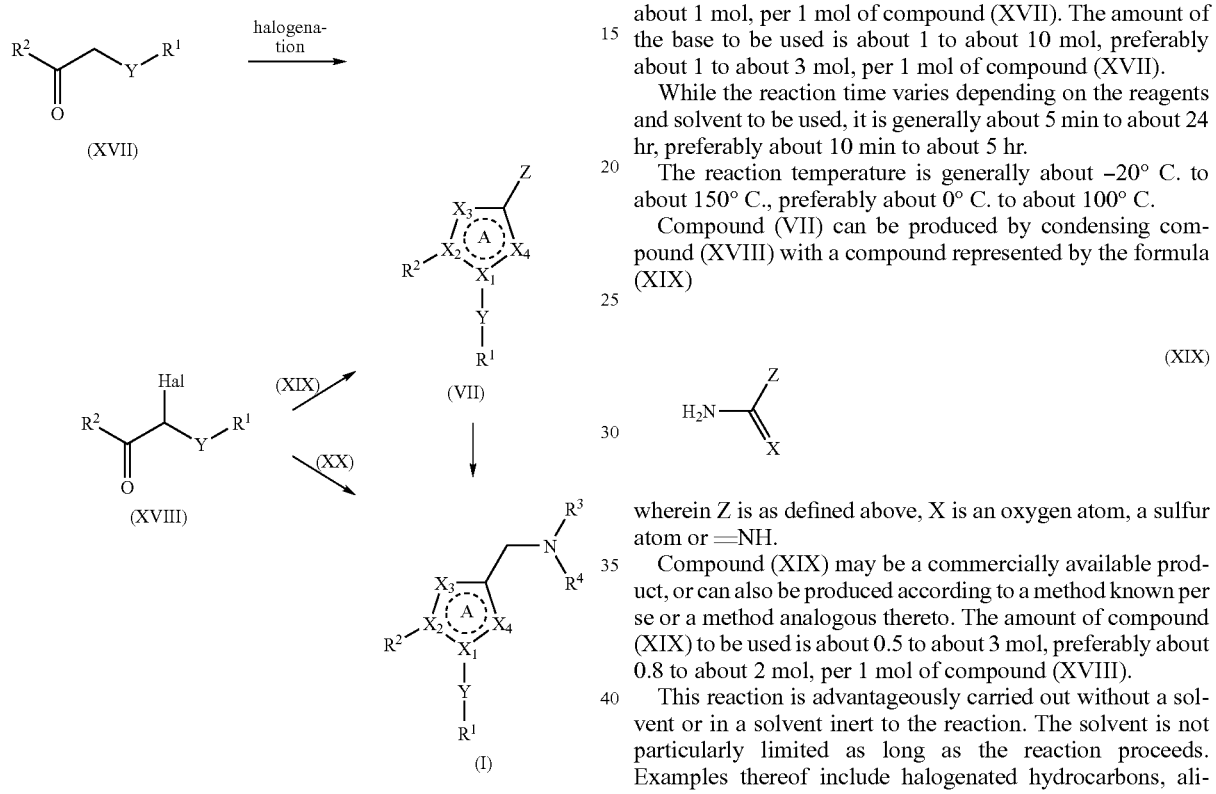

wherein Hal is a leaving group such as halogen (e.g., fluorine, chlorine, bromine, iodine) and the like, and other symbols are as defined above.

Compound (XVII) can be produced according to a method known per se, for example, the method described in Journal of Organic Chemistry (J. Org. Chem.), vol. 46, page 2596 (1981), Organic Letters (Org. Lett), vol. 3, page 1261 (2001) and the like, or a method analogous thereto.

Compound (XVIII) can be obtained by reacting compound (XVII) with a halogen (e.g., chlorine, bromine, iodine and the like), a metal halide (e.g., copper (II) bromide, copper (II) chloride and the like) and the like. The amount of the halogen or metal halide to be used is about 1 to about 5 mol, preferably about 1 to about 2 mol, per 1 mol of compound (XVII).

This reaction is advantageously carried out without a solvent or in a solvent inert to the reaction. The solvent is not particularly limited as long as the reaction proceeds. Examples thereof include ethers, esters, aromatic hydrocarbons, aliphatic hydrocarbon, amides, halogenated hydrocarbons, nitriles, sulfoxides, organic acids, aromatic amines, and a mixture of two or more solvents, and the like.

In addition, this reaction can be carried out in the presence of an acid or a base.

Examples of the acid include inorganic acids such as hydrochloric acid, hydrobromic acid and the like, and the like. Examples of the base include metal hydroxides such as sodium hydroxide, potassium hydroxide, lithium hydroxide and the like, basic salts such as sodium carbonate, potassium carbonate, cesium carbonate, sodium hydrogen carbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like. The amount of the acid to be used is about 0.01 to about 3 mol, preferably about 0.01 to about 1 mol, per 1 mol of compound (XVII). The amount of the base to be used is about 1 to about 10 mol, preferably about 1 to about 3 mol, per 1 mol of compound (XVII).

While the reaction time varies depending on the reagents and solvent to be used, it is generally about 5 min to about 24 hr, preferably about 10 min to about 5 hr.

The reaction temperature is generally about −20° C. to about 150° C., preferably about 0° C. to about 100° C.

Compound (VII) can be produced by condensing compound (XVIII) with a compound represented by the formula (XIX)

wherein Z is as defined above, X is an oxygen atom, a sulfur atom or =NH.

Compound (XIX) may be a commercially available product, or can also be produced according to a method known per se or a method analogous thereto. The amount of compound (XIX) to be used is about 0.5 to about 3 mol, preferably about 0.8 to about 2 mol, per 1 mol of compound (XVIII).

This reaction is advantageously carried out without a solvent or in a solvent inert to the reaction. The solvent is not particularly limited as long as the reaction proceeds. Examples thereof include halogenated hydrocarbons, aliphatic hydrocarbon, aromatic hydrocarbons, ethers, amides, alcohols, nitriles, and a mixture of two or more solvents, and the like.

This reaction can also be carried out in the presence of a base, if desired. Examples of the base include basic salts such as sodium carbonate, potassium carbonate, cesium carbonate, sodium hydrogen carbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like. The amount of the base to be used is about 1 to about 30 mol, preferably about 1 to about 10 mol, per 1 mol of compound (XVIII).

While the reaction time varies depending on the reagents and solvent to be used, it is generally about 5 min to about 72 hr, preferably about 0.5 hr to about 30 hr.

The reaction temperature is generally about −5° C. to about 200° C., preferably about 5° C. to about 150° C.

Compound (I) can be produced from compound (VII) in the same manner as in the aforementioned production method, or by condensing compound (XVIII) with a compound represented by the formula (XX)

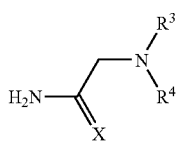

(XX)

wherein each symbol is as defined above.

Compound (XX) may be a commercially available product, or can be produced according to a method known per se or a method analogous thereto.

The amount of compound (XX) to be used is about 0.5 to about 3 mol, preferably about 0.8 to about 2 mol, per 1 mol of compound (XVIII).

This reaction is advantageously carried out without a solvent or in a solvent inert to the reaction. The solvent is not particularly limited as long as the reaction proceeds. Examples thereof include halogenated hydrocarbons, aliphatic hydrocarbon, aromatic hydrocarbons, ethers, amides, alcohols, nitriles, and a mixture of two or more solvents, and the like.

This reaction can also be carried out in the presence of a base, if desired. Examples of the base include basic salts such as sodium carbonate, potassium carbonate, cesium carbonate, sodium hydrogen carbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like. The amount of the base to be used is about 1 to about 30 mol, preferably about 1 to about 10 mol, per 1 mol of compound (XVIII).

While the reaction time varies depending on the reagents and solvent to be used, it is generally about 5 min to about 72 hr, preferably about 0.5 to about 30 hr.

The reaction temperature is generally about −5° C. to about 200° C., preferably about 5° C. to about 150° C.

In each of the aforementioned reactions, when the starting compound has an amino group, a carboxyl group or a hydroxyl group as a substituent, a protecting group generally used in peptide chemistry and the like may be introduced into these groups. By removing the protecting group as necessary after the reaction, the objective compound can be obtained. Introduction or removal of these protective groups may be carried out according to a method known per se, for example, the method disclosed in Theodora W. Greene and Peter G. M. Wuts, "Protective Groups in Organic Synthesis, 3$^{rd}$ Ed.", Wiley-Interscience (1999), or the like.

In all cases, when desired, compound (I) can be produced by performing deprotection, acylation reaction, alkylation reaction, hydrogenation reaction, oxidation reaction, reduction reaction, carbon chain extension reaction and substituent exchange reaction, each singly or in a combination of two or more kinds thereof.

When the object product is obtained in a free form by the above-mentioned reactions, it can be converted to a salt according to a conventional method, and when it is obtained as a salt, it can also be converted to a free form or other salt according to a conventional method. The thus-obtained compound (I) can be isolated and purified from a reaction solution by a known means, for example, phase transfer, concentration, solvent extraction, fractionation, crystallization, recrystallization, chromatography and the like.

When compound (I) is obtained as a free compound, it can be converted to a desired salt by a method known per se or a method analogous thereto; conversely, when compound (I) is obtained as a salt, it can be converted into a free form or another desired salt by a method known per se or a method analogous thereto.

Compound (I) may be used as a prodrug. The prodrug of compound (I) means a compound which is converted to compound (I) under the physiological condition in the body by a reaction with an enzyme, gastric acid, or the like, that is, a compound which is converted to compound (I) by enzymatic oxidation, reduction, hydrolysis, and the like; a compound which is converted to compound (I) by hydrolysis with gastric acid, and the like.

Examples of the prodrug of compound (I) include a compound wherein the amino group of compound (I) is modified with acyl, alkyl or phosphoryl (e.g., a compound wherein the amino group of compound (I) is modified with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl or t-butyl, etc.); a compound wherein the hydroxy group of compound (I) is modified with acyl, alkyl, phosphoric acid or boric acid (e.g., a compound wherein the hydroxy group of compound (I) is modified with acetyl, palmitoyl, propanoyl, pivaloyl, succinyl, fumaryl, alanyl or dimethylaminomethylcarbonyl, etc.); a compound wherein a carboxyl group of compound (I) is modified to ester or amide (e.g., a compound wherein a carboxyl group of compound (I) is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide, etc.); and the like. These compounds can be produced from compound (I) by a method known per se.

In addition, the prodrug of compound (I) may be a compound, which is converted to compound (I) under the physiological conditions, as described in Pharmaceutical Research and Development, Vol. 7 (Molecule Design), pp. 163-198 (1990), published by Hirokawa Publishing Co.

When compound (I) contains an isomer such as an optical isomer, a stereoisomer, a regioisomer or a rotamer, either isomer or a mixture of these are also encompassed in compound (I). For example, when compound (I) has an optical isomer, an optical isomer resolved from a racemate is also encompassed in compound (I). These isomers can be obtained as single products according to synthesis and separation methods known per se (concentration, solvent extraction, column chromatography, recrystallization, etc.)

The compound (I) may be a crystal, and both a single crystal and crystal mixtures are encompassed in compound (I). Crystals can be produced by crystallization according to crystallization methods known per se.

The compound (I) may be a solvate (e.g., hydrate etc.) or a non-solvate, both of which are encompassed in the compound (I).

A compound labeled with an isotope (e.g., $^3$H, $^{14}$C, $^{35}$S, $^{125}$I and the like) and a deuterium conversion form wherein $^1$H has been converted to $^2$H(D) are also encompassed in the compound (I).

Compound (I) and a prodrug thereof of the present invention (hereinafter sometimes to be abbreviated as the compound of the present invention) have a proton pump inhibitory effect and effectively suppress gastric acid secretion. In addition, since they show low toxicity (e.g., acute toxicity, chronic toxicity, genetic toxicity, reproductive toxicity, cardiotoxicity, drug interaction, carcinogenicity and the like) and high water-solubility, and are superior in the stability, in vivo kinetics (absorbability, distribution, metabolism, excretion and the like), and efficacy expression, they are useful as medicaments.

The compound of the present invention is useful for the prophylaxis or treatment of peptic ulcer (e.g., gastric ulcer, duodenal ulcer, anastomotic ulcer, ulcer caused by non-steroidal anti-inflammatory agent, ulcer due to postoperative stress etc.); Zollinger-Ellison syndrome; gastritis; erosive esophagitis; reflux esophagitis such as erosive reflux esophagitis and the like; symptomatic gastroesophageal reflux disease (Symptomatic GERD) such as nonerosive esophageal reflux, esophageal reflux unaccompanied by esophagitis and the like; Barrett's esophagus; functional dyspepsia; gastric cancer (including gastric cancer associated with promoted production of interleukin-1β due to gene polymorphism of interleukin-1); stomach MALT lymphoma; hyperacidity; upper gastrointestinal hemorrhage caused by peptic ulcer, acute stress ulcer, hemorrhagic gastritis, invasive stress (e.g., stress caused by major surgery requiring post-operative intensive management, or cerebrovascular disorder, head trauma, multiple organ failure or extensive burn requiring intensive treatment) and the like; airway disorders; asthma; and the like in mammals (e.g., human, monkey, sheep, bovine, horse, dog, cat, rabbit, rat, mouse etc.), pre-anesthetic administration, eradication or assistant to eradication of *Helicobacter pylori* and the like.

As used herein, the above-mentioned reflux esophagitis and symptomatic gastroesophageal reflux disease (symptomatic GERD) are sometimes collectively referred to simply as GERD.

The content of a compound of the present invention in the pharmaceutical composition of the present invention is about 0.01 to 100% by weight relative to the entire composition. Though subject to change depending on the administration target, administration route, target disease and the like, its dose is about 0.5 to 1,500 mg/day, preferably about 5 to 150 mg/day, based on the active ingredient, when, for example, the compound is orally administered as an anti-ulcer agent to an adult human (60 kg). The compound of the present invention may be administered once daily or in 2 or 3 divided portions per day.

The compound of the present invention shows low toxicity and can be safely administered orally or parenterally (e.g., topical, rectal, intravenous administrations and the like) as it is or as a preparation containing a pharmaceutical composition containing a pharmacologically acceptable carrier admixed according to a method known per se, such as tablets (including sugar-coated tablets and film-coated tablets), powder, granule, capsule (including soft capsule), orally disintegrating tablet, orally disintegrating film, liquid, injection, suppository, sustained-release preparation, plaster and the like. Particularly, the compound of the present invention is preferably administered as an oral preparation in the form of tablet, granule, capsule and the like.

Examples of the pharmacologically acceptable carrier that may be used to produce the pharmaceutical composition of the present invention include various organic or inorganic carrier substances in common use as pharmaceutical materials, including excipients, lubricants, binders, disintegrants, aqueous polymers and basic inorganic salts for solid preparations; and solvents, solubilizing agents, suspending agents, isotonizing agents, buffers and soothing agents for liquid preparations and the like. Other ordinary pharmaceutical additives such as preservatives, anti-oxidants, colorants, sweetening agents, souring agents, bubbling agents and flavorings may also be used as necessary.

Examples of the "excipients" include lactose, sucrose, D-mannitol, starch, cornstarch, crystalline cellulose, light anhydrous silicic acid, titanium oxide and the like.

Examples of the "lubricants" include magnesium stearate, sucrose fatty acid esters, polyethylene glycol, talc, stearic acid and the like.

Examples of the "binders" include hydroxypropyl cellulose, hydroxypropylmethyl cellulose, crystalline cellulose, starch, polyvinylpyrrolidone, gum arabic powder, gelatin, pullulan, low-substituted hydroxypropyl cellulose and the like.

Examples of the "disintegrants" include (1) crosspovidone, (2) what is called super-disintegrants such as crosscarmellose sodium (FMC-Asahi Chemical) and carmellose calcium (Gotoku Yakuhin) etc, (3) sodium carboxymethyl starch (e.g., product of Matsutani Chemical), (4) low-substituted hydroxypropyl cellulose (e.g., product of Shin-Etsu Chemical), (5) corn starch, and so forth. Said "crosspovidone" may be any crosslinked polymer having the chemical name 1-ethenyl-2-pyrrolidinone homopolymer, including polyvinylpyrrolidone (PVPP) and 1-vinyl-2-pyrrolidinone homopolymer, and is exemplified by Colidon CL (produced by BASF), Polyplasdon XL (produced by ISP), Polyplasdon XL-10 (produced by ISP), Polyplasdon INF-10 (produced by ISP) and the like.

Examples of the "aqueous polymers" include ethanol-soluble aqueous polymers [e.g., cellulose derivatives such as hydroxypropyl cellulose (hereinafter also referred to as HPC) etc, polyvinylpyrrolidone and the like], ethanol-insoluble aqueous polymers [e.g., cellulose derivatives such as hydroxypropylmethyl cellulose (hereinafter also referred to as HPMC) and the like, methyl cellulose, carboxymethyl cellulose sodium and the like, sodium polyacrylate, polyvinyl alcohol, sodium alginate, guar gum and the like] and the like.

Examples of the "basic inorganic salts" include basic inorganic salts of sodium, potassium, magnesium and/or calcium. Preferred are basic inorganic salts of magnesium and/or calcium. More preferred are basic inorganic salts of magnesium. Examples of the basic inorganic salts of sodium include sodium carbonate, sodium hydrogen carbonate, disodium hydrogenphosphate and the like. Examples of the basic inorganic salts of potassium include potassium carbonate, potassium hydrogencarbonate and the like. Examples of the basic inorganic salts of magnesium include heavy magnesium carbonate, magnesium carbonate, magnesium oxide, magnesium hydroxide, magnesium aluminometasilicate, magnesium silicate, magnesium aluminate, synthetic hydrotalcite [$Mg_6Al_2(OH)_{16} \cdot CO_3 \cdot 4H_2O$], and aluminum magnesium hydroxide. Preferred are heavy magnesium carbonate, magnesium carbonate, magnesium oxide, magnesium hydroxide and the like. Examples of the basic inorganic salts of calcium include precipitated calcium carbonate, calcium hydroxide and the like.

Examples of the "solvents" include water for injection, alcohol, propylene glycol, macrogol, sesame oil, corn oil, olive oil and the like.

Examples of the "solubilizing agents" include polyethylene glycol, propylene glycol, D-mannitol, benzyl benzoate, ethanol, trisaminomethane, cholesterol, triethanolamine, sodium carbonate, sodium citrate and the like.

Examples of the "suspending agents" include surfactants such as stearyltriethanolamine, sodium lauryl sulfate, laurylaminopropionic acid, lecithin, benzalkonium chloride, benzethonium chloride, glyceryl monostearate etc; hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose and the like, and the like.

Examples of the "isotonizing agents" include glucose, D-sorbitol, sodium chloride, glycerol, D-mannitol and the like.

Examples of the "buffers" include buffer solutions of phosphates, acetates, carbonates, citrates and the like, and the like.

Examples of the "soothing agents" include benzyl alcohol and the like.

Examples of the "preservatives" include p-oxybenzoic acid esters, chlorobutanol, benzyl alcohol, phenethyl alcohol, dehydroacetic acid, sorbic acid and the like.

Examples of the "antioxidants" include sulfites, ascorbic acid, α-tocopherol and the like.

Examples of the "colorants" include food colors such as Food Color Yellow No. 5, Food Color Red No. 2, Food Color Blue No. 2 and the like; food lake colors, red ferric oxide and the like.

Examples of the "sweetening agents" include saccharin sodium, dipotassium glycyrrhizinate, aspartame, stevia, thaumatin and the like.

Examples of the "souring agents" include citric acid (citric anhydride), tartaric acid, malic acid and the like.

Examples of the "bubbling agents" include sodium bicarbonate and the like.

The "flavorings" may be synthetic substances or naturally occurring substances, and examples thereof include flavorings of lemon, lime, orange, menthol, strawberry and the like.

The compound of the present invention may be prepared as a preparation for oral administration in accordance with a commonly-known method, by, for example, compression-shaping with a carrier such as an excipient, a disintegrant, a binder, a lubricant, or the like, and subsequently coating the preparation as necessary by a commonly known method for the purpose of taste masking, enteric dissolution or sustained release. For an enteric preparation, an intermediate layer may be provided by a commonly known method between the enteric layer and the drug-containing layer for the purpose of separation of the two layers.

For preparing the compound of the present invention as an orally disintegrating tablet, available methods include a method in which a core containing crystalline cellulose and lactose is coated with the compound of the present invention and, where necessary, a basic inorganic salt, and then further coated with a coating layer containing an aqueous polymer to give a composition, which is coated with an enteric coating layer containing polyethylene glycol, further coated with an enteric coating layer containing triethyl citrate, still further coated with an enteric coating layer containing polyethylene glycol, and finally coated with mannitol to give fine granules, which are mixed with additives and shaped.

Examples of the above-mentioned "enteric coating layer" include a layer consisting of a mixture of one or more kinds from aqueous enteric polymer substrates such as cellulose acetate phthalate (CAP), hydroxypropylmethyl cellulose phthalate, hydroxymethyl cellulose acetate succinate, methacrylic acid copolymers (e.g., Eudragit L30D-55 (trade name; produced by Rohm), Colicoat MAE30DP (trade name; produced by BASF), Polyquid PA30 (trade name; produced by San-yo Chemical) etc.), carboxymethylethyl cellulose, shellac and the like; sustained-release substrates such as methacrylic acid copolymers (e.g., Eudragit NE30D (trade name), Eudragit RL30D (trade name), Eudragit RS30D (trade name), etc.) and the like; aqueous polymers; plasticizers such as triethyl citrate, polyethylene glycol, acetylated monoglycerides, triacetin, castor oil and the like; and the like, and the like.

Examples of the above-mentioned "additive" include aqueous sugar alcohols (e.g., sorbitol, mannitol, maltitol, reduced starch saccharides, xylitol, reduced palatinose, erythritol, etc.), crystalline cellulose (e.g., Ceolas KG 801, Avicel PH 101, Avicel PH 102, Avicel PH 301, Avicel PH 302, Avicel RC-591 (crystalline cellulose-carmellose sodium) etc.), low-substituted hydroxypropyl cellulose (e.g., LH-22, LH-32, LH-23, LH-33 (Shin-Etsu Chemical), mixtures thereof etc.) and the like. Furthermore, binders, souring agents, bubbling agents, sweetening agents, flavorings, lubricants, colorants, stabilizers, excipients, disintegrants and the like are also used.

The compound of the present invention may be used in combination with 1 to 3 other active ingredients.

Examples of the "other active ingredients" include anti-*Helicobacter pylori* active substances, imidazole compounds, bismuth salts, quinolone compounds, and so forth.

Examples of the "anti-*Helicobacter pylori* active substance" include penicillin antibiotic (e.g., amoxicillin, benzylpenicillin, piperacillin, mecillinam, ampicillin, temocillin, bacampicillin, aspoxicillin, sultamicillin, lenampicillin etc.), cephem antibiotic (e.g., cefixime, cefaclor etc.), macrolide antibiotic (e.g., erythromycin, clarithromycin, roxithromycin, rokitamycin, flurithromycin, telithromycin etc.), tetracycline antibiotic (e.g., tetracycline, minocycline etc.), aminoglycoside antibiotic (e.g., gentamicin, amikacin, streptomycin etc.), imipenem and the like. Of these, penicillin antibiotic, macrolide antibiotic and the like are preferable.

Examples of the "imidazole compounds" include metronidazole, miconazole and the like.

Examples of the "bismuth salts" include bismuth acetate, bismuth citrate, bismuth subsalicylate and the like.

Examples of the "quinolone compounds" include ofloxacin, ciploxacin and the like.

For eradication of *Helicobacter pylori*, a compound (I) or a salt thereof of the present invention with antibiotic penicillin (e.g., amoxicillin and the like) and antibiotic macrolide (e.g., clarithromycin and the like) is preferably used.

For the purpose of eradication of *Helicobacter pylori*, while the compound of the present invention has an anti-*H. pylori* action (bacteriostatic action or eradication action) by itself, it can enhance antibacterial action of other antibiotics based on the pH controlling action in the stomach and the like, and also provides an assistant effect such as an eradication effect based on the action of the antibiotics to be used in combination.

The "other active ingredients" and the compound (I) or a salt thereof of the present invention may be mixed, prepared as a single pharmaceutical composition [e.g., tablets, powders, granules, capsules (including soft capsules), liquids, injectable preparations, suppositories, sustained-release preparations, etc.], in accordance with a commonly known method, and used in combination, and may also be prepared as separate preparations and administered to the same subject simultaneously or at a time interval.

In addition, the compound of the present invention may be used in combination with a gastric motility enhancer, a drug acting on lower esophageal sphincter (e.g., temporary lower esophageal sphincter relaxation suppressant etc.), ClC-2 channel opener (intestinal juice secretion enhancer), a histamine $H_2$ receptor antagonist, an antacid, a sedative, a stomachic digestant or a non-steroidal anti-inflammatory drug (NSAID).

Examples of the "gastric motility enhancer" include domperidone, metoclopramide, mosapride, itopride, tegaserod and the like.

Examples of the "a drug acting on lower esophageal sphincter" include GABA-B receptor agonists such as baclofen, an optically active form thereof and the like, glutamine receptor antagonists and the like.

Examples of the "ClC-2 channel opener (intestinal juice secretion enhancer)" include lubiprostone and the like.

Examples of the "histamine $H_2$ receptor antagonist" include cimetidine, ranitidine, famotidine, roxatidine, nizatidine, lafutidine and the like.

Examples of the "antacid" include sodium hydrogen carbonate, aluminum hydroxide and the like.

Examples of the "sedatives" include diazepam, chlordiazepoxide and the like.

Examples of the "stomachic digestant" include gentiana, swertia japonica, diastase and the like.

Examples of the "non-steroidal anti-inflammatory drug" include aspirin, indomethacin, ibuprofen, mefenamic acid, diclofenac, etodorac, piroxicam, celecoxib and the like.

A gastric motility enhancer, a drug acting on lower esophageal sphincter, a ClC-2 channel opener (intestinal juice secretion enhancer), a histamine $H_2$ receptor antagonist, an antacid, a sedative, a stomachic digestant or a non-steroidal anti-inflammatory drug and compound (I) or a salt thereof of the present invention may be mixed, prepared as a single pharmaceutical composition [e.g., tablets, powders, granules, capsules (including soft capsules), liquids, injections, suppositories, sustained-release preparations, etc.] according to a method known per se for combined use, or may also be prepared as separate preparations and administered to the same subject simultaneously or in a staggered manner.

The compound of the present invention may be used in combination with the following drugs.

(i) proton pump inhibitor, for example, omeprazole, esomeprazole, pantoprazole, rabeprazole, tenatoprazole, ilaprazole and lansoprazole;

(ii) oral antacid combination agent, for example, Maalox, Aludrox and Gaviscon;

(iii) mucous membrane protector, for example, polaprezinc, ecabe sodium, rebamipide, teprenone, cetraxate, sucralfate, chloropylline-copper and plaunotol;

(iv) antigastric agent, for example, anti-gastrin vaccine, itriglumide and Z-360;

(v) 5-$HT_3$ antagonist, for example, dolasetron, palonosetron, alosetron, azasetron, ramosetron, mitrazapine, granisetron, tropisetron, E-3620, ondansetron and indisetron;

(vi) 5-$HT_4$ agonist, for example, tegaserod, mosapride, cinitapride and oxtriptane;

(vii) laxative agent, for example, Trifyba, Fybogel, Konsyl, Isogel, Regulan, Celevac and Normacol;

(viii) $GABA_B$ agonist, for example, baclofen and AZD-3355;

(ix) $GABA_B$ antagonist, for example, GAS-360 and SGS-742;

(x) calcium channel blocker, for example, aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;

(xi) dopamine antagonist, for example, metoclopramide, domperidone and levosulpiride;

(xii) tachykinin (NK) antagonist, particularly, NK-3, NK-2 and NK-1 antagonist, for example, nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4] diazocino[2,1-g][1,7]naphthyridine-6-13-dione (TAK-637), 5-[[(2R,3S)-2-[(1R)-1-[3,5-bis(trifluoromethyl)phenyl] ethoxy-3-(4-fluorophenyl)-4-morpholinyl]methyl]-1,2-dihydro-3H-1,2,4-triazol-3-one (MK-869), lanepitant, dapitant and (2S,3S)-3-[[2-methoxy-5-(trifluoromethoxy)phenyl] methylamino]-2-phenyl-piperidine;

(xiii) nitric monoxide synthase inhibitor, for example, GW-274150, tilarginine, P54, guanidioethyldisulfide and nitroflurbiprofen;

(xiv) vanilloid receptor 1 antagonist, for example, AMG-517 and GW-705498;

(xv) ghrelin agonist, for example, capromorelin and TZP-101;

(xvi) AchE release stimulant, for example, Z-338 and KW-5092.

The above-mentioned drugs (i)-(xvi) and compound (I) or a salt thereof of the present invention may be mixed, prepared as a single pharmaceutical composition [e.g., tablets, powders, granules, capsules (including soft capsules), liquids, injections, suppositories, sustained-release preparations, etc.] according to a method known per se for combined use, or may also be prepared as separate preparations and administered to the same subject simultaneously or in a staggered manner.

EXAMPLES

The present invention is explained in detail in the following by referring to Reference Examples, Examples and Experimental Examples, which are not to be construed as limitative.

In the following Reference Examples and Examples, the "room temperature" generally means about 10° C. to about 35° C., but it is not particularly strictly limited. The mixing ratio 5 of liquids shows a volume ratio. Unless otherwise specified, "%" means weight %. The yield is in mol/mol %. Silica gel column chromatography was performed using silica gel 60 (0.063-0.200 mm) manufactured by MERCK, Fuji Silysia Chemical Ltd. Chromatorex (trade name) NH (described as basic silica gel column chromatography) or Purif-Pack manufactured by MORITEX (described as silica gel column chromatography or basic silica gel column chromatography). The melting point was measured using Yanagimoto trace melting point measurement apparatus or Buechi trace melting point measurement apparatus (B-545), and shown without amendment. For $^1$H-NMR spectrum, tetramethylsilane was used as the internal standard, and Varian Gemini-200 (200 MHz), Mercury-300 (300 MHz) spectrometer, Bruker AVANCE AV300 (300 MHz) and JNM-AL400 (400 MHz) nuclear magnetic resonance apparatuses JEOL DATUM (JEOL DATUM LTD.) were used for the measurement. The following abbreviations are used for showing the measurement results. s: singlet, d: doublet, dd: double doublet, ddd: triple doublet, dt: double triplet, t: triplet, q: quartet, dq: double quartet, m: multiplet, br: broad, brs: broad singlet, J: coupling constant, Hz: Hertz.

Reference Example 1 ethyl 1-(4-nitrophenyl)-2-[(4-nitrophenyl)thio]-1H-imidazole-4-carboxylate

Ethyl 2-mercapto-1H-imidazole-4-carboxylate (1.00 g), 1-fluoro-4-nitrobenzene (2.05 g) and anhydrous potassium carbonate (4.00 g) were mixed with N,N-dimethylformamide (30 mL), and the mixture was stirred at 100° C. for 4 hr. After cooling, water was added, and the mixture was extracted with ethyl acetate. The extract was washed with saturated brine, dried over anhydrous magnesium sulfate, and concentrated under reduced pressure. Diisopropyl ether was added to the residue, and crystals were collected by filtration to give the title compound as pale-yellow crystals (yield 2.06 g, yield 86%).

$^1$H-NMR(CDCl$_3$)δ:1.43(3H,t,J=7.2 Hz), 4.46(2H,q,J=7.2 Hz), 7.21-7.26(2H,m), 7.46-7.51(2H,m), 8.01(1H,$), 8.07-8.11(2H,m), 8.31-8.36(2H,m).

Reference Example 2 ethyl 1-(4-aminophenyl)-2-[(4-aminophenyl)thio]-1H-imidazole-4-carboxylate

Ethyl 1-(4-nitrophenyl)-2-[(4-nitrophenyl)thio]-1H-imidazole-4-carboxylate (3.00 g) was suspended in ethanol (120 mL), iron powder (4.05 g), anhydrous calcium chloride (0.81 g) and water (20 mL) were added and the mixture was heated under reflux for 4 hr. The reaction mixture was allowed to cool and filtered, saturated aqueous sodium hydrogen carbonate solution was added to the obtained filtrate, and the mixture was extracted with ethyl acetate. The extract was washed with saturated brine, dried over anhydrous magnesium sulfate, and concentrated under reduced pressure. Methanol (30 mL) was added to the residue, and crystals were collected by filtration to give the title compound as pale-yellow crystals (yield 2.00 g, yield 78%).

$^1$H-NMR(DMSO-d$_6$)δ:1.25(3H,t,J=7.1 Hz), 4.21(2H,q, J=7.1 Hz), 5.40(2H,s), 5.49(2H,s), 6.46-6.51(2H,m), 6.59-6.64(2H,m), 6.93-6.97(2H,m), 6.99-7.04(2H,m), 7.95(1H,s).

Reference Example 3 ethyl 1-phenyl-2-(phenylthio)-1H-imidazole-4-carboxylate

Ethyl 1-(4-aminophenyl)-2-[(4-aminophenyl)thio]-1H-imidazole-4-carboxylate (1.90 g) was dissolved in concentrated hydrochloric acid (30 mL), and a solution of sodium nitrite (1.00 g) in water (5 mL) was added dropwise at 5-10° C. The mixture was stirred at the same temperature for 1 hr, and the obtained reaction mixture was added dropwise to 50% hypophosphorous acid solution (30 mL) by small portions. The mixture was stirred at room temperature for 3 hr, and extracted with ethyl acetate. The extract was washed with saturated aqueous sodium hydrogen carbonate solution, water and saturated brine in this order, dried over anhydrous magnesium sulfate, and concentrated under reduced pressure to give the title compound as a yellow oil (yield 1.17 g, yield 67%).

$^1$H-NMR(CDCl$_3$)δ:1.40(3H,t,J=7.1 Hz), 4.41(2H,q,J=7.1 Hz), 7.08-7.17(7H,m), 7.35-7.43(3H,m), 7.85(1H,s).

Reference Example 4

[1-phenyl-2-(phenylthio)-1H-imidazol-4-yl]methanol

A solution (30 mL) of ethyl 1-phenyl-2-(phenylthio)-1H-imidazole-4-carboxylate (1.17 g) in tetrahydrofuran was cooled to −70° C., a 1.5 mol/L solution (12 mL) of diisobutylaluminum hydride in toluene was added dropwise by small portions. The reaction mixture was stirred at 0° C. for 4 hr, water was added and the mixture was stirred for 30 min. Tetrahydrofuran was added to the obtained gel and the mixture was filtered. The filtrate was concentrated under reduced pressure. A mixed solution of ethyl acetate-diisopropyl ether (1:1) was added to the residue, and insoluble crystals were collected by filtration to give the title compound as pale-yellow crystals (yield 797 mg, yield 78%).

$^1$H-NMR(CDCl$_3$)δ:2.59(1H,br), 4.69(2H,$), 7.08-7.24 (8H,m), 7.37-7.41(3H,m).

Reference Example 5

1-phenyl-2-(phenylthio)-1H-imidazole-4-carbaldehyde

To a solution of 1-phenyl-2-(phenylthio)-1H-imidazol-4-yl]methanol (740 mg) in acetonitrile (50 mL) were added tetrapropylammonium perruthenate (185 mg), N-methylmorpholine N-oxide (1.42 g) and molecular sieves 4A powder (5 g) and the mixture was stirred at room temperature for 2 hr. The reaction mixture was filtered through celite, and the filtrate was concentrated under reduced pressure. The residue was purified by silica gel column chromatography (eluent: hexane-ethyl acetate=3:2) to give the title compound as a pale-yellow oil (yield 400 mg, yield 54%).

$^1$H-NMR(CDCl$_3$)δ:7.18-7.25(7H,m), 7.41-7.49(3H,m), 7.85(1H,s), 9.96(1H,s).

Reference Example 6 methyl (4-formyl-2-phenyl-1H-imidazol-1-yl)(phenyl)acetate

To a solution of 2-phenyl-1H-imidazole-4-carbaldehyde (1.73 g) in N,N-dimethylformamide (35 mL) were added potassium carbonate (2.78 g) and methyl bromo(phenyl)acetate (2.53) and the mixture was stirred at 85° C. for 3 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=1:1→3:7) and crystallized from diisopropyl ether to give the title compound as colorless crystals (yield 814 mg, yield 25%).

$^1$H-NMR(CDCl$_3$)δ:3.80(3H,s), 6.10(1H,s), 7.21-7.26(2H, m), 7.42-7.44(3H,m), 7.53(5H,s), 7.84(1H,s), 9.91(1H,s).

Reference Example 7

2-phenyl-1-pyrimidin-2-yl-1H-imidazole-4-carbaldehyde

To a solution of 2-phenyl-1H-imidazole-4-carbaldehyde (700 mg) in dimethylformamide (30 mL) was added sodium hydride (60% in oil, 180 mg) at room temperature and the mixture was stirred for 30 min. 2-Chloropyrimidine (489 mg) was further added and the mixture was stirred for 15 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→2:3) to give the title compound as a yellow oil (yield 160 mg, yield 16%).

$^1$H-NMR(CDCl$_3$)δ:7.30-7.49(6H,m), 8.45(1H,s), 8.69 (2H,d,J=4.9 Hz), 10.03(1H,s).

Reference Example 8

N-methyl-1-(2-phenyl-1H-imidazol-4-yl)methanamine dihydrochloride

To a solution of 2-phenyl-1H-imidazole-4-carbaldehyde (1.73 g) in ethanol (30 mL) was added 40% methylamine-methanol solution (2.36 g) and the mixture was stirred at 65° C. for 1 hr. The mixture was allowed to cool to room temperature, sodium borohydride (571 mg) was added and the mixture was stirred for 30 min. 1 mol/L Hydrochloric acid was added to the reaction mixture, and the mixture was concentrated under reduced pressure. A saturated aqueous sodium hydrogen carbonate solution was added to the residue, and the mixture was extracted with tetrahydrofuran. The extract was dried over anhydrous magnesium sulfate, and concentrated under reduced pressure. The residue was purified by basic silica gel column chromatography (eluent: ethyl acetate-methanol=1:0→4:1) and dissolved in methanol (10 mL). A 4 mol/L hydrogen chloride-ethyl acetate solution (5 mL) was added, and the mixture was concentrated under reduced pressure. The residue was crystallized from ethyl acetate to give the title compound as colorless crystals (yield 1.06 g, yield 41%).

$^1$H-NMR(DMSO-$d_6$)δ:2. 62 (3H, s), 4.33(2H,s), 7.55-7.73 (3H,m), 7.83(1H,s), 8.21(2H,br), 9.64(2H,br), 2H not detected.

Reference Example 9 tert-butyl methyl[(2-phenyl-1H-imidazol-4-yl)methyl]carbamate

To a solution of N-methyl-1-(2-phenyl-1H-imidazol-4-yl)methanamine dihydrochloride (430 mg) and triethylamine (502 mg) in acetonitrile (10 mL) was added di-tert-butyl bicarbonate (541 mg) and the mixture was stirred at 45° C. for 1 hr. A 1 mol/L aqueous sodium hydroxide solution (20 mL) was added and the mixture was further stirred for 30 min. Water was added to the reaction mixture, and the mixture was extracted with ethyl acetate. The extract was washed with water and saturated brine, dried over anhydrous magnesium sulfate, and concentrated under reduced pressure. The residue was purified by silica gel column chromatography (eluent: hexane-ethyl acetate=4:1→1:4) to give the title compound as a colorless oil (yield 350 mg, yield 74%).

$^1$H-NMR(DMSO-$d_6$)δ:1.49(9H,s), 2.69-3.08(3H,m), 4.19⁻4.58(2H,m), 7.02(1H,br), 7.29-7.51(3H,m), 7.73-7.86 (2H,m), 1H not detected.

Reference Example 10

4-bromo-5-[(3-methoxyphenyl)thio]thiophene-2-carbaldehyde

To a solution of 4,5-dibromothiophene-2-carbaldehyde (1.0 g) in N,N-dimethylformamide (10 mL) were added potassium carbonate (665 mg) and 3-methoxybenzenethiol (571 mg) at room temperature. After stirring at room temperature overnight, water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=19:1→7:1) to give the title compound as a pale-yellow crude oil (yield 1.30 g).

$^1$H-NMR(CDCl$_3$)δ:3.81(3H,s), 6.92-6.96(1H,m), 7.06-7.10(2H,m), 7.28-7.34(1H,m), 7.61(1H,s), 9.68(1H,s).

Reference Example 11 tert-butyl ({4-bromo-5-[(3-methoxyphenyl)thio]-2-thienyl}methyl)methylcarbamate

Crude 4-bromo-5-[(3-methoxyphenyl)thio]thiophene-2-carbaldehyde (1.3 g) was dissolved in tetrahydrofuran (5 mL) and methanol (5 mL), and 40% methylamine-methanol solution (3.8 mL) was added. After stirring at room temperature for 3 hr, sodium borohydride (840 mg) was further added and the mixture was stirred for 3 hr. The solvent was evaporated under reduced pressure, water was added to the residue and the mixture was extracted with ethyl acetate. The extract was washed with saturated brine, dried over anhydrous sodium sulfate, and concentrated under reduced pressure. The residue was dissolved in tetrahydrofuran (10 mL), and di-tert-butyl bicarbonate (888 mg) was added at room temperature. After stirring for 10 min, the reaction mixture was concentrated under reduced pressure. The residue was purified by silica gel column chromatography (eluent: hexane-ethyl acetate=19:1→6:1) to give the title compound as a colorless oil (yield 1.28 g, yield of two steps 78%).

$^1$H-NMR(CDCl$_3$)δ:1.47(9H,s), 2.87(3H,brs), 3.75(3H,s), 4.45(2H,br), 6.71-6.79(3H,m), 6.91(1H,brs), 7.13(1H,t, J=7.8 Hz).

Reference Example 12 tert-butyl ({4-(2-fluorophenyl)-5-[(3-methoxyphenyl)thio]-2-thienyl}methyl)methylcarbamate tert-Butyl ({4-bromo-5-[(3-methoxyphenyl)thio]-2-thienyl}methyl)methylcarbamate (596 mg), (2-fluorophenyl)boronic acid (225 mg), sodium carbonate (341 mg) and tetrakis(triphenylphosphine)palladium (0) (155 mg) were suspended in a mixture of 1,2-dimethoxyethane (10 mL) and water (4 mL), and the suspension was stirred at 105° C. for 4 hr under a nitrogen atmosphere. The reaction mixture was allowed to cool to room temperature, water was added, and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=19:1→9:1) to give the title compound as a colorless oil (yield 459 mg, yield 75%).

$^1$H-NMR(CDCl$_3$)δ:1.48(9H,s), 2.91(3H,brs), 3.71(3H,s), 4.52(2H,br), 6.63-6.72(3H,m), 7.04-7.15(4H,m), 7.25-7.39 (2H,m).

Reference Example 13 tert-butyl ({4-(2-fluorophenyl)-5-[(3-methoxyphenyl)sulfinyl]-2-thienyl}methyl)methylcarbamate To a solution of tert-butyl ({4-(2-fluorophenyl)-5-[(3-methoxyphenyl)thio]-2-thienyl}methyl)methylcarbamate (277 mg) in ethyl acetate (5 mL) was added 3-chloroperbenzoic acid (144 mg) and the mixture was stirred for 6 hr. The reaction mixture was treated with aqueous sodium thiosulfate solution, and extracted with ethyl acetate. The extract was washed with water, saturated aqueous sodium hydrogen carbonate solution and saturated brine, dried over anhydrous sodium sulfate, and concentrated under reduced pressure. The residue was purified by silica gel column chromatography (eluent: hexane-ethyl acetate=9:1→4:1) to give the title compound as a colorless oil (yield 231 mg, yield 81%).

$^1$H-NMR(CDCl$_3$)δ:1.42(9H,s), 2.85(3H,s), 3.84(3H,s), 4.45(2H,brs), 6.92-7.00(2H,m), 7.12-7.44(6H,m), 7.54-7.59 (1H,m).

Reference Example 14

5-phenoxy-4-phenylthiophene-2-carbaldehyde

To a solution of 5-bromo-4-phenylthiophene-2-carbaldehyde (652 mg) in N,N-dimethylformamide (10 mL) was added sodium phenolate (425 mg) at room temperature. After stirring at room temperature overnight, water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=99:1→9:1) to give the title compound as a pale-yellow solid (yield 152 mg, yield 22%).
$^1$H-NMR(CDCl$_3$)δ:7.18-7.45(8H,m), 7.67-7.70(2H,m), 7.84(1H,s), 9.76(1H,s).

Reference Example 15 tert-butyl methyl[(4-phenyl-2-thienyl)methyl]carbamate

4-Phenylthiophene-2-carbaldehyde (3.0 g) was dissolved in tetrahydrofuran (5 mL) and methanol (5 mL), and 40% methylamine-methanol solution (16.5 mL) was added. After stirring at room temperature for 3 hr, excess methylamine was evaporated under reduced pressure. The residue was diluted with methanol (5 mL), sodium borohydride (3.6 g) was added and the mixture was further stirred for 3 hr. The solvent was evaporated under reduced pressure, water was added to the residue and the mixture was extracted with ethyl acetate. The extract was washed with saturated brine, dried over anhydrous sodium sulfate, and concentrated under reduced pressure. The residue was dissolved in tetrahydrofuran (20 mL), and di-tert-butyl bicarbonate (3.8 g) was added at room temperature. After stirring for 10 min, the reaction mixture was concentrated under reduced pressure. The residue was purified by silica gel column chromatography (eluent: hexane-ethyl acetate=19:1→9:1) to give the title compound in a crude form as a colorless oil (yield 4.77 g).
$^1$H-NMR(CDCl$_3$)δ:1.53(9H,s), 2.89(3H,brs), 4.55(2H,brs), 7.20(1H,brs), 7.26-7.40(4H,m), 7.53-7.57(2H, m).

Reference Example 16 tert-butyl [(5-bromo-4-phenyl-2-thienyl)methyl]methylcarbamate

To a solution of tert-butyl methyl[(4-phenyl-2-thienyl)methyl]carbamate (4.77 g) in N,N-dimethylformamide (30 mL) was added N-bromosuccinimide (2.83 g) at room temperature and the mixture was stirred for 4 hr. Water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=99:1→19:1) to give the title compound as a pale-yellow oil (yield 4.1 g, yield of 2 steps 67%).
$^1$H-NMR(CDCl$_3$)δ:1.51(9H,s), 2.89(3H,s), 4.47(2H,s), 6.86(1H,s), 7.34-7.44(3H,m), 7.50-7.54(2H,m).

Reference Example 17 tert-butyl ({5-[hydroxy(phenyl)methyl]-4-phenyl-2-thienyl}methyl)methylcarbamate A solution of tert-butyl [(5-bromo-4-phenyl-2-thienyl)methyl]methylcarbamate (1.0 g) in tetrahydrofuran was cooled to −78° C., and 1.6 mol/L n-butyllithium-hexane solution (1.96 mL) was added dropwise. After stirring at the same temperature for 1 hr, benzaldehyde (334 mg) in tetrahydrofuran (3 mL) was added dropwise. The mixture was gradually warmed to room temperature, and stirred for 2 hr. The reaction mixture was treated with saturated aqueous ammonium chloride solution, and extracted with ethyl acetate. The extract was washed with saturated brine, dried over anhydrous sodium sulfate, and concentrated under reduced pressure. The residue was purified by silica gel column chromatography (eluent: hexane-ethyl acetate=19:1→9:1) to give the title compound as a pale-yellow oil (yield 607 mg, yield 57%).
$^1$H-NMR(CDCl$_3$)δ:1.47(9H,s), 2.36(1H,brt), 2.87(3H,s), 4.46(2H,brs), 6.09(1H,d,J=3.3 Hz), 6.86(1H,brs), 7.25-7.41 (10H,m).

Reference Example 18 tert-butyl [(5-benzoyl-4-phenyl-2-thienyl)methyl]methylcarbamate

To a solution of tert-butyl ({5-[hydroxy(phenyl)methyl]-4-phenyl-2-thienyl}methyl)methylcarbamate (385 mg) in toluene (5 mL) was added manganese dioxide (1.1 g) and the mixture was stirred at 120° C. for 8 hr. The reaction mixture was cooled to room temperature, filtered through celite, and washed with ethyl acetate. The filtrate was concentrated under reduced pressure, and the residue was purified by silica gel column chromatography (eluent: hexane-ethyl acetate=9:1→4:1) to give the title compound as a pale-yellow oil (yield 236 mg, yield 62%).
$^1$H-NMR(CDCl$_3$)δ:1.51(9H,s), 2.95(3H,brs), 4.59(2H,br), 7.04(1H,brs), 7.11-7.21(7H,m), 7.28-7.33(1H, m), 7.57-7.61(2H,m).

Reference Example 19

2-bromo-1-(2-fluorophenyl)ethanone

To a solution of 1-(2-fluorophenyl)ethanone (15.1 g) in acetic acid (150 mL) was added bromine (5.8 mL). The mixture was stirred at room temperature for 2 hr, and concentrated under reduced pressure. A saturated aqueous sodium hydrogen carbonate solution was added to the residue, and the mixture was extracted with ethyl acetate. The extract was washed with saturated aqueous sodium hydrogen carbonate solution, water and saturated brine, dried over anhydrous magnesium sulfate, and concentrated under reduced pressure to give the title compound as a pale-yellow oil (yield 22.9 g, yield 97%).
$^1$H-NMR(CDCl$_3$)δ:4.53(2H,d,J=2.4 Hz), 7.13-7.20(1H, m), 7.27-7.30(1H,m), 7.54-7.61(1H,m), 7.91-7.96(1H,m).

Reference Example 20

1-phenyl-2-(phenylthio)ethanone

To a suspension of 2-bromoacetophenone (10 g) and potassium carbonate (7.1 g) in ethanol (150 mL) was added thiophenol (5.2 mL) under ice-cooling, and the mixture was stirred at room temperature for 12 hr. Insoluble material was filtered off, and the filtrate was concentrated under reduced pressure. Water was added to the residue, and the mixture was extracted with ethyl acetate. The extract was washed with saturated aqueous sodium hydrogen carbonate solution, water and saturated brine in this order, dried over anhydrous magnesium sulfate, and concentrated under reduced pressure. The residue was purified by silica gel column chromatography (eluent: hexane-ethyl acetate=15:1) to give the title compound as yellow crystals (yield 11 g, yield 98%).

$^1$H-NMR(CDCl$_3$)δ:4.28(2H,s), 7.20-7.32(3H,m), 7.37-7.41(1H,m), 7.44-7.50(4H,m), 7.56-7.62(1H,m), 7.93-7.97(1H,m).

Reference Example 21

1-(2-fluorophenyl)-2-(phenylthio)ethanone

To a suspension of 2-bromo-1-(2-fluorophenyl)ethanone (3.0 g) and potassium carbonate (2.0 g) in ethanol (30 mL) was added dropwise thiophenol (1.4 mL) at 0° C. The mixture was stirred at room temperature for 8 hr, insoluble materials were filtered off, and the filtrate was concentrated under reduced pressure. Water was added to the residue, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by silica gel column chromatography (eluent: hexane-ethyl acetate=15:1) to give the title compound as a pale-yellow solid (yield 2.2 g, yield 64%).

$^1$H-NMR(CDCl$_3$)δ:4.26(2H,d,J=2.1 Hz), 7.10-7.35(7H, m), 7.50-7.57(1H,m), 7.79-7.85(1H,m).

Reference Example 22

2-bromo-1-phenyl-2-(phenylthio)ethanone

To a solution of 1-phenyl-2-(phenylthio)ethanone (2.1 g) in acetic acid (20 mL) was added bromine (0.5 mL) and the mixture was stirred at room temperature for 1 hr. The reaction mixture was concentrated under reduced pressure, water was added to the residue, and the mixture was extracted with ethyl acetate. The extract was washed with saturated aqueous sodium hydrogen carbonate solution, water and saturated brine, dried over anhydrous magnesium sulfate, and concentrated under reduced pressure to give the title compound as a yellow oil (yield 2.9 g, yield about 100%).

$^1$H-NMR(CDCl$_3$)δ:6.48(1H,s), 7.40-7.44(5H,m), 7.48-7.53(3H,m), 8.04-8.07(2H,m).

Reference Example 23

2-bromo-1-(2-fluorophenyl)-2-(phenylthio)ethanone

To a solution of 1-(2-fluorophenyl)-2-(phenylthio)ethanone (413 mg) in ethyl acetate (6 mL) were added copper (II) bromide (419 mg) and a 47% solution (2 drops) of hydrogen bromide in acetic acid and the mixture was stirred at 80° C. for 2 hr. The reaction mixture was cooled to room temperature, and concentrated under reduced pressure. A saturated aqueous sodium hydrogen carbonate solution was added to the residue, and the mixture was extracted with ethyl acetate. The extract was washed with saturated aqueous sodium hydrogen carbonate solution, water and saturated brine, dried over anhydrous magnesium sulfate, and concentrated under reduced pressure to give the title compound as a brown oil (yield 503 mg, yield 92%).

$^1$H-NMR(CDCl$_3$)δ:6.61(1H,d,J=3.0 Hz), 7.08-7.63(8H, m), 7.88-7.96(1H,m).

Reference Example 24

(1,3-dioxo-1,3-dihydro-2H-isoindol-2-yl)acetonitrile

To a solution of bromoacetonitrile (22 g) in N,N-dimethylformamide (200 mL) was added potassium phthalimide (34 g) under ice-cooling and the mixture was stirred at room temperature for 3 hr. Water was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was recrystallized from ethanol to give the title compound as white crystals (yield 27 g, yield 80%).

$^1$H-NMR(CDCl$_3$)δ:4.59(2H,s), 7.79-7.85(2H,m), 7.90-7.97(2H,m).

Reference Example 25

2-(1,3-dioxo-1,3-dihydro-2H-isoindol-2-yl)ethanethioamide

To a mixture of (1,3-dioxo-1,3-dihydro-2H-isoindol-2-yl) acetonitrile (15 g), a 4 mol/L hydrogen chloride-ethyl acetate solution (40 mL) and tetrahydrofuran (50 mL) was added O,O-diethyl dithiophosphate (15 mL) and the mixture was stirred at room temperature for 5 hr. Water was added to the reaction mixture, and the mixture was extracted with ethyl acetate and tetrahydrofuran. The extract was washed twice with water, saturated brine and saturated aqueous sodium hydrogen carbonate solution, dried over anhydrous magnesium sulfate, and concentrated under reduced pressure. The residue was recrystallized from ethanol to give the title compound as white crystals (yield 9.0 g, yield 51%).

$^1$H-NMR(CDCl$_3$)δ:4.69(2H,s), 7.25(1H,brs), 7.47(1H,brs), 7.75-7.79(2H,m), 7.88-7.92(2H,s).

Reference Example 26

2-{[4-phenyl-5-(phenylthio)-1,3-thiazol-2-yl]methyl}-1H-isoindole-1,3(2H)-dione

To a solution of 2-bromo-1-phenyl-2-(phenylthio)ethanone (3.2 g) in N,N-dimethylformamide (25 mL) was added 2-(1,3-dioxo-1,3-dihydro-2H-isoindol-2-yl)ethanethioamide (2.3 g) and the mixture was stirred at room temperature for 3 hr. A saturated aqueous sodium hydrogen carbonate solution was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was recrystallized from ethyl acetate-hexane to give the title compound as white crystals (yield 3.0 g, yield 71%).

$^1$H-NMR(CDCl$_3$)δ:5.19(2H,s), 7.15-7.28(5H,m), 7.33-7.40(3H,m), 7.75-7.79(2H,m), 7.88-7.93(4H,m).

Reference Example 27

2-{[4-(2-fluorophenyl)-5-(phenylthio)-1,3-thiazol-2-yl]methyl}-1H-isoindole-1,3(2H)-dione To a solution of 2-bromo-1-(2-fluorophenyl)-2-(phenylthio)ethanone (496 mg) in N,N-dimethylformamide (5 mL) was added 2-(1,3-dioxo-1,3-dihydro-2H-isoindol-2-yl) ethanethioamide (357 mg), and the mixture was stirred at room temperature for 12 hr. An aqueous sodium hydrogen carbonate solution was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by silica gel column chromatography (eluent: hexane-ethyl acetate=4:1→2:1) to give the title compound as a pale-yellow oil (yield 351 mg, yield 51%).
$^1$H-NMR(CDCl$_3$)δ:5.19(2H,s), 7.08-7.24(7H,m), 7.31-7.39(1H,m), 7.43-7.49(1H,m), 7.72-7.77(2H,m), 7.86-7.92(2H,m).

Reference Example 28

4-(2-fluoropyridin-3-yl)thiophene-2-carbaldehyde

A suspension of 4-bromothiophene-2-carbaldehyde (10.0 g), 2-fluoro-3-pyridineboronic acid (9.1 g), tetrakis(triphenylphosphine)palladium (0) (3.1 g) and sodium carbonate (13.7 g) in 1,2-dimethoxyethane (100 mL) and water (50 mL) was stirred at 80° C. for 20 hr under a nitrogen atmosphere. The reaction mixture was cooled to room temperature, water was added, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by silica gel column chromatography (eluent: hexane-ethyl acetate=2:1) to give the title compound as a pale-yellow solid (yield 5.8 g, yield 53%).
$^1$H-NMR(CDCl$_3$)δ:7.28-7.32(1H,m), 7.96-8.11(3H,m), 8.19-8.22(1H,m), 9.99(1H,d,J=1.2 Hz).

Reference Example 29

5-bromo-4-(2-fluoropyridin-3-yl)thiophene-2-carbaldehyde 4-(2-Fluoropyridin-3-yl)thiophene-2-carbaldehyde (3.35 g) was dissolved in acetic acid (20 mL) and N,N-dimethylformamide (20 mL), and bromine (7.77 g) was added at room temperature. The reaction mixture was stirred overnight and concentrated under reduced pressure. The residue was weakly basified with saturated aqueous sodium hydrogen carbonate solution, and the mixture was extracted with ethyl acetate. The extract was washed with saturated aqueous sodium thiosulfate solution, saturated aqueous sodium hydrogen carbonate solution and saturated brine in this order, dried over anhydrous sodium sulfate, and concentrated under reduced pressure. The residue was purified by silica gel column chromatography (eluent: hexane:ethyl acetate=6:1→3:1), and the obtained solid was washed with diisopropyl ether to give the title compound as a pale-yellow powder (yield 1.79 g, 39%).
$^1$H-NMR(CDCl$_3$)δ:7.30-7.35(1H,m), 7.71(1H,d,J=2.1 Hz), 7.92-7.99(1H,m), 8.28-8.31(1H,m), 9.83(1H,s).

Reference Example 30

4-(2-fluoropyridin-3-yl)-5-[(pyridin-2-yl)thio]thiophene-2-carbaldehyde

A suspension of 5-bromo-4-(2-fluoropyridin-3-yl) thiophene-2-carbaldehyde (297 mg), potassium carbonate (171 mg) and 2-mercaptopyridine (129 mg) in N,N-dimethylformamide (5 mL) was stirred at room temperature for 2 days. Water was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure. The residue was washed with diisopropyl ether to give the title compound as a pale-yellow solid (yield 281 mg, yield 85%).
$^1$H-NMR(CDCl$_3$)δ:7.06-7.11(2H,m), 7.19-7.24(1H,m), 7.52-7.57(1H,m), 7.89-7.97(2H,m), 8.19-8.22(1H,m), 8.40-8.43(1H,m), 9.91(1H,s).

Reference Example 31

4-(2-fluoropyridin-3-yl)-5-[(thiazol-2-yl)thio]thiophene-2-carbaldehyde

With 5-bromo-4-(2-fluoropyridin-3-yl)thiophene-2-carbaldehyde (250 mg) as a starting material, and using 2-mercaptothiazole (134 mg) and potassium carbonate (193 mg), an operation similar to that of Reference Example 1 was performed to give the title compound as a white powder (yield 282 mg, yield 100%).
$^1$H-NMR(CDCl$_3$)δ:7.27-7.33(1H,m), 7.34(1H,d,J=3.4 Hz), 7.74(1H,d,J=3.2 Hz), 7.87(1H,d,J=2.3 Hz), 7.98-8.05(1H,m), 8.26-8.30(1H,m), 9.92(1H,s).

Reference Example 32

4-(2-fluoropyridin-3-yl)-5-[(2-methylfuran-3-yl)thio]thiophene-2-carbaldehyde With 5-bromo-4-(2-fluoropyridin-3-yl)thiophene-2-carbaldehyde (250 mg) as a starting material, and using 2-methyl-3-furanthiol (0.114 mL) and potassium carbonate (193 mg), an operation similar to that of Reference Example 1 was performed to give the title compound as a pale-yellow oil (yield 271 mg, yield 97%).
$^1$H-NMR(CDCl$_3$)δ:2.37(3H,s), 6.38(1H,d,J=1.9 Hz), 7.31-7.37(1H,m), 7.39(1H,d,J=1.9 Hz), 7.74(1H,d,J=2.3 Hz), 7.98-8.06(1H,m), 8.25-8.30(1H,m), 9.74(1H,s).

Reference Example 33

4-(2-fluoropyridin-3-yl)-5-(phenylthio)thiophene-2-carbaldehyde

With 5-bromo-4-(2-fluoropyridin-3-yl)thiophene-2-carbaldehyde (2.86 g) as a starting material, and using thiophenol (1.33 mL) and potassium carbonate (2.21 g), an operation similar to that of Reference Example 1 was performed to give the title compound as a pale-yellow oil (yield 3.11 g, yield 99%).
$^1$H-NMR(CDCl$_3$)δ:7.27-7.31(1H,m), 7.32-7.43(5H,m), 7.79(1H,d,J=2.3 Hz), 7.90-7.99(1H,m), 8.23-8.27(1H,m), 9.80(1H,s).

Reference Example 34

4,5-bis(2-fluorophenyl)thiophene-2-carbaldehyde

A suspension of 4,5-dibromothiophene-2-carbaldehyde (2.0 g), (2-fluorophenyl)boronic acid (1.6 g), tetrakis(triphenylphosphine)palladium (0) (855 mg) and sodium carbonate (2.0 g) in 1,2-dimethoxyethane (32 mL) and water (8 mL) was stirred at 80° C. for 6 hr under a nitrogen atmosphere. The reaction mixture was cooled to room temperature, water was added, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by silica gel column chromatography (eluent: hexane-ethyl acetate=99:1→9:1→17:3) to give the title compound as a colorless amorphous (yield 310 mg, yield 14%).
$^1$H-NMR(CDCl$_3$)δ:7.04-7.13(5H,m), 7.26-7.40(3H,m), 8.87(1H,d,J=1.5 Hz), 9.96(1H,s).

Reference Example 35 ethyl 1-(2,5-difluorophenyl)-5-hydroxy-1H-pyrazole-3-carboxylate

To a solution of (2,5-difluorophenyl)hydrazine hydrochloride (25.0 g) in ethanol (500 mL) were added potassium carbonate (38.3 g) and diethyl but-2-ynedioate (23.6 g). After refluxing for 18 hr, the mixture was cooled to 0° C. and acidified with 6 mol/L hydrochloric acid. Ethanol was evaporated under reduced pressure, and the residue was extracted with ethyl acetate. The extract was washed with saturated brine, dried over anhydrous sodium sulfate, and concentrated under reduced pressure. The residue was washed with a mixed solvent of ethyl acetate and diisopropyl ether, and the obtained solid was collected by filtration and dried under reduced pressure to give the title compound as a pale-yellow solid (yield 22.7 g, yield 61%).

$^1$H-NMR(DMSO-d$_6$)δ:1.28(3H,t,J=7.2 Hz), 4.26(2H,q, J=7.2 Hz), 5.91(1H,s), 7.40-7.56(3H,m), 12.05(1H,br).

Reference Example 36 ethyl 1-(2-chlorophenyl)-5-{[(trifluoromethyl)sulfonyl]oxy}-1H-pyrazole-3-carboxylate To a solution of ethyl 1-(2-chlorophenyl)-5-hydroxy-1H-pyrazole-3-carboxylate (2.0 g) synthesized according to the method of US2004/214855 in tetrahydrofuran (15 mL) were added triethylamine (917 mg) and N-phenylbis(trifluoromethanesulfonimide) (3.2 g). After stirring at room temperature for 1 hr, water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=19:1→7:1) to give the title compound as a yellow oil (yield 2.85 g, yield 95%).

$^1$H-NMR(CDCl$_3$)δ:1.42(3H,t,J=7.2 Hz), 4.44(2H,q,J=7.2 Hz), 6.84(1H,s), 7.25-7.58(4H,m).

Reference Example 37 ethyl 1-(2,5-difluorophenyl)-5-{[(trifluoromethyl)sulfonyl]oxy}-1H-pyrazole-3-carboxylate To a solution of ethyl 1-(2,5-difluorophenyl)-5-hydroxy-1H-pyrazole-3-carboxylate (2.0 g) in tetrahydrofuran (20 mL) were added triethylamine (905 mg) and N-phenylbis(trifluoromethanesulfonimide) (3.2 g). After stirring at room temperature for 30 min, water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=19:1→9:1) to give the title compound as a yellow oil (yield 3.4 g, yield quantitatively).

$^1$H-NMR(CDCl$_3$)δ:1.42(3H,t,J=7.2 Hz), 4.45(2H,q,J=7.2 Hz), 6.85(1H,s), 7.23-7.42(3H,m).

Reference Example 38 ethyl 1-(2-chlorophenyl)-5-({3-[(2-ethylhexyl)oxy]-3-oxopropyl}thio)-1H-pyrazole-3-carboxylate A solution of ethyl 1-(2-chlorophenyl)-5-{[(trifluoromethyl)sulfonyl]oxy}-1H-pyrazole-3-carboxylate (2.85 g), 2-ethylhexyl 3-mercaptopropionate (2.34 g) and N-ethyldiisopropylamine (1.85 g) in toluene (30 mL) was sufficiently deaerated, tris(dibenzylideneacetone)dipalladium (0) (327 mg) and 4,5-bis(diphenylphosphino)-9,9-dimethylxanthene (414 mg) were added, and the mixture was further deaerated. Under an argon atmosphere, the reaction mixture was stirred at 110° C. for 4 hr, and allowed to cool to room temperature. Water was added, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=19:1→7:1) to give the title compound as a yellow oil (yield 2.87 g, yield 86%).

$^1$H-NMR(CDCl$_3$)δ:0.85-0.91(6H,m), 1.23-1.38(8H,m), 1.41(3H,t,J=7.2 Hz), 1.50-1.60(1H,m), 2.57(2H,t,J=7.5 Hz), 2.93(2H,t,J=7.5 Hz), 3.92-4.02(2H,m), 4.43(2H,q,J=7.2 Hz), 7.04(1H,s), 7.36-7.55(4H,m).

Reference Example 39 ethyl 1-(2,5-difluorophenyl)-5-({3-[(2-ethylhexyl)oxy]-3-oxopropyl}thio)-1H-pyrazole-3-carboxylate A solution of ethyl 1-(2,5-difluorophenyl)-5-{[(trifluoromethyl)sulfonyl]oxy}-1H-pyrazole-3-carboxylate (3.4 g), 2-ethylhexyl 3-mercaptopropionate (2.4 g) and N-ethyldiisopropylamine (1.9 g) in toluene (30 mL) was sufficiently deaerated, tris(dibenzylideneacetone)dipalladium (0) (342 mg) and 4,5-bis(diphenylphosphino)-9,9-dimethylxanthene (432 mg) were added, and the mixture was further deaerated. Under an argon atmosphere, the reaction mixture was stirred at 110° C. for 2 hr, and allowed to cool to room temperature. Water and ethyl acetate were added, and the mixture was filtered through celite. The organic layer of the filtrate was washed with saturated brine, dried over anhydrous sodium sulfate, and concentrated under reduced pressure. The residue was purified by silica gel column chromatography (eluent: hexane-ethyl acetate=19:1→7:1) to give the title compound as a yellow oil (yield 1.8 g, yield 53%).

$^1$H-NMR(CDCl$_3$)δ:0.85-0.91(6H,m), 1.24-1.43(11H,m), 1.50-1.60(1H,m), 2.57(2H,t,J=7.2 Hz), 2.97(2H,t,J=7.2 Hz), 3.93-4.03(2H,m), 4.43(2H,q,J=7.2 Hz), 7.04(1H,s), 7.04(1H, s), 7.17-7.26(3H,m).

Reference Example 40 ethyl 5-[(3-bromophenyl)thio]-1-(2-chlorophenyl)-1H-pyrazole-3-carboxylate

A mixture of ethyl 1-(2-chlorophenyl)-5-({3-[(2-ethylhexyl)oxy]-3-oxopropyl}thio)-1H-pyrazole-3-carboxylate (1.21 g), sodium ethoxide (362 mg), 1-bromo-3-iodobenzene (775 mg), tris(dibenzylideneacetone)dipalladium (0) (97 mg), 9,9-dimethyl-4,5-bis(diphenylphosphino)xanthine (123 mg) and N-ethyldiisopropylamine (0.88 mL) was stirred at 80° C. for 12 hr in ethanol (10 mL) and toluene (15 mL). The reaction mixture was cooled to room temperature, and concentrated under reduced pressure. Water was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent:hexane-ethyl acetate=4:1) to give the title compound as a yellow oil (yield 689 mg, yield 61%).

$^1$H-NMR(CDCl$_3$)δ:1.42(3H,t,J=7.2 Hz), 4.44(2H,q,J=7.2 Hz), 6.98-7.33(7H,m), 7.38-7.49(2H,m).

Reference Example 41 ethyl 5-[(3-bromophenyl)thio]-1-(2,5-difluorophenyl)-1H-pyrazole-3-carboxylate

To a solution of ethyl 1-(2,5-difluorophenyl)-5-({3-[(2-ethylhexyl)oxy]-3-oxopropyl}thio)-1H-pyrazole-3-carboxylate (1.95 g) in ethanol (20 mL) was added sodium ethoxide (569 mg) at 0° C. The mixture was stirred at room temperature for 1 hr, and the reaction mixture was concentrated under reduced pressure. A mixture of the residue, 1-bromo-3-iodobenzene (1.20 g), tris(dibenzylideneacetone)dipalladium (0) (38 mg) and 9,9-dimethyl-4,5-bis(diphenylphosphino)xanthene (49 mg) was stirred at 80° C. for 2 hr in toluene (20 mL). The reaction mixture was cooled to room temperature, water was added, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent:hexane-ethyl acetate=6:1) to give the title compound as a yellow oil (yield 2.04 g, yield quantitatively).

$^1$H-NMR(CDCl$_3$)δ:1.41(3H,t,J=7.2 Hz), 4.44(2H,q,J=7.2 Hz), 6.98-7.19(7H,m), 7.32-7.35(1H,m).

Reference Example 42 ethyl 1-(2-chlorophenyl)-5-[(6-methylpyridin-2-yl)thio]-1H-pyrazole-3-carboxylate To a solution of ethyl 1-(2-chlorophenyl)-5-({3-[(2-ethylhexyl)oxy]-3-oxopropyl}thio)-1H-pyrazole-3-carboxylate (1.09 g) in ethanol (10 mL) was added sodium ethoxide (320 mg) at 0° C. The mixture was stirred at room temperature for 1 hr, and concentrated under reduced pressure. A mixture of the residue, 2-bromo-6-methylpyridine (456 mg), tris(dibenzylideneacetone)dipalladium (0) (86 mg) and 9,9-dimethyl-4,5-bis(diphenylphosphino)xanthene (108 mg) was stirred at 80° C. for 3 hr in toluene (10 mL). The reaction mixture was cooled to room temperature, water was added, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent:hexane-ethyl acetate=4:1→3:1) to give the title compound as a yellow oil (yield 645 mg, yield 74%).

$^1$H-NMR(CDCl$_3$)δ:1.42(3H,t,J=7.2 Hz), 2.42(3H,s), 4.45(2H,q,J=7.2 Hz), 6.68(1H,d,J=7.8 Hz), 6.86(1H,d,J=7.8 Hz), 7.21-7.26(2H,m), 7.32-7.39(3H,m), 7.44-7.47(1H,m).

Reference Example 43 ethyl 1-(2-chlorophenyl)-5-[(6-methoxypyridin-2-yl)thio]-1H-pyrazole-3-carboxylate To a solution of ethyl 1-(2-chlorophenyl)-5-({3-[(2-ethylhexyl)oxy]-3-oxopropyl}thio)-1H-pyrazole-3-carboxylate (1.06 g) in ethanol (10 mL) was added sodium ethoxide (314 mg) at 0° C. The mixture was stirred at room temperature for 1 hr, and concentrated under reduced pressure. A mixture of the residue, 2-bromo-6-methoxypyridine (462 mg), tris(dibenzylideneacetone)dipalladium (0) (83 mg) and 9,9-dimethyl-4,5-bis(diphenylphosphino)xanthene (106 mg) was stirred at 80° C. for 4 hr in toluene (10 mL). The reaction mixture was cooled to room temperature, water was added, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent:hexane-ethyl acetate=4:1) to give the title compound as a yellow oil (yield 599 mg, yield 68%).

$^1$H-NMR(CDCl$_3$)δ:1.42(3H,t,J=7.2 Hz), 3.75(3H,s), 4.45(2H,q,J=7.2 Hz), 6.44-6.50(2H,m), 7.22-7.41(5H,m), 7.46-7.49(1H,m).

Reference Example 44 ethyl 1-(2-chlorophenyl)-5-[(5-methylpyridin-2-yl)thio]-1H-pyrazole-3-carboxylate To a solution of ethyl 1-(2-chlorophenyl)-5-({3-[(2-ethylhexyl)oxy]-3-oxopropyl}thio)-1H-pyrazole-3-carboxylate (1.15 g) in ethanol (15 mL) was added sodium ethoxide (337 mg) at 0° C. The mixture was stirred at room temperature for 1 hr, and concentrated under reduced pressure. A mixture of the residue, 2-bromo-5-methylpyridine (452 mg), tris(dibenzylideneacetone)dipalladium (92 mg) and 9,9-dimethyl-4,5-bis(diphenylphosphino)xanthene (115 mg) was stirred at 90° C. for 6 hr in toluene (10 mL). The reaction mixture was cooled to room temperature, water was added, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent:hexane-ethyl acetate=2:1) to give the title compound as a yellow oil (yield 668 mg, yield 73%).

$^1$H-NMR(CDCl$_3$)δ:1.42(3H,t,J=7.2 Hz), 2.25(3H,s), 4.44(2H,q,J=7.2 Hz), 6.81-6.84(1H,m), 7.20-7.39(5H,m), 7.40-7.47(1H,m), 8.16-8.17(1H,m).

Reference Example 45 ethyl 1-(2-chlorophenyl)-5-[(6-chloropyridin-3-yl)thio]-1H-pyrazole-3-carboxylate To a solution of ethyl 1-(2-chlorophenyl)-5-({3-[(2-ethylhexyl)oxy]-3-oxopropyl}thio)-1H-pyrazole-3-carboxylate (2.87 g) in ethanol (30 mL) was added sodium ethoxide (1.67 g) and the mixture was stirred at room temperature for 2 hr. About half amount of ethanol was evaporated under reduced pressure, and the reaction mixture was dissolved in toluene (10 mL). 2-Chloro-5-iodopyridine (1.62 g) was added and the mixture was deaerated. Tris(dibenzylideneacetone)dipalladium (0) (282 mg) and 4,5-bis(diphenylphosphino)-9,9-dimethylxanthene (356 mg) were added, and the mixture was further deaerated. Under an argon atmosphere, the mixture was stirred at 110° C. for 2 hr, and allowed to cool to room temperature. Water was added, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=19:1→7:1) to give the title compound as a purple oily substance (yield 2.06 g, yield 85%).

$^1$H-NMR(CDCl$_3$)δ:1.41(3H,t,J=7.2 Hz), 4.43(2H,q,J=7.2 Hz), 7.16-7.26(2H,m), 7.30-7.52(5H,m), 8.03-8.04(1H,m).

Reference Example 46

5-[(3-bromophenyl)thio]-1-(2-chlorophenyl)-N-methyl-1H-pyrazole-3-carboxamide

To a solution of ethyl 5-[(3-bromophenyl)thio]-1-(2-chlorophenyl)-1H-pyrazole-3-carboxylate (687 mg) in methanol (8 mL) was added 40% methylamine-methanol solution (1.6 mL) at 0° C. The reaction mixture was stirred at room temperature for 3 hr, and concentrated under reduced pressure. A saturated aqueous sodium hydrogen carbonate solution was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure to give the title compound as a yellow oil (yield 600 mg, yield 90%).
$^1$H-NMR(CDCl$_3$)δ:2.97(3H,d,J=5.1 Hz), 6.86(1H,brs), 6.98-7.33(7H,m), 7.38-7.51(2H,m).

Reference Example 47

5-[(3-bromophenyl)thio]-1-(2,5-difluorophenyl)-N-methyl-1H-pyrazole-3-carboxamide To a solution of ethyl 5-[(3-bromophenyl)thio]-1-(2,5-difluorophenyl)-1H-pyrazole-3-carboxylate (2.04 g) in methanol (2 mL) was added 40% methylamine-methanol solution (4 mL) at 0° C. The reaction mixture was stirred at room temperature for 3 hr, and concentrated under reduced pressure. A saturated aqueous sodium hydrogen carbonate solution was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (eluent:hexane-ethyl acetate=2:1) to give the title compound as a yellow oil (yield 1.35 g, yield 76%).
$^1$H-NMR(CDCl$_3$)δ:2.99(3H,d,J=5.1 Hz), 6.86(1H,brs), 6.98-7.10(3H,m), 7.14-7.20(4H,m), 7.30-7.34(1H,m).

Reference Example 48

1-(2-chlorophenyl)-5-[(6-methylpyridin-2-yl)thio]-1H-pyrazole-3-carbaldehyde

To a solution of ethyl 1-(2-chlorophenyl)-5-[(6-methylpyridin-2-yl)thio]-1H-pyrazole-3-carboxylate (640 mg) in tetrahydrofuran (10 mL) was added a 1.5 mol/L solution (4.6 mL) of diisobutylaluminum hydride in toluene at −78° C. and the mixture was stirred at the same temperature for 30 min. 1 mol/L Aqueous sodium hydroxide solution was added to the reaction mixture, insoluble materials were filtered off, and the filtrate was extracted with ethyl acetate. The extract was washed with water and saturated brine, dried over anhydrous sodium sulfate, and concentrated under reduced pressure. To a solution of the residue in toluene (7 mL) was added manganese dioxide (968 mg) and the mixture was stirred at 80° C. for 1 hr. The reaction mixture was cooled to room temperature and filtered, and the filtrate was concentrated under reduced pressure. The residue was purified by silica gel column chromatography (eluent:hexane-ethyl acetate=2:1) to give the title compound as a yellow oil (yield 420 mg, yield 74%).
$^1$H-NMR(CDCl$_3$)δ:2.42(3H,s), 6.71(1H,d,J=7.8 Hz), 6.88 (1H,d,J=7.8 Hz), 7.22-7.43(5H,m), 7.49-7.52(1H,m), 10.05 (1H,s).

Reference Example 49

1-(2-chlorophenyl)-5-[(6-methoxypyridin-2-yl)thio]-1H-pyrazole-3-carbaldehyde

To a solution of ethyl 1-(2-chlorophenyl)-5-[(6-methoxypyridin-2-yl)thio]-1H-pyrazole-3-carboxylate (594 mg) in tetrahydrofuran (6 mL) was added a solution (3 mL) of 1.5 mol/L diisobutylaluminum hydride in toluene at −78° C., and the mixture was stirred at the same temperature for 30 min and at −30° C. for 1 hr. 1 mol/L Aqueous sodium hydroxide solution was added to the reaction mixture, and the mixture was extracted with ethyl acetate. The extract was washed with water and saturated brine, dried over anhydrous sodium sulfate, and concentrated under reduced pressure. To a solution of the residue in toluene (8 mL) was added manganese dioxide (1.79 g) and the mixture was stirred at 80° C. for 1 hr. The reaction mixture was cooled to room temperature and filtered, and the filtrate was concentrated under reduced pressure. The residue was purified by silica gel column chromatography (eluent: hexane-ethyl acetate=4:1) to give the title compound as a yellow oil (yield 406 mg, yield 77%).
$^1$H-NMR(CDCl$_3$)δ:3.73(3H,s), 6.45-6.53(2H,m), 7.27-7.45(5H,m), 7.51-7.54(1H,m), 10.04(1H,s).

Reference Example 50

1-(2-chlorophenyl)-5-[(5-methylpyridin-2-yl)thio]-1H-pyrazole-3-carbaldehyde

To a solution of ethyl 1-(2-chlorophenyl)-5-[(5-methylpyridin-2-yl)thio]-1H-pyrazole-3-carboxylate (642 mg) in tetrahydrofuran (10 mL) was added a 1.5 mol/L solution (3.4 mL) of diisobutylaluminum hydride in toluene at −78° C., and the mixture was stirred at 0° C. for 1 hr. 1 mol/L Aqueous sodium hydroxide solution was added to the reaction mixture, and the mixture was extracted with ethyl acetate. The extract was washed with water, saturated aqueous sodium hydrogen carbonate solution and saturated brine, dried over anhydrous sodium sulfate, and concentrated under reduced pressure. To a solution of the residue in toluene (8 mL) was added manganese dioxide (1.38 g) and the mixture was stirred at 80° C. for 3 hr. The reaction mixture was cooled to room temperature and filtered, and the filtrate was concentrated under reduced pressure. The residue was purified by silica gel column chromatography (eluent:hexane-ethyl acetate=3:1) to give the title compound as a yellow oil (yield 426 mg, yield 80%).
$^1$H-NMR(CDCl$_3$)δ:2.25(3H,s), 6.85-6.87(1H,m), 7.24-7.43(5H,m), 7.49-7.52(1H,m), 8.17-8.18(1H,m), 10.03(1H, s).

Reference Example 51

1-(2-chlorophenyl)-5-[(6-chloropyridin-3-yl)thio]-N-methyl-1H-pyrazole-3-carboxamide To a solution of ethyl 1-(2-chlorophenyl)-5-[(6-chloropyridin-3-yl)thio]-1H-pyrazole-3-carboxylate (2.06 g) in methanol (4 mL) was added 40% methylamine-methanol solution (6 mL) at room temperature and the mixture was stirred for 2 hr. The reaction mixture was concentrated under reduced pressure, and the residue was purified by silica gel column chromatography (eluent:hexane-ethyl acetate=9:1→4:1) to give the title compound as a pale-yellow amorphous form (yield 1.75 g, yield 88%).
$^1$H-NMR(CDCl$_3$)δ:2.97(3H,d,J=5.1 Hz), 6.85(1H,br), 7.16-7.26(2H,m), 7.33-7.53(5H,m), 7.99-8.01(1H,m).

Reference Example 52 tert-butyl({1-(2-chlorophenyl)-5-[(6-chloropyridin-3-yl)thio]-1H-pyrazol-3-yl}methyl)methylcarbamate To a suspension of lithium aluminum hydride (350 mg) in tetrahydrofuran (40 mL) was added aluminum chloride (3.69 g) under ice-cooling. After stirring at the same temperature for 15 min, a solution of 1-(2-chlorophenyl)-5-[(6-chloropyridin-3-yl)thio]-N-methyl-1H-pyrazole-3-carboxamide (1.75 g) in tetrahydrofuran (30 mL) was added dropwise under ice-cooling, and the mixture was stirred at room temperature for 2 hr. The reaction mixture was ice-cooled again, treated with 8 mol/L aqueous sodium hydroxide solution, dried over anhydrous sodium sulfate, and filtered. The filtrate was concentrated under reduced pressure, and ethyl acetate and saturated aqueous sodium hydrogen carbonate solution were added to the residue. Di-tert-butyl dicarbonate (1.21 g) was added and the mixture was stirred for 10 min. The ethyl acetate layer was washed with saturated brine, dried over anhydrous sodium sulfate, and concentrated under reduced pressure. The residue was purified by silica gel column chromatography (eluent:hexane-ethyl acetate=9:1→4:1) to give the title compound as a colorless oil (yield 1.32 g, yield 62%).
$^1$H-NMR(CDCl$_3$)δ:1.50(9H,s), 2.88(3H,br), 4.45(2H,br), 6.60(1H,brd),7.14-7.50(6H,m), 7.99-8.00(1H,m).

Reference Example 53 ethyl 1-phenyl-5-[(phenylcarbonyl)amino]-1H-pyrazole-3-carboxylate

To a solution of ethyl 5-amino-1-phenyl-1H-pyrazole-3-carboxylate (498 mg) synthesized according to the method described in WO2004/98589 in N,N-dimethylacetamide (10 mL) were added N-ethyldiisopropylamine (417 mg) and benzoyl chloride (453 mg) at room temperature. After stirring at the same temperature for 18 hr, water was added and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=6:1→3:1) to give the title compound as colorless crystals (yield 550 mg, yield 76%).
$^1$H-NMR(CDCl$_3$)δ:1.42(3H,t,J=7.2 Hz), 4.44(2H,q,J=7.2 Hz), 7.36(1H,s), 7.43-7.59(8H,m), 7.69-7.73(2H,m), 7.95(1H,brs).

Reference Example 54 ethyl 1-phenyl-5-[(phenylsulfonyl)amino]-1H-pyrazole-3-carboxylate

Ethyl 5-amino-1-phenyl-1H-pyrazole-3-carboxylate (498 mg) synthesized according to the method described in WO2004/98589 and 4-dimethylaminopyridine (21 mg) were dissolved in pyridine (10 mL), and benzenesulfonyl chloride (461 mg) was added at room temperature. After stirring at 85° C. for 8 hr, 1 mol/L hydrochloric acid was added, and the mixture was extracted with ethyl acetate. The extract was washed with 1 mol/L hydrochloric acid, water and saturated brine, dried over anhydrous sodium sulfate, and concentrated under reduced pressure. The residue was purified by silica gel column chromatography (eluent:hexane-ethyl acetate=1:1→ethyl acetate), and the obtained solid was washed with a mixed solvent of diisopropyl ether and ethyl acetate to give the title compound as a brown powder (yield 445 mg, yield 69%).
$^1$H-NMR(CDCl$_3$)δ:1.40(3H,t,J=7.2 Hz), 4.40(2H,q,J=7.2 Hz), 5.29(1H,s), 6.79(1H,s), 7.07-7.10(2H,m), 7.35-7.49(5H,m), 7.60-7.65(1H,m), 7.68-7.72(2H,m).

Reference Example 55 ethyl 1-phenyl-5-(phenylamino)-1H-pyrazole-3-carboxylate

Ethyl 5-amino-1-phenyl-1H-pyrazole-3-carboxylate (443 mg) synthesized according to the method described in WO2004/98589, iodobenzene (469 mg), cesium carbonate (1.2 g), tris(dibenzylideneacetone)dipalladium (0) (87 mg) and 4,5-bis(diphenylphosphino)-9,9-dimethylxanthene (111 mg) were suspended in toluene (10 mL) and tetrahydrofuran (2 mL), and the mixture was sufficiently deaerated, and stirred at 120° C. for 18 hr under an argon atmosphere. The reaction mixture was allowed to cool to room temperature, water and ethyl acetate were added, and the mixture was filtered through celite. The organic layer of the filtrate was washed with saturated brine, dried over anhydrous sodium sulfate, and concentrated under reduced pressure. The residue was purified by silica gel column chromatography (eluent: hexane-ethyl acetate=7:1→3:1), and the obtained solid was washed with a mixed solvent of diisopropyl ether and ethyl acetate to give the title compound as a pale-red solid (yield 345 mg, yield 59%).
$^1$H-NMR(CDCl$_3$)δ:1.41(3H,t,J=7.2 Hz), 4.43(2H,q,J=7.2 Hz), 5.54(1H,br), 6.69(1H,s), 6.94-6.99(3H,m), 7.25-7.31 (2H,m), 7.42-7.51(3H,m), 7.56-7.60(2H,m).

Reference Example 56

N-[3-(hydroxymethyl)-1-phenyl-1H-pyrazol-5-yl] benzamide

A solution of ethyl 1-phenyl-5-[(phenylcarbonyl)amino]-1H-pyrazole-3-carboxylate (550 mg) in tetrahydrofuran (10 mL) was cooled to −78° C., and a 1.5 mol/L solution (5.5 mL) of diisobutylaluminum hydride in toluene was added dropwise.
After stirring at 0° C. for 1 hr, the mixture was treated with 1.0 mol/L hydrochloric acid, and extracted with ethyl acetate. The extract was washed with 1 mol/L hydrochloric acid, water, saturated aqueous sodium hydrogen carbonate solution and saturated brine, dried over anhydrous sodium sulfate, and concentrated under reduced pressure to give the title compound as a white powder (yield 384 mg, yield 80%).
$^1$H-NMR(CDCl$_3$)δ:2.04(1H,t,J=6.0 Hz), 4.76(2H,q,J=6.0 Hz), 6.87(1H,s), 7.42-7.58(8H,m), 7.70-7.73(2H,m), 7.97(1H,brs).

Reference Example 57

N-[3-(hydroxymethyl)-1-phenyl-1H-pyrazol-5-yl] benzenesulfonamide

A solution of ethyl 1-phenyl-5-[(phenylsulfonyl)amino]-1H-pyrazole-3-carboxylate (445 mg) in tetrahydrofuran (10 mL) was cooled to −78° C., and a 1.5 mol/L solution (4 mL) of diisobutylaluminum hydride in toluene was added dropwise. After stirring at 0° C. for 1 hr, the mixture was treated with 1 mol/L hydrochloric acid, and extracted with ethyl acetate. The aqueous layer was extracted with ethyl acetate again, and the combined extracts were washed with 1.0 mol/L hydrochloric acid, water and saturated brine, dried over anhydrous sodium sulfate, and concentrated under reduced pressure. The residue was purified by silica gel column chromatography (eluent:hexane-ethyl acetate=1:1→1:3) to give the title compound as a pale-yellow oil (yield 379 mg, yield 96%).

$^1$H-NMR(CDCl$_3$)δ:1.59(1H,br), 4.65(2H,s), 6.23(1H,s), 7.09-7.12(2H,m), 7.35-7.37(3H,m), 7.42-7.48(2H,m), 7.57-7.62(1H,s), 7.69-7.72(2H,m), 1H not detected.

Reference Example 58

[1-phenyl-5-(phenylamino)-1H-pyrazol-3-yl]methanol

A solution of ethyl 1-phenyl-5-(phenylamino)-1H-pyrazole-3-carboxylate (345 mg) in tetrahydrofuran (10 mL) was cooled to −78° C., and a 1.5 mol/L solution (3.7 mL) of diisobutylaluminum hydride in toluene was added dropwise. After stirring at 0° C. for 1 hr, the mixture was treated with 1 mol/L hydrochloric acid, and extracted with ethyl acetate. The extract was washed with 1 mol/L hydrochloric acid, water, saturated aqueous sodium hydrogen carbonate solution and saturated brine, dried over anhydrous sodium sulfate, and concentrated under reduced pressure. The residue was purified by silica gel column chromatography (eluent:hexane-ethyl acetate=2:1→1:2) to give the title compound as a pale-yellow oil (yield 318 mg, yield quantitative).

$^1$H-NMR(CDCl$_3$)δ:2.22(1H,br), 4.70(2H,brd,J=3.9 Hz), 5.55(1H,brs), 6.19(1H,s), 6.90-6.97(3H,m), 7.23-7.28(2H,m), 7.33-7.38(1H,m), 7.43-7.48(2H,m), 7.53-7.56(2H,m).

Reference Example 59

N-(3-formyl-1-phenyl-1H-pyrazol-5-yl)benzamide

N-[3-(Hydroxymethyl)-1-phenyl-1H-pyrazol-5-yl]benzamide (384 mg) and triethylamine (2 mL) were dissolved in dimethyl sulfoxide (5 mL), and sulfur trioxide•pyridine complex (417 mg) was added at room temperature. After stirring at room temperature for 18 hr, sulfur trioxide•pyridine complex (417 mg) was further added at room temperature and the mixture was stirred for 2 hr. Water was added to the reaction mixture, and the mixture was extracted with ethyl acetate. The extract was washed with saturated brine, dried over anhydrous sodium sulfate, and concentrated under reduced pressure. The residue was washed with 2-propanol to give the title compound as a pale-yellow powder (yield 303 mg, yield 79%).

$^1$H-NMR(CDCl$_3$)δ:7.34(1H,s), 7.44-7.49(2H,m), 7.53-7.62(6H,m), 7.70-7.73(2H,m), 7.95(1H,brs), 10.00(1H,s).

Reference Example 60

N-(3-formyl-1-phenyl-1H-pyrazol-5-yl)benzenesulfonamide

N-[3-(Hydroxymethyl)-1-phenyl-1H-pyrazol-5-yl]benzenesulfonamide (379 mg) and triethylamine (1 mL) were dissolved in dimethyl sulfoxide (5 mL), and sulfur trioxide•pyridine complex (549 mg) was added at room temperature. After stirring at room temperature for 18 hr, 1 mol/L hydrochloric acid was added to the reaction mixture, and the mixture was extracted with ethyl acetate. The aqueous layer was extracted again with ethyl acetate, and the combined extracts were washed with water and saturated brine, dried over anhydrous sodium sulfate, and concentrated under reduced pressure. The residue was purified by silica gel column chromatography (eluent:hexane-ethyl acetate=1:1→1:3) to give the title compound as a pale-yellow oil (yield 331 mg, yield 88%).

$^1$H-NMR(CDCl$_3$)δ:6.67(1H,s), 7.21-7.26(2H,m), 7.41-7.52(5H,m), 7.61-7.75(3H,m), 9.89(1H,s), 1H not detected.

Reference Example 61

N-(3-formyl-1-phenyl-1H-pyrazol-5-yl)-N-methyl-benzenesulfonamide

To a solution of N-(3-formyl-1-phenyl-1H-pyrazol-5-yl)benzenesulfonamide (331 mg) in N,N-dimethylformamide (5 mL) were added potassium carbonate (182 mg) and iodomethane (215 mg) at room temperature. After stirring at room temperature for 1 hr, the mixture was further stirred at 80° C. for 1 hr, and allowed to cool to room temperature. Water was added and the mixture was extracted with ethyl acetate. The extract was washed with water and saturated brine, dried over anhydrous sodium sulfate, and concentrated under reduced pressure. The residue was purified by silica gel column chromatography (eluent:hexane-ethyl acetate=7:1→3:1) to give the title compound as a pale-yellow amorphous (yield 297 mg, yield 86%).

$^1$H-NMR(CDCl$_3$)δ:3.07(3H,s), 6.40(1H,s), 7.49-7.59(5H,m), 7.64-7.73(5H,m), 9.94(1H,s).

Reference Example 62

1-phenyl-5-(phenylamino)-1H-pyrazole-3-carbaldehyde

[1-Phenyl-5-(phenylamino)-1H-pyrazol-3-yl]methanol (318 mg) and triethylamine (1 mL) were dissolved in dimethyl sulfoxide (5 mL), and sulfur trioxide•pyridine complex (535 mg) was added at room temperature. After stirring at room temperature for 18 hr, water was added to the reaction mixture, and the mixture was extracted with ethyl acetate. The extract was washed with water and saturated brine, dried over anhydrous sodium sulfate, and concentrated under reduced pressure. The residue was purified by silica gel column chromatography (eluent:hexane-ethyl acetate=7:1→3:1) to give the title compound as a pale-yellow powder (yield 238 mg, yield 81%).

$^1$H-NMR(CDCl$_3$)δ:5.60(1H,brs), 6.64(1H,s), 6.96-7.00(3H,m), 7.25-7.31(2H,m), 7.45-7.62(5H,m), 9.94(1H,s).

Reference Example 63 tert-butyl methyl{[1-phenyl-5-(phenylamino)-1H-pyrazol-3-yl]methyl}carbamate

1-Phenyl-5-(phenylamino)-1H-pyrazole-3-carbaldehyde (238 mg) was dissolved in tetrahydrofuran (5 mL) and methanol (2 mL), and 40% methylamine-methanol solution (0.4 mL) was added at room temperature. After stirring for 18 hr, the reaction mixture was concentrated under reduced pressure. The residue was dissolved in methanol (3 mL), sodium borohydride (103 mg) was added under ice-cooling, and the mixture was further stirred at room temperature for 2 hr. The reaction mixture was treated with 1 mol/L hydrochloric acid, and the solvent was evaporated under reduced pressure. The residue was basified with saturated aqueous sodium hydrogen carbonate solution, and ethyl acetate was added. Di-tert-butyl bicarbonate (237 mg) was added and the mixture was stirred for 1 hr. The organic layer of the reaction mixture was washed with saturated brine, dried over anhydrous sodium sulfate, and concentrated under reduced pressure. The residue was purified by silica gel column chromatography (eluent:hexane-ethyl acetate=9:1→4:1) to give the title compound as a white powder (yield 290 mg, yield 85%).

$^1$H-NMR(CDCl$_3$)δ:1.49(9H,s), 2.92(3H,br), 4.41(2H,br), 5.51(1H,brs), 6.10(1H,br), 6.90-6.95(3H,m), 7.23-7.28(2H,m), 7.33-7.37(1H,m), 7.43-7.48(2H,m), 7.51-7.56(2H,m).

Reference Example 64 tert-butyl methyl({5-[methyl(phenyl)amino]-1-phenyl-1H-pyrazol-3-yl}methyl)carbamate To a suspension of sodium hydride (16 mg) in tetrahydrofuran (2 mL) and N,N-dimethylformamide (0.5 mL) was added tert-butyl methyl{[1-phenyl-5-(phenylamino)-1H-pyrazol-3-yl]methyl}carbamate (100 mg). After stirring at room temperature for 30 min, iodomethane (75 mg) was added, and the mixture was further stirred for 1 hr. Water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=9:1→4:1) to give the title compound as a pale-brown oil (yield 67 mg, yield 65%).

$^1$H-NMR(CDCl$_3$)δ:1.48(9H,s), 2.94(3H,br), 3.01(3H,s), 4.43(2H,br), 6.11(1H,br), 6.73-6.75(2H,m), 6.80-6.85(1H,m), 7.18-7.25(3H,m), 7.29-7.35(2H,m), 7.45-7.47(2H,m).

Reference Example 65 tert-butyl({5-[acetyl(phenyl)amino]-1-phenyl-1H-pyrazol-3-yl}methyl)methylcarbamate To a suspension of sodium hydride (17 mg) in tetrahydrofuran (2 mL) and N,N-dimethylformamide (1 mL) was added tert-butyl methyl{[1-phenyl-5-(phenylamino)-1H-pyrazol-3-yl]methyl}carbamate (108 mg). After stirring at room temperature for 15 min, acetyl chloride (45 mg) was added, and the mixture was further stirred for 1 hr. Water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=7:1→3:1) to give the title compound as a colorless oil (yield 83 mg, yield 69%).

$^1$H-NMR(CDCl$_3$)δ:1.49(9H,s), 2.00(3H,brs), 2.92(3H,br), 4.45(2H,br), 6.11(1H,br), 6.39(1H,br), 7.00(2H,br), 7.18-7.29(3H,m), 7.30-7.41(5H,m).

Example 1

N-methyl-1-[1-phenyl-2-(phenylthio)-1H-imidazol-4-yl]methanamine dihydrochloride To a solution of 1-phenyl-2-(phenylthio)-1H-imidazole-4-carbaldehyde (400 mg) in methanol (10 mL) was added 40% methylamine methanol solution (554 mg) at room temperature and the mixture was stirred for 30 min. Sodium borohydride (108 mg) was added and the mixture was stirred for 15 min. Water was added and the mixture was further stirred for 10 min. A saturated aqueous sodium hydrogen carbonate solution was added to the reaction mixture, and the mixture was extracted with ethyl acetate. The extract was washed with saturated brine, dried over anhydrous magnesium sulfate, and concentrated under reduced pressure. The residue was purified by basic silica gel column chromatography (eluent:ethyl acetate) and dissolved in methanol (5 mL). A 4 mol/L hydrogen chloride-ethyl acetate solution (1 mL) was added, and the mixture was concentrated under reduced pressure. The residue was crystallized from tetrahydrofuran to give the title compound as colorless crystals (yield 347 mg, yield 66%).

$^1$H-NMR(DMSO-d$_6$)δ:2.58(3H,t,J=5.5 Hz), 4.11(2H,t,J=5.5 Hz), 7.07-7.10(2H,m), 7.19-7.39(5H,m), 7.47-7.54(3H,m), 7.87(1H,s), 8.75(1H,br), 9.40(2H,br).

Example 2

N-methyl-1-[1-phenyl-2-(phenylsulfinyl)-1H-imidazol-4-yl]methanamine dihydrochloride To a solution of N-methyl-1-[1-phenyl-2-(phenylthio)-1H-imidazol-4-yl]methanamine dihydrochloride (70 mg) in acetone (20 mL) and water (10 mL) was added dropwise a solution of oxone (176 mg) in water (10 mL), and the mixture was stirred at room temperature for 5 hr. Sodium thiosulfate pentahydrate (1 g) was added to the reaction mixture and the mixture was stirred for 1 hr. A saturated aqueous sodium hydrogen carbonate solution was added, and the mixture was extracted with a mixed solution of ethyl acetate-tetrahydrofuran (1:1). The extract was dried over anhydrous sodium sulfate, and concentrated under reduced pressure. The residue was purified by basic silica gel column chromatography (eluent:ethyl acetate-methanol=1:0→7:3) and dissolved in methanol (5 mL). A 4 mol/L hydrogen chloride-ethyl acetate solution (1 mL) was added, and the mixture was concentrated under reduced pressure. The residue was dissolved in a mixed solution of methanol-tetrahydrofuran, and ethyl acetate was added. The precipitated insoluble materials were collected by filtration to give the title compound as a colorless powder (yield 34 mg, yield 47%).

$^1$H-NMR (DMSO-d$_6$) δ:2.56(3H,t,J=5.3 Hz), 4.09(2H,t,J=5.5 Hz), 7.36-7.60(10H,m), 7.85(1H,s), 9.16(2H,brs), 1H not detected.

Example 3

1-[1-(4-fluorobenzyl)-2-phenyl-1H-imidazol-4-yl]-N-methylmethanamine dihydrochloride To a solution of 2-phenyl-1H-imidazole-4-carbaldehyde (0.35 g) in dimethylformamide (5 mL) were added potassium carbonate (843 mg) and 1-(bromomethyl)-4-fluorobenzene (462 mg) and the mixture was stirred at 75° C. for 2 hr. Water was added to the reaction mixture, and the mixture was extracted with ethyl acetate. The extract was washed with saturated brine, dried over anhydrous magnesium sulfate, and concentrated under reduced pressure. The residue was dissolved in a mixture of 40% methylamine-methanol solution (474 mg) and methanol (5 mL), and the mixture was stirred for 5 min. Sodium borohydride (154 mg) was added and the mixture was stirred for 1 hr. Saturated sodium hydrogen carbonate solution was added to the reaction mixture, and the mixture was extracted with ethyl acetate. The extract was washed with saturated brine, dried over anhydrous magnesium sulfate, and concentrated under reduced pressure. The residue was purified by basic silica gel column chromatography (eluent:ethyl acetate-methanol=1:0→4:1) and dissolved in methanol. A 4 mol/L hydrogen chloride-ethyl acetate solution (2 mL) was added, and the mixture was concentrated under reduced pressure. The residue was crystallized from a mixed solution of methanol-tetrahydrofuran (1:4) to give the title compound as colorless crystals (yield 450 mg, yield 60%). melting point: 169-171° C.
$^1$H-NMR(DMSO-d$_6$)δ:2.59(3H,t,J=5.1 Hz), 4.25(2H,t, J=4.9 Hz), 5.49(2H,s), 7.13-7.30(4H,m), 7.53-7.68(3H,m), 7.70-7.76(2H,m), 7.83(1H,s), 9.72(2H,brs), 1H not detected.

Example 4

2-{4-[(methylamino)methyl]-2-phenyl-1H-imidazol-1-yl}-2-phenylethanol dihydrochloride To a solution of methyl (4-formyl-2-phenyl-1H-imidazol-1-yl)(phenyl)acetate (200 mg) in methanol (10 mL) was added 40% methylamine methanol solution (243 mg) and the mixture was stirred for 15 min. Sodium borohydride (71 mg) was added and the mixture was stirred for 30 min. 1 mol/L Hydrochloric acid was added to the reaction mixture and the mixture was stirred for 5 min. The mixture was neutralized with saturated sodium hydrogen carbonate solution, and extracted with ethyl acetate-tetrahydrofuran (1:1). The extract was dried over anhydrous magnesium sulfate, and concentrated under reduced pressure. The residue was purified by basic silica gel column chromatography (eluent:ethyl acetate-methanol=1:0→3:2) and dissolved in methanol (5 mL). A 4 mol/L hydrogen chloride-ethyl acetate solution (1 mL) was added, and the mixture was concentrated under reduced pressure. Ethyl acetate was added to the residue, and insoluble materials were collected by filtration to give the title compound as a colorless powder (yield 63 mg, yield 27%).
$^1$H-NMR(DMSO-d$_6$)δ:2.63(3H,t,J=5.3 Hz), 3.91-4.23 (2H,m), 4.25(2H,br), 5.59(1H,dd,J=8.1,4.1 Hz), 7.25(2H,dd, J=7.4,1.8 Hz), 7.32-7.48(3H,m), 7.63(5H,br), 8.16(1H,brs), 9.58(2H,brs), 2H not detected.

Example 5 methyl{4-[(methylamino)methyl]-2-phenyl-1H-imidazol-1-yl}(phenyl)acetate dihydrochloride To a solution of methyl (4-formyl-2-phenyl-1H-imidazol-1-yl)(phenyl)acetate (200 mg) in methanol (10 mL) was added 40% methylamine methanol solution (243 mg) and the mixture was stirred for 15 min. Sodium borohydride (24 mg) was added and the mixture was stirred for 30 min. 1 mol/L Hydrochloric acid was added to the reaction mixture and the mixture was stirred for 5 min. The mixture was neutralized with saturated sodium hydrogen carbonate solution and extracted with ethyl acetate-tetrahydrofuran (1:1). The extract was dried over anhydrous magnesium sulfate, and concentrated under reduced pressure. The residue was purified by basic silica gel column chromatography (eluent:ethyl acetate) and dissolved in methanol (5 mL). A 4 mol/L hydrogen chloride-ethyl acetate solution (1 mL) was added and the mixture was concentrated under reduced pressure. Ethyl acetate was added to the residue, and insoluble materials were collected by filtration to give the title compound as a colorless powder (yield 101 mg, yield 40%).
$^1$H-NMR(DMSO-d$_6$)δ:2.54(3H,t,J=5.4 Hz), 3.66(3H,s), 4.10(2H,t,J=5.5 Hz), 6.42(1H,s), 7.34-7.70(11H,m), 9.22(2H,br), 1H not detected.

Example 6

1-[5-chloro-1-(4-fluorobenzyl)-2-phenyl-1H-imidazol-4-yl]-N-methylmethanamine oxalate To a solution of 1-[1-(4-fluorobenzyl)-2-phenyl-1H-imidazol-4-yl]-N-methylmethanamine dihydrochloride (100 mg) in dimethylformamide was added N-chlorosuccinimide (43 mg) and the mixture was stirred at room temperature for 3 hr. Water and saturated sodium hydrogen carbonate solution were added to the reaction mixture, and the mixture was extracted with ethyl acetate. The extract was washed with saturated brine, dried over anhydrous magnesium sulfate, and concentrated under reduced pressure. The residue was purified by basic silica gel column chromatography (eluent:ethyl acetate-methanol=19:1→3:2), a solution of oxalic acid (25 mg) in ethyl acetate (5 mL) was added, and the mixture was crystallized to give the title compound as colorless crystals (yield 20 mg, yield 18%).
melting point: 172-174° C.
$^1$H-NMR(DMSO-d$_6$)δ:2.64(3H,s), 4.10(2H,s), 5.34(2H,s), 7.00-7.06(2H,m), 7.16-7.22(2H,m), 7.46-7.56 (5H,m), 3H not detected.

Example 7

N-methyl-1-[2-phenyl-1-(pyrimidin-2-yl)-1H-imidazol-4-yl]methanamine dihydrochloride To a solution of 2-phenyl-1-pyrimidin-2-yl-1H-imidazole-4-carbaldehyde (150 mg) in methanol (15 mL) was added 40% methylamine-methanol solution (233 mg) and the mixture was stirred for 10 min. Sodium borohydride (68 mg) was added and the mixture was stirred for 10 min. 1 mol/L Hydrochloric acid was added to the reaction mixture and the mixture was stirred for 30 min. The mixture was neutralized with saturated sodium hydrogen carbonate solution, and extracted with tetrahydrofuran. The extract was dried over anhydrous magnesium sulfate, and concentrated under reduced pressure. The residue was purified by basic silica gel column chromatography (eluent:ethyl acetate-methanol=19:1→7:3) and dissolved in methanol (5 mL). A 4 mol/L hydrogen chloride-ethyl acetate solution (1 mL) was added, and the mixture was concentrated under reduced pressure. Tetrahydrofuran was added to the residue, and insoluble materials were collected by filtration to give the title compound as a colorless powder (yield 55 mg, yield 27%).
$^1$H-NMR(DMSO-d$_6$)δ:2.62(3H,t,J=5.5 Hz), 4.16(2H,t, J=5.5 Hz), 7.38-7.43(5H,m), 7.59(1H,t,J=4.9 Hz), 8.07(1H, s), 8.85(2H,d,J=4.9 Hz), 9.30(2H,br), 1H not detected.

Example 8

N-methyl-1-(1-{[(4-methylphenyl)thio]methyl}-2-phenyl-1H-imidazol-4-yl)methanamine dihydrochloride To a solution of tert-butyl methyl[(2-phenyl-1H-imidazol-4-yl)methyl]carbamate (350 mg) in dimethylformamide (5 mL) was added sodium hydride (60% in oil, 421 mg) and the mixture was stirred for 1 hr. 1-[(Chloromethyl)thio]-4-methylbenzene (316 mg) was added dropwise, and the mixture was stirred at 80° C. for 15 hr. The reaction mixture was diluted with water, and extracted with ethyl acetate. The extract was washed with water, 3% aqueous potassium hydrogensulfate solution, saturated sodium hydrogen carbonate solution and saturated brine in this order, dried over anhydrous magnesium sulfate, and concentrated under reduced pressure. The residue was purified by silica gel column chromatography (eluent:hexane-ethyl acetate=4:1→1:4) and dissolved in methanol (10 mL). A 4 mol/L hydrogen chloride-ethyl acetate solution (2 mL) was added and the mixture was stirred at 75° C. for 30 min. The reaction mixture was concentrated under reduced pressure, and the residue was crystallized from ethyl acetate to give the title compound as colorless crystals (yield 31 mg, yield 6.4%).

$^1$H-NMR(DMSO-d$_6$)δ:2.28(3H,s), 2.54(3H,t,J=5.4 Hz), 4.17(2H,br), 5.59(2H,s), 6.96-7.18(4H,m), 7.38-7.59(5H,m), 7.71(1H,brs), 9.47(2H,brs), 1H not detected.

Example 9

N-methyl-1-(1-{[(4-methylphenyl)sulfonyl]methyl}-2-phenyl-1H-imidazol-4-yl)methanamine dihydrochloride To a solution of N-methyl-1-(1-{[(4-methylphenyl)thio]methyl}-2-phenyl-1H-imidazol-4-yl)methanamine dihydrochloride (250 mg) in water (10 mL) and acetone (10 mL) was added dropwise a solution of oxone (700 mg) in water (20 mL), and the mixture was stirred at room temperature for 3 hr. Sodium thiosulfate pentahydrate (783 mg) was added to the reaction mixture and the mixture was stirred for 24 hr. A saturated aqueous sodium hydrogen carbonate solution was added, and the mixture was extracted with a mixed solution of ethyl acetate-tetrahydrofuran (1:1). The extract was dried over anhydrous sodium sulfate, and concentrated under reduced pressure. The residue was purified by basic silica gel column chromatography (eluent:ethyl acetate-methanol=1:0→7:3) and dissolved in methanol (5 mL). A 4 mol/L hydrogen chloride-ethyl acetate solution (1 mL) was added, and the mixture was concentrated under reduced pressure. The residue was crystallized from tetrahydrofuran to give the title compound as colorless crystals (yield 55 mg, yield 20%).

$^1$H-NMR(DMSO-d$_6$)δ:2.38(3H,s), 2.56(3H,t,J=5.5 Hz), 4.10(2H,t,J=5.3 Hz), 5.82(2H,s), 7.18-7.46(9H,m), 7.48(1H, s), 9.10(2H,brs), 1H not detected.

Example 10

1-{4-(2-fluorophenyl)-5-[(3-methoxyphenyl)thio]-2-thienyl}-N-methylmethanamine fumarate tert-Butyl ({4-(2-fluorophenyl)-5-[(3-methoxyphenyl)thio]-2-thienyl}methyl)methylcarbamate (182 mg) was dissolved in ethyl acetate (3 mL) and ethanol (1 mL), and a 4 mol/L hydrogen chloride-ethyl acetate solution (2 mL) was added at room temperature. After stirring for 6 hr, the reaction mixture was concentrated under reduced pressure. A saturated aqueous sodium hydrogen carbonate solution was added to the residue, and the mixture was extracted with ethyl acetate. The extract was washed with saturated brine, dried over anhydrous sodium sulfate, and concentrated under reduced pressure to give a free base of the title compound (149 mg). To a solution of fumaric acid (48 mg) in ethanol (10 mL) was added a solution of the obtained free base in ethyl acetate (5 mL), and the solvent was evaporated under reduced pressure. The obtained crude crystals were recrystallized from a mixed solvent of ethyl acetate and 2-propanol to give the title compound as colorless crystals (yield 118 mg, yield 63%).

melting point: 138-141° C.

$^1$H-NMR(DMSO-d$_6$)δ:2.40(3H,s), 3.67(3H,s), 4.03(2H,s), 6.54(2H,s), 6.55-6.57(1H,m), 6.61-6.64(1H,m), 6.72-6.76(1H,m), 7.16-7.45(6H,m), 3H not detected.

Example 11

1-{4-(2-fluorophenyl)-5-[(3-methoxyphenyl)sulfinyl]-2-thienyl}-N-methylmethanamine fumarate tert-Butyl ({4-(2-fluorophenyl)-5-[(3-methoxyphenyl)sulfinyl]-2-thienyl}methyl)methylcarbamate (231 mg) was dissolved in ethyl acetate (3 mL) and ethanol (1 mL), and a 4 mol/L hydrogen chloride-ethyl acetate solution (2 mL) was added at room temperature. After stirring for 4 hr, the reaction mixture was concentrated under reduced pressure. A saturated aqueous sodium hydrogen carbonate solution was added to the residue, and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=1:1→1:9) to give a free base of the title compound (155 mg) as a pale-yellow oil. To a solution of fumaric acid (50 mg) in ethanol (10 mL) was added a solution of the obtained free base in ethyl acetate (5 mL), and the solvent was evaporated under reduced pressure. The obtained crude crystals were recrystallized from a mixed solvent of ethyl acetate and 2-propanol to give the title compound as a white powder (yield 118 mg, yield 50%).

$^1$H-NMR(DMSO-d$_6$)δ:2.33(3H,s), 3.79(3H,s), 3.95(2H,s), 6.56(2H,s), 7.11-7.14(4H,m), 7.35-7.63(5H,m), 3H not detected.

Example 12

N-methyl-1-(5-phenoxy-4-phenyl-2-thienyl)methanamine fumarate

5-Phenoxy-4-phenylthiophene-2-carbaldehyde (152 mg) was dissolved in tetrahydrofuran (5 mL) and methanol (2 mL), and 40% methylamine-methanol solution (0.536 mL) was added. After stirring at room temperature overnight, the reaction mixture was concentrated under reduced pressure. The residue was dissolved in methanol (5 mL), sodium borohydride (62 mg) was added at room temperature and the mixture was further stirred for 4 hr. The solvent was evaporated under reduced pressure, water was added to the residue, and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=1:1→1:9) to give a free base of the title compound (yield 123 mg, yield 76%). To a solution of fumaric acid (48 mg) in ethanol (10 mL) was added a solution of the obtained free base in ethyl acetate (5 mL), and the solvent was evaporated under reduced pressure. The obtained crude crystals were recrystallized from ethanol to give the title compound as colorless crystals (yield 122 mg, yield 72%).

$^1$H-NMR(DMSO-d$_6$)δ:2.41(3H,s), 3.97(2H,s), 6.53(2H,s), 7.06-7.15(3H,m), 7.22-7.27(2H,m), 7.33-7.39 (4H,m), 7.58-7.61(2H,m), 3H not detected.

Example 13

{5-[(methylamino)methyl]-3-phenyl-2-thienyl}(phenyl)methanone hydrochloride tert-Butyl [(5-benzoyl-4-phenyl-2-thienyl)methyl]methylcarbamate (236 mg) was dissolved in ethyl acetate (3 mL), and a 4 mol/L hydrogen chloride-ethyl acetate solution (3 mL) was added at room temperature. After stirring for 1 hr, the reaction mixture was concentrated under reduced pressure. The residue was recrystallized from a mixed solvent of ethyl acetate and ethanol to give the title compound as colorless crystals (yield 114 mg, yield 57%).

$^1$H-NMR(DMSO-d$_6$)δ:2.61 (3H, s), 4.44(2H,s), 7.17-7.29 (7H,m), 7.41-7.45(1H,m), 7.47-7.57(3H,m), 9.34(2H,brs).

Example 14

{5-[(methylamino)methyl]-3-phenyl-2-thienyl}(phenyl)methanol 0.5 fumarate

The free base of {5-[(methylamino)methyl]-3-phenyl-2-thienyl}(phenyl)methanone (274 mg) obtained in Example 13 was dissolved in tetrahydrofuran (3 mL) and methanol (2 mL), and sodium borohydride (51 mg) was added at room temperature. After stirring for 3 hr, the solvent was evaporated under reduced pressure, water was added to the residue, and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=1:1→1:9) to give a free base of the title compound (106 mg) as a pale-yellow oil. To a solution of fumaric acid (40 mg) in ethanol (3 mL) was added a solution of the obtained free base in ethyl acetate (4 mL), and the solvent was evaporated under reduced pressure. The residue was crystallized from a mixed solvent of ethyl acetate and 2-propanol and recrystallized from ethanol to give the title compound as colorless crystals (yield 40 mg, yield 32%).

$^1$H-NMR (DMSO-d$_6$)δ:2.34(3H,s), 3.88(2H,s), 5.92(1H, s), 6.22(1H,br), 6.48(1H,s), 6.96(1H,s), 7.18-7.47(10H,m), 2H not detected.

Example 15

1-[4-phenyl-5-(phenylthio)-1,3-thiazol-2-yl]methanamine

To a suspension of 2-{[4-phenyl-5-(phenylthio)-1,3-thiazol-2-yl]methyl}-1H-isoindole-1,3(2H)-dione (0.53 g) in ethanol (5 mL) was added hydrazine monohydrate (0.1 mL) and the mixture was stirred at 70° C. for 1 hr. The reaction mixture was cooled to room temperature, water was added, and the mixture was extracted with ethyl acetate. The extract was washed with saturated aqueous sodium hydrogen carbonate solution, water and saturated brine, dried over anhydrous magnesium sulfate, and concentrated under reduced pressure to give the title compound as a yellow oil (yield 0.36 g, 97%).

$^1$H-NMR(CDCl$_3$)δ:1.72(2H,brs), 4.21(2H,s), 7.16-7.30 (5H,m), 7.35-7.43(3H,m), 7.88-7.92(2H,m).

Example 16

1-[4-(2-fluorophenyl)-5-(phenylthio)-1,3-thiazol-2-yl]methanamine

To a solution of 2-{[4-(2-fluorophenyl)-5-(phenylthio)-1,3-thiazol-2-yl]methyl}-1H-isoindole-1,3(2H)-dione (345 mg) in ethanol (5 mL) was added hydrazine monohydrate (0.05 mL) and the mixture was stirred at 70° C. for 3 hr. The reaction mixture was cooled to room temperature, saturated aqueous sodium hydrogen carbonate solution was added, and the mixture was extracted with ethyl acetate. The extract was washed with saturated aqueous sodium hydrogen carbonate solution, water and saturated brine, dried over anhydrous sodium sulfate, and concentrated under reduced pressure to give the title compound as a yellow oil (yield 209 mg, yield 86%).

$^1$H-NMR(CDCl$_3$)δ:4.20(2H,s), 7.10-7.27(7H,m), 7.33-7.40(1H,m), 7.44-7.49(1H,m), 2H not detected.

Example 17

1-{4-(2-fluoropyridin-3-yl)-5-[(pyridin-2-yl)thio]thiophen-2-yl}-N-methylmethanamine To a solution of 4-(2-fluoropyridin-3-yl)-5-[(pyridin-2-yl)thio]thiophene-2-carbaldehyde (270 mg) in tetrahydrofuran (2 mL) were added 40% methylamine-methanol solution (0.9 mL) and methanol (2 mL), and the mixture was stirred at room temperature for 2 days. The reaction mixture was concentrated under reduced pressure. The residue was dissolved in methanol (3 mL), and sodium tetrahydroborate (222 mg) was added at 0° C. The mixture was stirred at room temperature for 1 day and concentrated under reduced pressure. A saturated aqueous sodium hydrogen carbonate solution was added to the residue, and the mixture was extracted with ethyl acetate. The extract was washed with saturated aqueous sodium hydrogen carbonate solution, water and saturated brine, dried over anhydrous magnesium sulfate, and concentrated under reduced pressure to give the title compound as a pale-yellow oil (yield 286 mg, yield quantitative).

$^1$H-NMR(CDCl$_3$)δ:2.54(3H,s), 4.00(2H,d,J=1.2 Hz), 6.86-6.88(1H,m), 6.96-7.01(1H,m), 7.13-7.18(2H,m), 7.44-7.50(1H,m), 7.85-7.91(1H,m), 8.12-8.15(1H,m), 8.35-8.37(1H,m), 1H not detected.

Example 18

1-{4-(2-fluoropyridin-3-yl)-5-[(1,3-thiazol-2-yl)thio]thiophen-2-yl}-N-methylmethanamine fumarate 4-(2-Fluoropyridin-3-yl)-5-[(1,3-thiazol-2-yl)thio]thiophene-2-carbaldehyde (282 mg) was dissolved in tetrahydrofuran (3 mL) and methanol (3 mL), and 40% methylamine-methanol solution (0.899 mL) was added. After stirring at room temperature for 18 hr, the reaction mixture was concentrated under reduced pressure. The residue was dissolved in methanol (5 mL), sodium borohydride (166 mg) was added and the mixture was stirred at room temperature for 8 hr. The solvent was evaporated under reduced pressure, saturated aqueous sodium hydrogen carbonate solution was added to the residue, and the mixture was extracted with ethyl acetate. The extract was washed with saturated aqueous sodium hydrogen carbonate solution and saturated brine, dried over anhydrous sodium sulfate, and concentrated under reduced pressure. The residue was purified by basic silica gel column chromatography (eluent:hexane-ethyl acetate=3:1→1:9) to give a free base of the title compound as a colorless oil (yield 132 mg). The obtained free base (120 mg) was dissolved in ethyl acetate (2 mL), and a solution of fumaric acid (41.3 mg) in ethanol (2 mL) was added. The reaction mixture was concentrated under reduced pressure, and the residue was recrystallized from a mixed solvent of ethanol and ethyl acetate to give the title compound as colorless crystals (yield 50 mg, yield 31%).

melting point: 140-143° C.

$^1$H-NMR(DMSO-d$_6$)δ:2.38(3H,s), 4.00(2H,s), 6.57(2H,s), 7.31-7.35(1H,m), 7.41-7.49(1H,m), 7.61-7.69(2H,m), 8.02-8.12(1H,m), 8.24-8.30(1H,m), 3H not detected.

Example 19

1-{4-(2-fluoropyridin-3-yl)-5-[(2-methylfuran-3-yl)thio]thiophen-2-yl}-N-methylmethanamine hydrochloride 4-(2-Fluoropyridin-3-yl)-5-[(2-methylfuran-3-yl)thio]thiophene-2-carbaldehyde (279 mg) was dissolved in tetrahydrofuran (3 mL) and methanol (3 mL), and 40% methylamine-methanol solution (0.899 mL) was added. After stirring at room temperature for 18 hr, the reaction mixture was concentrated under reduced pressure. The residue was dissolved in methanol (5 mL), sodium borohydride (166 mg) was added and the mixture was stirred at room temperature for 8 hr. The solvent was evaporated under reduced pressure, saturated aqueous sodium hydrogen carbonate solution was added to the residue, and the mixture was extracted with ethyl acetate. The extract was washed with saturated aqueous sodium hydrogen carbonate solution and saturated brine, dried over anhydrous sodium sulfate, and concentrated under reduced pressure. The residue was purified by basic silica gel column chromatography (eluent:hexane-ethyl acetate=3:1→2:3) to give a free base of the title compound as a colorless oil (yield 88 mg). The obtained free base (68.5 mg) was dissolved in ethyl acetate (1 mL), and a 4 mol/L hydrogen chloride-ethyl acetate solution (2 mL) was added. After stirring at room temperature for 0.5 hr, the reaction mixture was concentrated under reduced pressure, and the residue was recrystallized from a mixed solvent of ethanol and ethyl acetate to give the title compound as colorless crystals (yield 67.6 mg, yield 89%).

$^1$H-NMR(DMSO-d$_6$)δ:2.21(3H,s), 2.53(3H,s), 4.28(2H,brs), 6.38(1H,d,J=2.1 Hz), 7.33(1H,d,J=1.3 Hz), 7.48-7.56(1H,m), 7.62(1H,d,J=2.1 Hz), 8.01-8.11(1H,m), 8.29-8.36(1H,m), 8.96(2H,brs).

Example 20

1-{[4-(2-fluoropyridin-3-yl)-5-(phenylthio)thiophen-2-yl]methyl}azetidin-3-ol fumarate 4-(2-Fluoropyridin-3-yl)-5-(phenylthio)thiophene-2-carbaldehyde (158 mg) was dissolved in a mixed solvent of methanol (0.1 mL) and ethyl acetate (1 mL), 3-azetidinol (183 mg) was added, and the mixture was stirred at room temperature for 0.5 hr. Sodium triacetoxyborohydride (265 mg) was added to the reaction mixture under ice-cooling, and the mixture was stirred at room temperature for 18 hr. A saturated aqueous sodium hydrogen carbonate solution was added to the reaction mixture, and the mixture was stirred at room temperature for 0.5 hr and extracted with ethyl acetate. The extract was washed with saturated brine, dried over anhydrous magnesium sulfate, and concentrated under reduced pressure. The residue was purified by silica gel column chromatography (eluent:hexane-ethyl acetate=7:3→ethyl acetate→methanol-ethyl acetate=1:9) to give a free base of the title compound as a colorless oil (yield 98 mg). The obtained free base (98 mg) was dissolved in ethyl acetate (1 mL), and a solution of fumaric acid (31 mg) in ethanol (1 mL) was added. The reaction mixture was concentrated under reduced pressure, and the residue was solidified with diisopropyl ether to give the title compound as a white powder (yield 109 mg, yield 84%).

$^1$H-NMR (DMSO-d$_6$) δ:2.84-2.92(2H,m), 3.54-3.63(2H, m), 3.84-4.08(1H,m), 4.16-4.27(1H,m), 5.34(1H,brs), 6.62 (2H,s), 7.01-7.10(2H,m), 7.12-7.34(5H,m), 7.36-7.43(1H, m), 7.91-8.00(1H,m), 8.20-8.26(1H,m), 2H not detected.

Example 21

1-[4,5-bis(2-fluorophenyl)thiophen-2-yl]-N-methylmethanamine hydrochloride 4,5-Bis(2-fluorophenyl)thiophene-2-carbaldehyde (140 mg) was dissolved in tetrahydrofuran (3 mL) and methanol (3 mL), and 40% methylamine-methanol solution (0.48 mL) was added. After stirring at room temperature for 5 hr, sodium borohydride (141 mg) was added to the reaction mixture and the mixture was stirred at room temperature for 24 hr. Water was added to the reaction mixture, and the mixture was extracted with ethyl acetate. The extract was washed with saturated aqueous sodium hydrogen carbonate solution and saturated brine, dried over anhydrous sodium sulfate, and concentrated under reduced pressure. The residue was purified by basic silica gel column chromatography (eluent:hexane-ethyl acetate=9:1→2:3) to give a free base of the title compound as a colorless oil (yield 140 mg). The obtained free base (140 mg) was dissolved in diethyl ether (30 mL), and a 4 mol/L hydrogen chloride-ethyl acetate solution (1.4 mL) was added. After stirring at room temperature for 2 hr, the reaction mixture was filtered, and the obtained solid was washed with diethyl ether to give the title compound as a colorless amorphous form (yield 154 mg, 94%).

$^1$H-NMR(DMSO-d$_6$)δ:2.62(3H,s), 4.40(2H,s), 7.10-7.42 (9H,m), 8.85(2H,br).

Example 22

1-{5-[(3-bromophenyl)thio]-1-(2-chlorophenyl)-1H-pyrazol-3-yl}-N-methylmethanamine To a suspension of aluminum chloride (763 mg) in tetrahydrofuran (8 mL) was slowly added lithium aluminum hydride (217 mg) at 0° C., and the mixture was stirred at the same temperature for 30 min. To the obtained suspension was added dropwise a solution of 5-[(3-bromophenyl)thio]-1-(2-chlorophenyl)-N-methyl-1H-pyrazole-3-carboxamide (595 mg) in tetrahydrofuran (2 mL) at 0° C., and the mixture was stirred at room temperature for 1 hr. A 8 mol/L aqueous sodium hydroxide solution was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure to give the title compound as a yellow oil (yield 522 mg, 91%).

$^1$H-NMR(CDCl$_3$)δ:2.51(3H,s), 3.86(2H,s), 6.63(1H,s), 6.96-7.29(6H,m), 7.32-7.39(1H,m), 7.44-7.47(1H,m), 1H not detected.

Example 23

1-{5-[(3-bromophenyl)thio]-1-(2,5-difluorophenyl)-1H-pyrazol-3-yl}-N-methylmethanamine To a suspension of aluminum chloride (1.28 g) in tetrahydrofuran (15 mL) was slowly added lithium aluminum hydride (364 mg) at 0° C., and the mixture was stirred at the same temperature for 15 min. To the obtained suspension was added dropwise a solution of 5-[(3-bromophenyl)thio]-1-(2,5-difluorophenyl)-N-methyl-1H-pyrazole-3-carboxamide (1.35 g) in tetrahydrofuran (7 mL) at 0° C., and the mixture was stirred at room temperature for 1 hr. A 8 mol/L aqueous sodium hydroxide solution was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure to give the title compound as a yellow oil (yield 1.18 g, 90%).

$^1$H-NMR(CDCl$_3$)δ:2.51(3H,s), 3.84(2H,s), 6.63(1H,s), 6.94-7.17(6H,m), 7.25-7.30(1H,m), 1H not detected.

Example 24

1-{1-(2-chlorophenyl)-5-[(6-methylpyridin-2-yl)thio]-1H-pyrazol-3-yl}-N-methylmethanamine To a solution of 1-(2-chlorophenyl)-5-[(6-methylpyridin-2-yl)thio]-1H-pyrazole-3-carbaldehyde (415 mg) in tetrahydrofuran (4 mL) were added 40% methylamine-methanol solution (1.5 mL) and methanol (4 mL) at 0° C., and the mixture was stirred at room temperature for 4 hr. Sodium borohydride (905 mg) was added to the reaction mixture at 0° C. and the mixture was stirred at room temperature for 1 hr. The reaction mixture was concentrated under reduced pressure, water was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure to give the title compound as a yellow oil (yield 450 mg, yield quantitative).
$^1$H-NMR(CDCl$_3$)δ:2.42(3H,s), 2.53(3H,s), 3.89(2H,s), 6.66(1H,d,J=7.8 Hz), 6.72(1H,s), 6.83(1H,d,J=7.8 Hz), 7.20-7.26(1H,m), 7.30-7.36(3H,m), 7.42-7.46(1H,m), 1H not detected.

Example 25

1-{1-(2-chlorophenyl)-5-[(6-methoxypyridin-2-yl)thio]-1H-pyrazol-3-yl}-N-methylmethanamine To a solution of 1-(2-chlorophenyl)-5-[(6-methoxypyridin-2-yl)thio]-1H-pyrazole-3-carbaldehyde (404 mg) in tetrahydrofuran (4 mL) were added 40% methylamine-methanol solution (1.5 mL) and methanol (4 mL) at 0° C. The mixture was stirred at room temperature for 14 hr, and concentrated under reduced pressure. The residue was dissolved in methanol (4 mL), sodium borohydride (76 mg) was added at 0° C., and the mixture was stirred at room temperature for 1 hr. The reaction mixture was concentrated under reduced pressure, saturated aqueous sodium hydrogen carbonate solution was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure to give the title compound as a yellow oil (yield 436 mg, yield quantitative).
$^1$H-NMR(CDCl$_3$)δ:2.52(3H,s), 3.78(3H,s), 3.89(2H,s), 6.41-6.47(2H,m), 6.72(1H,s), 7.21-7.37(4H,m), 7.45-7.48(1H,m), 1H not detected.

Example 26

1-{1-(2-chlorophenyl)-5-[(5-methylpyridin-2-yl)thio]-1H-pyrazol-3-yl}-N-methylmethanamine To a solution of 1-(2-chlorophenyl)-5-[(5-methylpyridin-2-yl)thio]-1H-pyrazole-3-carbaldehyde (422 mg) in tetrahydrofuran (4 mL) were added 40% methylamine-methanol solution (1.3 mL) and methanol (4 mL) at 0° C. The mixture was stirred at room temperature for 16 hr, and concentrated under reduced pressure. The residue was dissolved in methanol (4 mL), sodium borohydride (60 mg) was added at 0° C., and the mixture was stirred at room temperature for 1 hr. The reaction mixture was concentrated under reduced pressure, saturated aqueous sodium hydrogen carbonate solution was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure to give the title compound as a yellow oil (yield 433 mg, 98%).
$^1$H-NMR(CDCl$_3$)δ:2.23(3H,s), 2.52(3H,s), 3.88(2H,s), 6.70(1H,s), 6.79-6.81(1H,m), 7.19-7.35(4H,m), 7.43-7.46(1H,m), 8.15-8.16(1H,m), 1H not detected.

Example 27

1-{1-(2-chlorophenyl)-5-[(6-chloropyridin-3-yl)thio]-1H-pyrazol-3-yl}-N-methylmethanamine hydrochloride tert-Butyl({1-(2-chlorophenyl)-5-[(6-chloropyridin-3-yl)thio]-1H-pyrazol-3-yl}methyl)methylcarbamate (350 mg) was dissolved in ethyl acetate (3 mL) and methanol (2 mL), 4 mol/L hydrogen chloride-ethyl acetate solution (5 mL) was added and the mixture was stirred at room temperature for 3 hr. The reaction mixture was concentrated under reduced pressure, and the residue was crystallized from a mixed solvent of ethyl acetate and hexane, and recrystallized from a mixed solvent of ethyl acetate and ethanol to give the title compound as colorless crystals (yield 252 mg, 83%).
melting point: 175-178° C.
1H-NMR(DMSO-d$_6$)δ:2.53(3H,s), 4.21(2H,s), 7.05(1H,s), 7.44-7.52(3H,m), 7.56-7.69(3H,m), 8.09(1H,s), 9.19(2H,br).

Example 28

N-{3-[(methylamino)methyl]-1-phenyl-1H-pyrazol-5-yl}benzamide 0.5 fumarate

N-(3-Formyl-1-phenyl-1H-pyrazol-5-yl)benzamide (303 mg) was dissolved in tetrahydrofuran (5 mL) and methanol (3 mL), and 40% methylamine-methanol solution (1.1 mL) was added at room temperature. After stirring for 18 hr, the reaction mixture was concentrated under reduced pressure. The residue was dissolved in methanol (3 mL), sodium borohydride (118 mg) was added under ice-cooling and the mixture was further stirred at room temperature for 1 hr. The solvent was evaporated under reduced pressure, water was added to the residue, and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=1:1→ethyl acetate) to give a free base of the title compound as a pale-yellow amorphous form (yield 248 mg). The obtained free base was dissolved in tetrahydrofuran (5 mL), and the mixture was added to a solution of fumaric acid (94 mg) in ethanol (10 mL). The solvent was evaporated under reduced pressure, and the residue was recrystallized from ethanol to give the title compound as colorless crystals (yield 137 mg, yield 37%).
$^1$H-NMR(DMSO-d$_6$)δ:2.44(3H,s), 3.86(2H,s), 6.42(1H,s), 6.50(1H,s), 7.31-7.36(1H,m), 7.43-7.61(7H,m), 7.84-7.86(2H,m), 2H not detected.

Example 29

N-methyl-N-{3-[(methylamino)methyl]-1-phenyl-1H-pyrazol-5-yl}benzenesulfonamide hydrochloride N-(3-formyl-1-phenyl-1H-pyrazol-5-yl)-N-methylbenzenesulfonamide (297 mg) was dissolved in tetrahydrofuran (5 mL) and methanol (3 mL), and 40% methylamine-methanol solution (0.9 mL) was added at room temperature. After stirring for 18 hr, the reaction mixture was concentrated under reduced pressure. The residue was dissolved in methanol (3 mL), sodium borohydride (99 mg) was added under ice-cooling and the mixture was further stirred at room temperature for 1 hr. The reaction mixture was treated with 1 mol/L hydrochloric acid, and the solvent was evaporated under reduced pressure. A saturated aqueous sodium hydrogen carbonate solution was added to the residue, and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=3:1→1:4) to give a free base of the title compound as a pale-yellow oil. The obtained free base was dissolved in ethyl acetate (5 mL), and a 4 mol/L hydrogen chloride-ethyl acetate solution (4 mL) was added. The solvent was evaporated under reduced pressure, and the residue was recrystallized from a mixed solvent of ethyl acetate and ethanol to give the title compound as colorless crystals (yield 175 mg, yield 51%).

$^1$H-NMR(DMSO-$d_6$)δ:2.57(3H,s), 3.05(3H,s), 4.12(2H,s), 6.28(1H,s), 7.45-7.59(5H,m), 7.63-7.80(4H,m), 7.81-7.83(1H,m), 9.25(2H,br).

Example 30

3-[(methylamino)methyl]-N,1-diphenyl-1H-pyrazole-5-amine dihydrochloride tert-Butyl methyl{[1-phenyl-5-(phenylamino)-1H-pyrazol-3-yl]methyl}carbamate (90 mg) was dissolved in ethyl acetate (2 mL) and methanol (1 mL), 4 mol/L hydrogen chloride-ethyl acetate solution (2 mL) was added, and the mixture was stirred at room temperature for 3 hr. The reaction mixture was concentrated under reduced pressure, and the residue was recrystallized from a mixed solvent of ethyl acetate and ethanol to give the title compound as colorless crystals (yield 62 mg, yield 75%).

$^1$H-NMR(DMSO-$d_6$)δ:2.61(3H,t,J=5.4 Hz), 4.12(2H,t, J=5.4 Hz), 6.41(1H,s), 6.75-6.80(1H,m), 6.86-6.89(2H,m), 7.15-7.20(2H,m), 7.34-7.39(1H,m), 7.46-7.51(2H,m), 7.57-7.60(2H,m), 8.22(1H,s), 9.15(3H,br).

Example 31

N-methyl-3-[(methylamino)methyl]-N,1-diphenyl-1H-pyrazole-5-amine hydrochloride tert-Butyl methyl({5-[methyl(phenyl)amino]-1-phenyl-1H-pyrazol-3-yl}methyl)carbamate (67 mg) was dissolved in ethyl acetate (1 mL) and methanol (0.5 mL), a 4 mol/L hydrogen chloride-ethyl acetate solution (2 mL) was added, and the mixture was stirred at room temperature for 2 hr. The reaction mixture was concentrated under reduced pressure, and the residue was crystallized from a mixed solvent of ethyl acetate and hexane, and recrystallized from a mixed solvent of ethyl acetate and ethanol to give the title compound as colorless crystals (yield 25 mg, yield 45%).

$^1$H-NMR(DMSO-$d_6$)δ:2.63(3H,s), 3.08(3H,s), 4.17(2H,s), 6.50(1H,s), 6.65-6.68(2H,m), 6.75-6.80(1H,m), 7.13-7.19(2H,m), 7.29-7.35(1H,m), 7.39-7.48(4H,m), 9.07(2H,br).

Example 32

N-{3-[(methylamino)methyl]-1-phenyl-1H-pyrazol-5-yl}-N-phenylacetamide 0.5 fumarate tert-Butyl({5-[acetyl(phenyl)amino]-1-phenyl-1H-pyrazol-3-yl}methyl)methylcarbamate (83 mg) was dissolved in ethyl acetate (2 mL) and ethanol (1 mL), a 4 mol/L hydrogen chloride-ethyl acetate solution (3 mL) was added, and the mixture was stirred at room temperature for 3 hr. The reaction mixture was concentrated under reduced pressure, saturated aqueous sodium hydrogen carbonate solution was added to the residue, and the mixture was extracted with ethyl acetate. The extract was washed with saturated brine, dried over anhydrous sodium sulfate, and concentrated under reduced pressure. The residue was dissolved in ethyl acetate (3 mL), and the mixture was added to a solution of fumaric acid (23 mg) in ethanol (5 mL). The solvent was evaporated under reduced pressure, and the residue was recrystallized from a mixed solvent of ethyl acetate and ethanol to give the title compound as colorless crystals (yield 32 mg, yield 43%).

$^1$H-NMR(DMSO-$d_6$)δ:1.99(3H,br), 2.41(3H,s), 3.81(2H, s), 6.43(1H,s), 6.68(1H,br), 7.01-7.03(2H,m), 7.10-7.50(8H, m), 2H not detected.

The structures of the compounds described in Reference Examples are shown in Tables 1-8.

TABLE 1

| Ref. Ex. No. | $R^a$ | $R^b$ | $R^c$ | $R^d$ |
|---|---|---|---|---|
| 1 | 4-$O_2N$-C$_6$H$_4$-S-CH$_3$ | 4-$O_2N$-C$_6$H$_4$- | H | $CO_2Et$ |
| 2 | 4-$H_2N$-C$_6$H$_4$-S-CH$_3$ | 4-$H_2N$-C$_6$H$_4$- | H | $CO_2Et$ |
| 3 | C$_6$H$_5$-S-CH$_3$ | C$_6$H$_5$- | H | $CO_2Et$ |
| 4 | C$_6$H$_5$-S-CH$_3$ | C$_6$H$_5$- | H | $CH_2OH$ |
| 5 | C$_6$H$_5$-S-CH$_3$ | C$_6$H$_5$- | H | CHO |

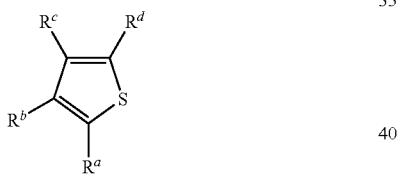

113
Structural formulas of Ref. Ex. Nos. 19-25
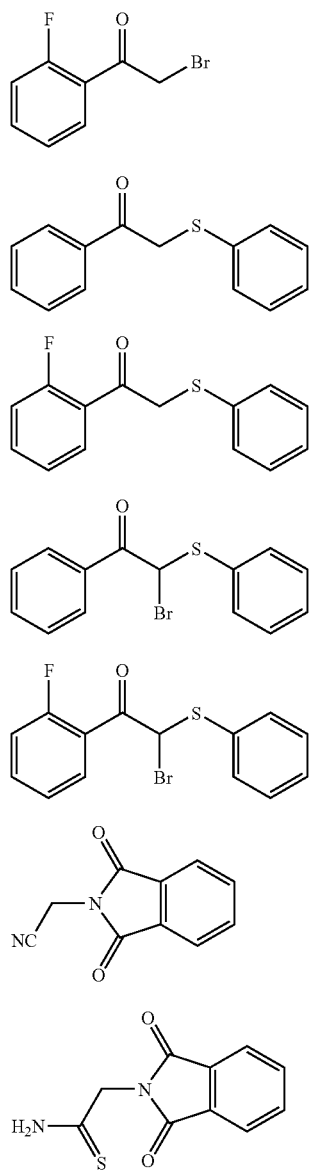
TABLE 5
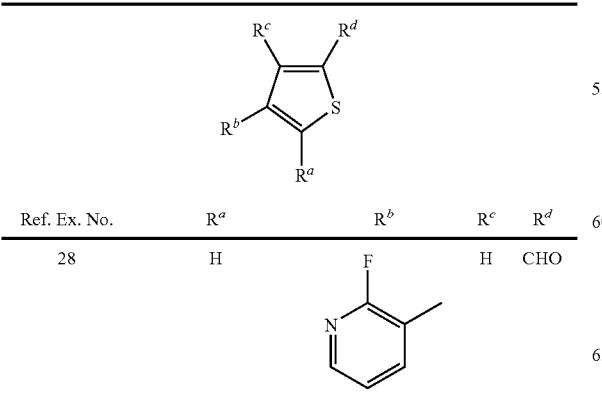
| Ref. Ex. No. | $R^a$ | $R^b$ | $R^c$ | $R^d$ |
|---|---|---|---|---|
| 28 | H | 2-F-3-methylpyridin-4-yl | H | CHO |
114
TABLE 5-continued
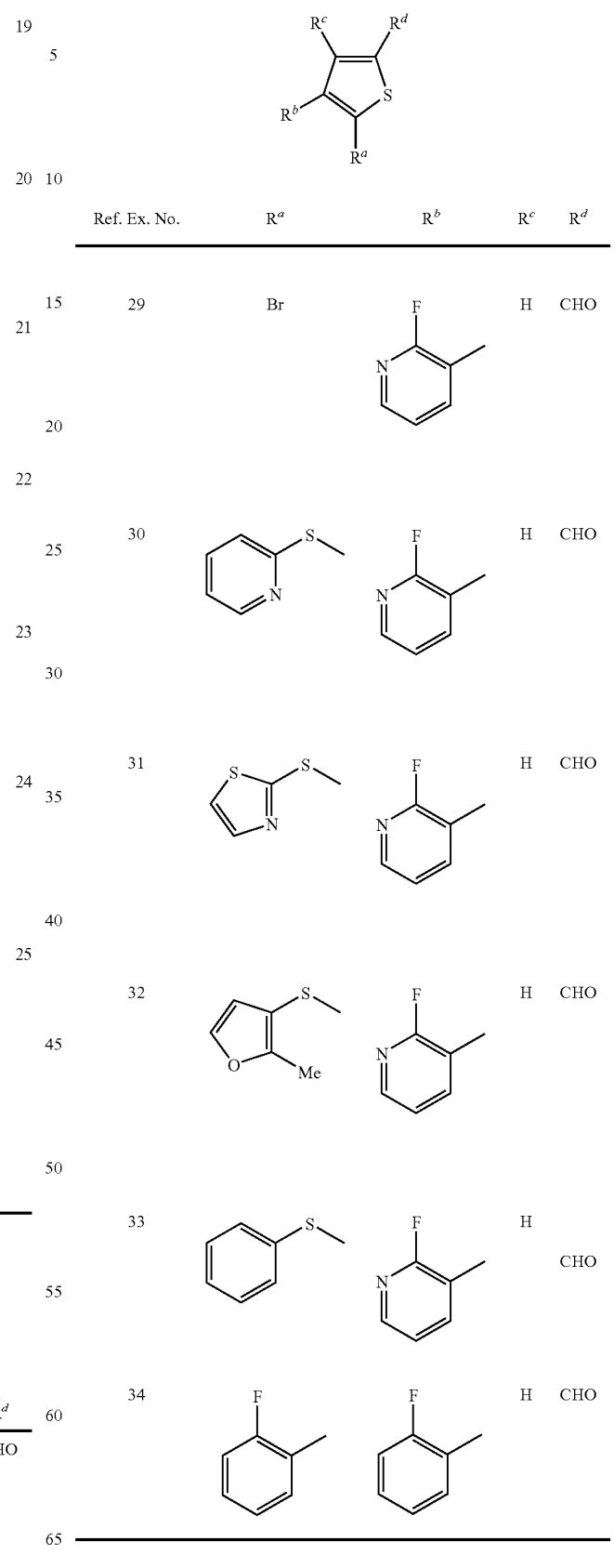

TABLE 6
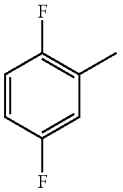
| Ref. Ex. No. | $R^a$ | $R^b$ | $R^c$ | $R^d$ |
|---|---|---|---|---|
| 35 | OH | 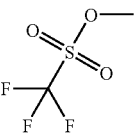 | $CO_2Et$ | H |
| 36 | 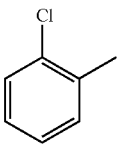 | 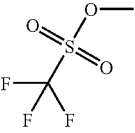 | $CO_2Et$ | H |
| 37 | 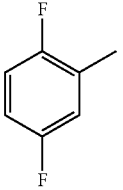 | 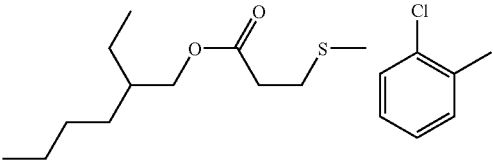 | $CO_2Et$ | H |
| 38 | 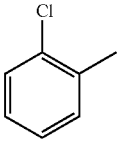 | 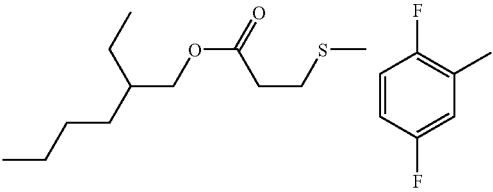 | $CO_2Et$ | H |
| 39 | 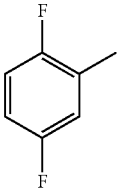 | 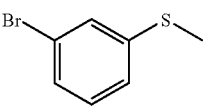 | $CO_2Et$ | H |
| 40 | 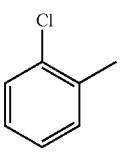 | 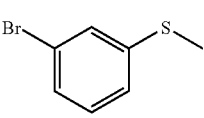 | $CO_2Et$ | H |
| 41 | 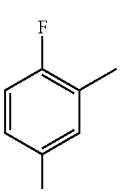 | | $CO_2Et$ | H |

TABLE 6-continued

Pyrazole structure with $R^a$, $R^b$, $R^c$, $R^d$ substituents

| Ref. Ex. No. | $R^a$ | $R^b$ | $R^c$ | $R^d$ |
|---|---|---|---|---|
| 42 | 6-methyl-2-(methylthio)pyridin-3-yl | 2-chlorophenyl | CO₂Et | H |
| 43 | 6-methoxy-2-(methylthio)pyridin-3-yl | 2-chlorophenyl | CO₂Et | H |
| 44 | 5-methyl-2-(methylthio)pyridin-3-yl | 2-chlorophenyl | CO₂Et | H |

TABLE 7

| Ref. Ex. No. | $R^a$ | $R^b$ | $R^c$ | $R^d$ |
|---|---|---|---|---|
| 45 | 6-chloro-3-(methylthio)pyridin-2-yl | 2-chlorophenyl | CO₂Et | H |
| 46 | 3-bromo-5-(methylthio)phenyl | 2-chlorophenyl | CONHMe | H |
| 47 | 3-bromo-5-(methylthio)phenyl | 2,5-difluorophenyl | CONHMe | H |
| 48 | 6-methyl-2-(methylthio)pyridin-3-yl | 2-chlorophenyl | CHO | H |
| 49 | 6-methoxy-2-(methylthio)pyridin-3-yl | 2-chlorophenyl | CHO | H |
| 50 | 5-methyl-2-(methylthio)pyridin-3-yl | 2-chlorophenyl | CHO | H |

TABLE 7-continued
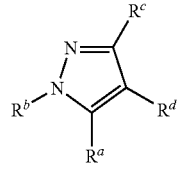
| Ref. Ex. No. | $R^a$ | $R^b$ | $R^c$ | $R^d$ |
|---|---|---|---|---|
| 51 | 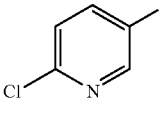 | 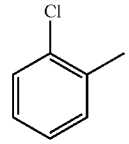 | CONHMe | H |
| 52 | 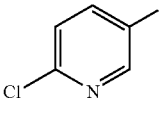 | 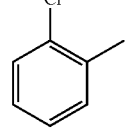 | 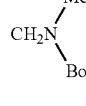 | H |
| 53 | 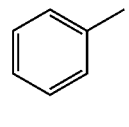 |  | CO$_2$Et | H |
| 54 | 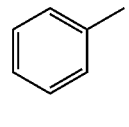 |  | CO$_2$Et | H |
| 55 | 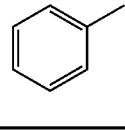 |  | CO$_2$Et | H |
TABLE 8
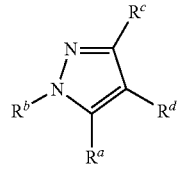
| Ref. Ex. No. | $R^a$ | $R^b$ | $R^c$ | $R^d$ |
|---|---|---|---|---|
| 56 | 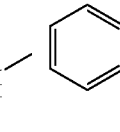 |  | CH$_2$OH | H |
| 57 | 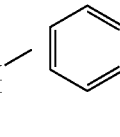 |  | CH$_2$OH | H |
| 58 | 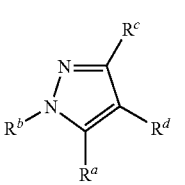 | 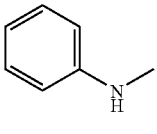 | CH$_2$OH | H |
| 59 |  | 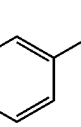 | CHO | H |
| 60 |  | 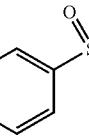 | CHO | H |
| 61 | 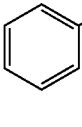 | 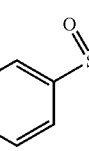 | CHO | H |
| 62 | 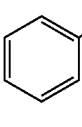 | 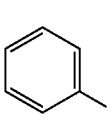 | CHO | H |
| 63 | 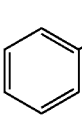 | 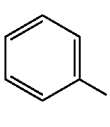 | 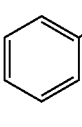 | H |
| 64 | 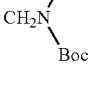 | 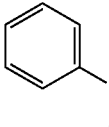 | 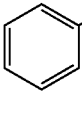 | H |
| 65 | 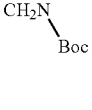 | 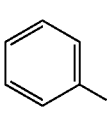 | 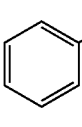 | H |

The structures of the compounds described in Examples are shown in Tables 9-14.

TABLE 9

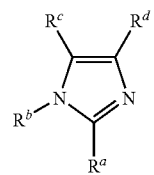

| Ex. No. | $R^a$ | $R^b$ | $R^c$ | $R^d$ | addition salt |
|---|---|---|---|---|---|
| 1 | PhS-CH2- | 4-Me-C6H4- | H | CH2NHMe | 2HCl |

TABLE 9-continued

| Ex. No. | $R^a$ | $R^b$ | $R^c$ | $R^d$ | addition salt |
|---|---|---|---|---|---|
| 2 | Ph-S(O)-CH2- | 4-Me-C6H4- | H | CH2NMe | 2HCl |

TABLE 10

| Ex. No. | $R^a$ | $R^b$ | $R^d$ | $R^e$ | addition salt |
|---|---|---|---|---|---|
| 3 | 4-F-C6H4-CH2CH2- | Ph- | CH2NHMe | H | 2HCl |
| 4 | Ph-CH(CH3)-CH2OH | Ph- | CH2NHMe | H | 2HCl |
| 5 | Ph-CH(CH3)-CO2Me | Ph- | CH2NHMe | H | 2HCl |
| 6 | 4-F-C6H4-CH2CH2- | Ph- | CH2NHMe | Cl | COOH-COOH |
| 7 | 2-pyrimidinyl-CH2- | Ph- | CH2NHMe | H | 2HCl |
| 8 | 4-Me-C6H4-S-CH2CH2- | Ph- | CH2NHMe | H | 2HCl |

TABLE 10-continued
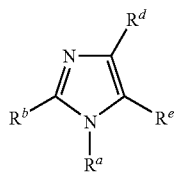
| Ex. No. | $R^a$ | $R^b$ | $R^d$ | $R^e$ | addition salt |
|---|---|---|---|---|---|
| 9 | 4-MeC6H4-SO2-CH2CH2- | C6H5- | CH2NHMe | H | 2HCl |
TABLE 11
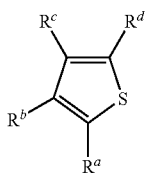
| Ex. No. | $R^a$ | $R^b$ | $R^c$ | $R^d$ | addition salt |
|---|---|---|---|---|---|
| 10 | 3-MeO-C6H4-S-CH2- | 2-F-C6H4- | H | CH2NHMe | fumaric acid |
| 11 | 3-MeO-C6H4-S(O)- | 2-F-C6H4- | H | CH2NHMe | fumaric acid |
| 12 | 2-MeO-C6H4- | 3-Me-C6H4- | H | CH2NHMe | fumaric acid |
| 13 | C6H5-C(O)- | C6H5- | H | CH2NHMe | HCl |
| 14 | C6H5-CH(OH)- | C6H5- | H | CH2NHMe | 0.5 fumaric acid |

TABLE 12

[Structure: thiazole with R^d at 2-position, R^b at 4-position, R^a at 5-position]

| Ex. No. | R^a | R^b | R^d | addition salt |
|---|---|---|---|---|
| 15 | PhS– | 3-methylphenyl | CH₂NH₂ | |
| 16 | PhS– | 2-fluoro-6-methylphenyl | CH₂NH₂ | |

TABLE 13

[Structure: thiophene with R^a at 2, R^b at 3, R^c at 4, R^d at 5]

| Ex. No. | R^a | R^b | R^c | R^d | addition salt |
|---|---|---|---|---|---|
| 17 | (pyridin-2-yl)-S-Me | 2-fluoro-3-methylpyridin-yl | H | CH₂NHMe | |
| 18 | (thiazol-2-yl)-S-Me | 2-fluoro-3-methylpyridin-yl | H | CH₂NHMe | fumarate (HOOC-CH=CH-COOH) |
| 19 | (2-methylfuran-3-yl)-S-Me | 2-fluoro-3-methylpyridin-yl | H | CH₂NHMe | HCl |
| 20 | PhS–Me | 2-fluoro-3-methylpyridin-yl | H | CH₂-(3-hydroxyazetidin-1-yl) | fumarate (HOOC-CH=CH-COOH) |
| 21 | 2-fluoro-6-methylphenyl | 2-fluoro-6-methylphenyl | H | CH₂NHMe | HCl |

TABLE 14
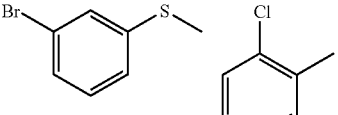
| Ex. No. | R$^a$ | R$^b$ | R$^c$ | R$^d$ | addition salt |
|---|---|---|---|---|---|
| 22 | 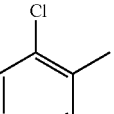 | 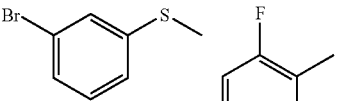 | CH$_2$NHMe | H | |
| 23 | 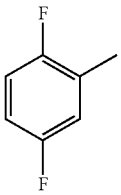 | 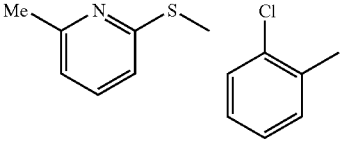 | CH$_2$NHMe | H | |
| 24 | 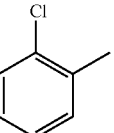 | 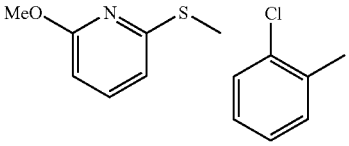 | CH$_2$NHMe | H | |
| 25 | 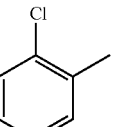 | 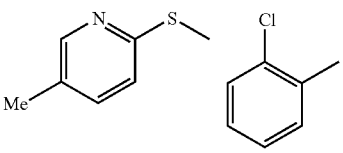 | CH$_2$NHMe | H | |
| 26 | 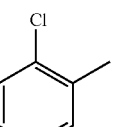 | 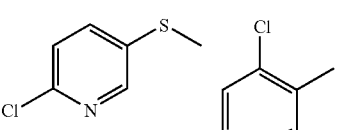 | CH$_2$NHMe | H | |
| 27 | 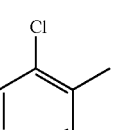 | 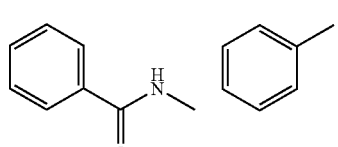 | CH$_2$NHMe | H | HCl |
| 28 | 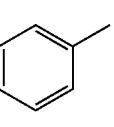 | 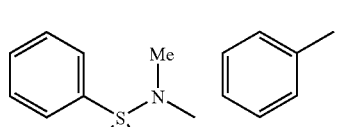 | CH$_2$NHMe | H | HOOC⎯⎯COOH 0.5 |
| 29 | 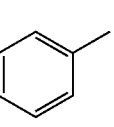 | | CH$_2$NHMe | H | HCl |

TABLE 14-continued

| Ex. No. | $R^a$ | $R^b$ | $R^c$ | $R^d$ | addition salt |
|---|---|---|---|---|---|
| 30 | PhNH- (H on N) | Ph | CH$_2$NHMe | H | 2HCl |
| 31 | PhN(Me)- | Ph | CH$_2$NHMe | H | HCl |
| 32 | PhN(Ac)- | Ph | CH$_2$NHMe | H | HOOC-CH=CH-COOH 0.5 |

Experimental Example 1

Proton Potassium-Adenosine Triphosphatase (H$^+$,K$^+$-ATPase) Inhibitory Activity Test According to the method of Wallmark et al. [Biochim. Biophys. Acta, 728, 31 (1983)], a microsomal fraction of gastric mucosa was prepared from the stomach of swine. First, the stomach was removed, washed with tap water, and immersed in 3 mol/L sodium chloride, and the surface of the mucosa was wiped with a paper towel. The gastric mucosa was removed, minced, and homogenized in a 0.25 mol/L sucrose solution (pH 6.8) containing 1 mmol/L EDTA and 10 mmol/L tris-hydrochloric acid using polytron (Kinematica). The obtained homogenate was centrifuged at 20,000×g for 30 min and the supernatant was centrifuged at 100,000×g for 90 min. The precipitate was suspended in 0.25 mol/L sucrose solution, the suspension was superimposed on a 0.25 mol/L sucrose solution containing 7.5% Ficoll, and centrifuged at 100,000×g for 5 hr. The fraction containing the interface between the both layers was recovered, and centrifugally washed with 0.25 mol/L sucrose solution.

The obtained microsomal fraction was used as an H$^+$/K$^+$-ATPase preparation.

To 50 mmol/L HEPES-tris buffer (5 mmol/L magnesium chloride, 10 mmol/L potassium chloride, 10 μmol/L valinomycin, pH=6.5, 40 μL) containing 2.5 μg/mL enzyme preparation based on the protein concentration was added a test compound (5 μL) dissolved in 10% dimethyl sulfoxide solution, and the mixture was incubated at 37° C. for 30 min. A 2 mmol/L adenosine triphosphate tris salt solution (50 mmol/L HEPES-tris buffer (5 mmol/L magnesium chloride, pH 6.5), 5 μL) was added to start an enzyme reaction. The enzyme reaction was performed at 37° C. for 20 min, and then a malachite green solution (a mixture of 0.12% malachite green sulfate (2.5 mol/L) solution, 7.5% ammonium molybdate and 11% Tween 20 at a ratio of 100:25:2, 15 μL) was added to stop the reaction. The reaction mixture was stood at room temperature for 15 min, and the resulting reaction product of inorganic phosphorus and malachite green was measured by colorimetric quantification at a wavelength of 610 nm. In addition, the amount of inorganic phosphoric acid in a reaction solution free of potassium chloride was also measured in the same manner, and the value was extracted from that in the presence of potassium chloride, whereby the H$^+$,K$^+$-ATPase activity was measured. The inhibitory rate (%) was determined from the activity value of the control and that at each concentration of the test compound, and 50% inhibitory concentration (IC$_{50}$) to H$^+$,K$^+$-ATPase was determined. The results are shown in Table 15.

TABLE 15

| Example No. | H$^+$,K$^+$-ATPase inhibitory activity (IC$_{50}$, μM) |
|---|---|
| 3 | 309 |
| 6 | 1.4 |
| 10 | 0.17 |
| 11 | 0.40 |
| 18 | 2.2 |
| 19 | 0.22 |
| 27 | 0.031 |

From the results of Table 15, it is clear that compound (I) of the present invention has a superior H$^+$,K$^+$-ATPase inhibitory activity.

This application is based on patent application Nos. 2007-256275 and 2008-218852 filed in Japan, and the contents disclosed therein are hereby entirely incorporated by reference. In addition, the patent documents and non-patent documents cited in the present specification are hereby incorporated in their entireties by reference, to the extent that they have been disclosed in the present specification.

The invention claimed is:

1. A compound represented by the formula (I):

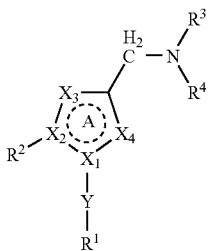

(I)

wherein
ring A is a saturated or unsaturated 5-membered heterocycle containing, as a ring-constituting atom besides carbon atoms, at least one heteroatom selected from a nitrogen atom, an oxygen atom and a sulfur atom, the ring-constituting atom $X_1$ is a carbon atom, the ring-constituting atom $X_2$ is a nitrogen atom, the ring-constituting atom $X_3$ is a nitrogen atom, the ring-constituting atom $X_4$ is a carbon atom, and each ring-constituting atom optionally has substituent(s) selected from an optionally substituted alkyl group, an acyl group, an optionally substituted hydroxy group, an optionally substituted mercapto group, an optionally substituted amino group, a halogen atom, a cyano group and a nitro group;
$R^1$ is a $C_{6-14}$ aryl group, an alicyclic hydrocarbon group, or a heterocyclic group, each of which is optionally substituted by 1 to 3 substituents selected from (i) a halogen atom, (ii) hydroxy, (iii) cyano, (iv) $C_{1-6}$ alkyl optionally substituted by 1 to 5 halogen atoms, (v) $C_{1-6}$ alkoxy optionally substituted by 1 to 5 halogen atoms, (vi) amino optionally mono- or di-substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino;
$R^2$ is a $C_{6-14}$ aryl group, an alicyclic hydrocarbon group or a heterocyclic group, each of which optionally has substituent(s);
$R^3$ and $R^4$ are the same or different and each is a hydrogen atom or an alkyl group, or $R^3$ and $R^4$ optionally form, together with the adjacent nitrogen atom, an optionally substituted nitrogen-containing heterocycle;
Y is a spacer selected from
(1) a bond,
(2) a $C_{1-6}$ alkylene group optionally substituted by 1 to 3 substituents selected from a halogen atom, hydroxy, oxo and $C_{1-6}$ alkoxy-carbonyl,
(3) (i) —O—;
(ii) —O—$R^{5'}$— wherein $R^{5'}$ is a $C_{1-6}$ alkylene group optionally substituted by 1 to 3 substituents selected from a halogen atom, hydroxy and oxo;
(iii) —O—$R^{5'}$—O— wherein $R^{5'}$ is as defined above;
(iv) —O—$R^{5'}$—S— wherein $R^{5'}$ is as defined above;
(v) —O—$R^{5'}$—$NR^{7'}$— wherein $R^{5'}$ is as defined above, and $R^{7'}$ is (a) a hydrogen atom, (b) $C_{1-6}$ alkyl optionally substituted by 1 to 3 halogen atoms or hydroxy, (c) $C_{1-6}$ alkyl-carbonyl or (d) $C_{1-6}$ alkylsulfonyl;
(vi) —O—$NR^{7'}$— wherein $R^{7'}$ is as defined above;
(4) (i) —N($R^{8'}$)— wherein $R^{8'}$ is (a) a hydrogen atom, (b) $C_{1-6}$ alkyl optionally substituted by 1 to 3 halogen atoms or hydroxy, (c) $C_{1-6}$ alkyl-carbonyl or (d) $C_{1-6}$ alkylsulfonyl;

(ii) —N($R^{8'}$)—$R^{9'}$— wherein $R^{8'}$ is as defined above, and $R^{9'}$ is a $C_{1-6}$ alkylene group optionally substituted by 1 to 3 substituents selected from a halogen atom, hydroxy and oxo;
(5) —S—;
—SO—;
(6) (i) —S—$R^{10'}$— wherein $R^{10'}$ is a $C_{1-6}$ alkylene group optionally substituted by 1 to 3 substituents selected from a halogen atom, hydroxy and oxo;
(ii) —S—N($R^{11'}$)— wherein $R^{11'}$ is (a) a hydrogen atom, (b) $C_{1-6}$ alkyl optionally substituted by 1 to 3 halogen atoms or hydroxy, (c) $C_{1-6}$ alkyl-carbonyl or (d) $C_{1-6}$ alkylsulfonyl;
(iii) —S—N($R^{11'}$)—$R^{12'}$— wherein $R^{11'}$ is as defined above, and $R^{12'}$ is a $C_{1-6}$ alkylene group optionally substituted by 1 to 3 substituents selected from a halogen atom, hydroxy and oxo;
(iv) —SO—$R^{10'}$— wherein $R^{10'}$ is as defined above;
(v) —SO—N($R^{11'}$)— wherein $R^{11'}$ is as defined above;
(vi) —SO—N($R^{11'}$)—$R^{12'}$— wherein $R^{11'}$ and $R^{12'}$ are each as defined above;
(vii) —$SO_2$—$R^{10'}$— wherein $R^{10'}$ is as defined above;
(viii) —$SO_2$—N($R^{11'}$)— wherein $R^{11'}$ is as defined above;
(ix) —$SO_2$—N($R^{11'}$)—$R^{12'}$— wherein $R^{11'}$ and $R^{12'}$ are each as defined above;
(x) —$SO_2$—O—;
(xi) —$SO_2$—N($R^{11'}$)—$SO_2$— wherein $R^{11'}$ is as defined above;
or a salt thereof, excluding one wherein a cyclic group for $R^2$ has an aminosulfonyl group as a substituent, N-methyl-1-[1-phenyl-2-(phenylthio)-1H-imidazol-4-yl]methanamine and 1-[4-phenyl-5-(phenylthio)-1,3-thiazol-2-yl]methanamine.

2. A compound represented by the formula (I)

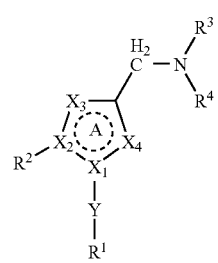

(I)

wherein ring A is a saturated or unsaturated 5-membered heterocycle containing, as a ring-constituting atom besides carbon atoms, at least one heteroatom selected from a nitrogen atom, an oxygen atom and a sulfur atom, the ring-constituting atom $X_1$ is a carbon atom, the ring-constituting atom $X_2$ is a nitrogen atom, the ring-constituting atom $X_3$ is a nitrogen atom, the ring-constituting atom $X_4$ is a carbon atom, and each ring-constituting atom optionally has substituent(s) selected from an optionally substituted alkyl group, an acyl group, an optionally substituted hydroxy group, an optionally substituted mercapto group, an optionally substituted amino group, a halogen atom, a cyano group and a nitro group;
$R^1$ is a $C_{6-14}$ aryl group, an alicyclic hydrocarbon group, or a heterocyclic group, each of which is optionally substituted by 1 to 3 substituents selected from (i) a halogen atom, (ii) hydroxy, (iii) cyano, (iv) $C_{1-6}$ alkyl optionally substituted by 1 to 5 halogen atoms, (v) $C_{1-6}$ alkoxy optionally substituted by 1 to 5 halogen atoms, (vi)

amino optionally mono- or di-substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino;

$R^2$ is a $C_{6-14}$ aryl group, an alicyclic hydrocarbon group or a heterocyclic group, each of which optionally has substituent(s);

$R^3$ and $R^4$ are the same or different and each is a hydrogen atom or an alkyl group;

Y is a spacer selected from
(1) a bond,
(2) a $C_{1-6}$ alkylene group optionally substituted by 1 to 3 substituents selected from a halogen atom, hydroxy, oxo and $C_{1-6}$ alkoxy-carbonyl,
(3) (i) —O—;
(ii) —O—$R^{5'}$— wherein $R^{5'}$ is a $C_{1-6}$ alkylene group optionally substituted by 1 to 3 substituents selected from a halogen atom, hydroxy and oxo;
(iii) —O—$R^{5'}$—O— wherein $R^{5'}$ is as defined above;
(iv) —O—$R^{5'}$—S— wherein $R^{5'}$ is as defined above;
(v) —O—$R^{5'}$—$NR^{7'}$— wherein $R^{5'}$ is as defined above, and $R^{7'}$ is (a) a hydrogen atom, (b) $C_{1-6}$ alkyl optionally substituted by 1 to 3 halogen atoms or hydroxy, (c) $C_{1-6}$ alkyl-carbonyl or (d) $C_{1-6}$ alkylsulfonyl;
(vi) —O—$NR^{7'}$— wherein $R^{7'}$ is as defined above,
(4) (i) —$N(R^{8'})$— wherein $R^{8'}$ is (a) a hydrogen atom, (b) $C_{1-6}$ alkyl optionally substituted by 1 to 3 halogen atoms or hydroxy, (c) $C_{1-6}$ alkyl-carbonyl or (d) $C_{1-6}$ alkylsulfonyl;
(ii) —$N(R^{8'})$—$R^{9'}$— wherein $R^{8'}$ is as defined above, and $R^{9'}$ is a $C_{1-6}$ alkylene group optionally substituted by 1 to 3 substituents selected from a halogen atom, hydroxy and oxo;
(5) —S—;
—SO—;
(6) (i) —S—$R^{10'}$— wherein $R^{10'}$ is a $C_{1-6}$ alkylene group optionally substituted by 1 to 3 substituents selected from a halogen atom, hydroxy and oxo;
(ii) —S—$N(R^{11'})$— wherein $R^{11'}$ is (a) a hydrogen atom, (b) $C_{1-6}$ alkyl optionally substituted by 1 to 3 halogen atoms or hydroxy, (c) $C_{1-6}$ alkyl-carbonyl or (d) $C_{1-6}$ alkylsulfonyl;
(iii) —S—$N(R^{11'})$—$R^{12'}$— wherein $R^{11'}$ is as defined above, and $R^{12'}$ is a $C_{1-6}$ alkylene group optionally substituted by 1 to 3 substituents selected from a halogen atom, hydroxy and oxo;
(iv) —SO—$R^{10'}$— wherein $R^{10'}$ is as defined above;
(v) —SO—$N(R^{11'})$— wherein $R^{11'}$ is as defined above;
(vi) —SO—$N(R^{11'})$—$R^{12'}$— wherein $R^{11'}$ and $R^{12'}$ are each as defined above;
(vii) —$SO_2$—$R^{10'}$— wherein $R^{10'}$ is as defined above;
(viii) —$SO_2$—$N(R^{11'})$— wherein $R^{11'}$ is as defined above;
(ix) —$SO_2$—$N(R^{11'})$—$R^{12'}$— wherein $R^{11'}$ and $R^{12'}$ are each as defined above;
(x) —$SO_2$—O—;
(xi) —$SO_2$—$N(R^{11'})$—$SO_2$— wherein $R^{11'}$ is as defined above;
excluding one wherein a cyclic group for $R^2$ has an aminosulfonyl group as a substituent, N-methyl-1-[1-phenyl-2-(phenylthio)-1H-imidazol-4-yl]methanamine and 1-[4-phenyl-5-(phenylthio)-1,3-thiazol-2-yl]methanamine, or a salt thereof.

3. The compound according to claim 1, wherein $R^3$ and $R^4$ are each a hydrogen atom or an alkyl group, or a salt thereof.

4. The compound according to claim 1 or 2, wherein the partial structure of the formula (I)

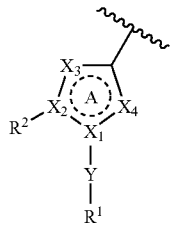

is

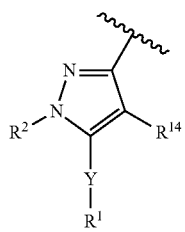

wherein $R^{13}$ and $R^{14}$ are the same or different and each is a hydrogen atom, an optionally substituted alkyl group, an acyl group, an optionally substituted hydroxy group, an optionally substituted mercapto group, an optionally substituted amino group, a halogen atom, a cyano group or a nitro group, and other symbols are as defined in claim 1, or a salt thereof.

5. The compound according to claim 1 or 2, wherein the substituent which a carbon atom optionally has is a halogen atom when $X_4$ is a carbon atom, or a salt thereof.

6. The compound according to claim 1 or 2, wherein Y is a spacer selected from
(1) a bond,
(2) a methylene group optionally having substituent(s),
(3) —O—,
(4) —$S(O)_q$— wherein q is 0 or 1, and
(5) —$S(O)_r$—$R^{10}$— wherein $R^{10}$ is a methylene group optionally having substituent(s), r is 0, 1 or 2, or a salt thereof.

7. The compound according to claim 1 or 2, wherein $R^2$ is a group represented by

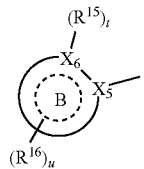

wherein ring B is a cyclic group having $X_5$ and $X_6$ as ring-constituting atoms, $X_5$ is a carbon atom or a nitrogen atom, $X_6$ is a carbon atom, a nitrogen atom, an oxygen atom or a sulfur atom;

$R^{15}$ is a substituent that $X_6$ optionally has when $X_6$ is a carbon atom or a nitrogen atom;

$R^{16}$ is an optionally substituted alkyl group, an acyl group, an optionally substituted hydroxy group, an optionally substituted mercapto group, an optionally substituted amino group, a halogen atom, a cyano group or a nitro group;

t is 0 or 1; and u is an integer of 0 to 3, or a salt thereof.

8. 1-{1-(2-Chlorophenyl)-5-[(6-chloropyridin-3-yl)thio]-1H-pyrazol-3-yl}-N-methylmethanamine or a salt thereof.

9. A medicament comprising a compound represented by the formula (I)

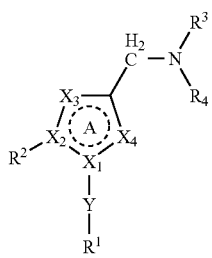

(I)

wherein ring A is a saturated or unsaturated 5-membered heterocycle containing, as a ring-constituting atom besides carbon atoms, at least one heteroatom selected from a nitrogen atom, an oxygen atom and a sulfur atom, the ring-constituting atom $X_1$ is a carbon atom, the ring-constituting atom $X_2$ is a nitrogen atom, the ring-constituting atom $X_3$ is a nitrogen atom, the ring-constituting atom $X_4$ is a carbon atom, and each ring-constituting atom optionally has substituent(s) selected from an optionally substituted alkyl group, an acyl group, an optionally substituted hydroxy group, an optionally substituted mercapto group, an optionally substituted amino group, a halogen atom, a cyano group and a nitro group;

$R^1$ is a $C_{6-14}$ aryl group, an alicyclic hydrocarbon group, or a heterocyclic group, each of which is optionally substituted by 1 to 3 substituents selected from (i) a halogen atom, (ii) hydroxy, (iii) cyano, (iv) $C_{1-6}$ alkyl optionally substituted by 1 to 5 halogen atoms, (v) $C_{1-6}$ alkoxy optionally substituted by 1 to 5 halogen atoms, (vi) amino optionally mono- or di-substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino;

$R^2$ is a $C_{6-14}$ aryl group, an alicyclic hydrocarbon group or a heterocyclic group, each of which optionally has substituent(s);

$R^3$ and $R^4$ are the same or different and each is a hydrogen atom or an alkyl group, or $R^3$ and $R^4$ optionally form, together with the adjacent nitrogen atom, an optionally substituted nitrogen-containing heterocycle;

Y is a spacer selected from,
(1) a bond,
(2) a $C_{1-6}$ alkylene group optionally substituted by 1 to 3 substituents selected from a halogen atom, hydroxy, oxo and $C_{1-6}$ alkoxy-carbonyl,
(3) (i) —O—;
(ii) —O—$R^{5'}$— wherein $R^{5'}$ is a $C_{1-6}$ alkylene group optionally substituted by 1 to 3 substituents selected from a halogen atom, hydroxy and oxo;
(iii) —O—$R^{5'}$—O— wherein $R^{5'}$ is as defined above;
(iv) —O—$R^{5'}$—S— wherein $R^{5'}$ is as defined above;
(v) —O—$R^{5'}$—$NR^{7'}$— wherein $R^{5'}$ is as defined above, and $R^{7'}$ is (a) a hydrogen atom, (b) $C_{1-6}$ alkyl optionally substituted by 1 to 3 halogen atoms or hydroxy, (c) $C_{1-6}$ alkyl-carbonyl or (d) $C_{1-6}$ alkylsulfonyl;
(vi) —O—$NR^{7'}$— wherein $R^{7'}$ is as defined above,
(4) (i) —N($R^{8'}$)— wherein $R^{8'}$ is (a) a hydrogen atom, (b) $C_{1-6}$ alkyl optionally substituted by 1 to 3 halogen atoms or hydroxy, (c) $C_{1-6}$ alkyl-carbonyl or (d) $C_{1-6}$ alkylsulfonyl;
(ii) —N($R^{8'}$)—$R^{9'}$— wherein $R^{8'}$ is as defined above, and $R^{9'}$ is a $C_{1-6}$ alkylene group optionally substituted by 1 to 3 substituents selected from a halogen atom, hydroxy and oxo;
(5) —S—;
—SO—;
(6) (i) —S—$R^{10'}$— wherein $R^{10'}$ is a $C_{1-6}$ alkylene group optionally substituted by 1 to 3 substituents selected from a halogen atom, hydroxy and oxo;
(ii) —S—N($R^{11'}$)— wherein $R^{11'}$ is (a) a hydrogen atom, (b) $C_{1-6}$ alkyl optionally substituted by 1 to 3 halogen atoms or hydroxy, (c) $C_{1-6}$ alkyl-carbonyl or (d) $C_{1-6}$ alkylsulfonyl;
(iii) —S—N($R^{11'}$)—$R^{12'}$— wherein $R^{11'}$ is as defined above, and $R^{12'}$ is a $C_{1-6}$ alkylene group optionally substituted by 1 to 3 substituents selected from a halogen atom, hydroxy and oxo;
(iv) —SO—$R^{10'}$— wherein $R^{10'}$ is as defined above;
(v) —SO—N($R^{11'}$)— wherein $R^{11'}$ is as defined above;
(vi) —SO—N($R^{11'}$)—$R^{12'}$— wherein $R^{11'}$ and $R^{12'}$ are each as defined above;
(vii) —$SO_2$—$R^{10'}$— wherein $R^{10'}$ is as defined above;
(viii) —$SO_2$—N($R^{11'}$)— wherein $R^{11'}$ is as defined above;
(ix) —$SO_2$—N($R^{11'}$)—$R^{12'}$— wherein $R^{11'}$ and $R^{12'}$ are each as defined above;
(x) —$SO_2$—O—;
(xi) —$SO_2$—N($R^{11'}$)—$SO_2$— wherein $R^{11'}$ is as defined above;
or a salt thereof, and a pharmacologically acceptable carrier.

* * * * *

UNITED STATES PATENT AND TRADEMARK OFFICE
CERTIFICATE OF CORRECTION

PATENT NO. : 8,334,301 B2
APPLICATION NO. : 12/680184
DATED : December 18, 2012
INVENTOR(S) : Haruyuki Nishida et al.

Page 1 of 1

It is certified that error appears in the above-identified patent and that said Letters Patent is hereby corrected as shown below:

In the Claims

Column 134, line 25 in Claim 4: please delete "wherein $R^{13}$ and $R^{14}$ are the same or different and each is" and substitute -- wherein $R^{14}$ is --.

Signed and Sealed this
Twenty-second Day of October, 2013

Teresa Stanek Rea
*Deputy Director of the United States Patent and Trademark Office*